United States Patent
Jeong et al.

(10) Patent No.: US 11,549,243 B2
(45) Date of Patent: Jan. 10, 2023

(54) LIQUID DISPENSING DEVICE

(71) Applicant: LG ELECTRONICS INC., Seoul (KR)

(72) Inventors: Soongy Jeong, Seoul (KR); Jewook Jeon, Seoul (KR); Dongkoo Han, Seoul (KR); Jingyu Ji, Seoul (KR); Sangnam Kim, Seoul (KR); Jongwon Yun, Seoul (KR); Junki Yeo, Seoul (KR); Youngseok Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 371 days.

(21) Appl. No.: 16/796,090

(22) Filed: Feb. 20, 2020

(65) Prior Publication Data
US 2020/0270851 A1 Aug. 27, 2020

(30) Foreign Application Priority Data
Feb. 22, 2019 (KR) .................. 10-2019-0021252

(51) Int. Cl.
*E03C 1/046* (2006.01)
*A61L 2/18* (2006.01)
(Continued)

(52) U.S. Cl.
CPC ............. *E03C 1/046* (2013.01); *A61L 2/18* (2013.01); *E03C 1/0404* (2013.01);
(Continued)

(58) Field of Classification Search
CPC ........ E03C 1/046; E03C 1/0404; E03C 1/055; E03C 1/057; A61L 2/18; A61L 2202/15; Y10T 137/9464
(Continued)

(56) References Cited

U.S. PATENT DOCUMENTS 718,935 A 1/1903 Johnson
2,324,741 A 7/1943 Svabek, Jr.
(Continued)

FOREIGN PATENT DOCUMENTS

CN 202706119 1/2013
CN 206127025 U 4/2017
(Continued)

OTHER PUBLICATIONS

Korean Notice of Allowance dated Oct. 27, 2020 issued in KR Application No. 10-2019-0021252.
(Continued)

*Primary Examiner* — Daphne M Barry
*Assistant Examiner* — Frederick D Soski
(74) *Attorney, Agent, or Firm* — Ked & Associates, LLP

(57) ABSTRACT

Provided is a liquid dispensing device. The liquid dispensing device includes a cylinder body coupled to a sink and at least one nozzle coupled to the cylinder body. The at least one nozzle may include a first liquid discharge nozzle coupled to an upper region of the cylinder body to extend horizontally, the first liquid discharge nozzle being configured to supply a drinkable liquid, such as a purified liquid, a heated liquid, or a cooled liquid. The at least one nozzle may a second liquid discharge nozzle coupled to the cylinder body to extend horizontally, the second liquid discharge nozzle being positioned to be spaced apart from the first liquid discharge nozzle to supply a non-drinkable liquid, such as a sterilizing liquid containing hypochlorous acid or other additive.

36 Claims, 33 Drawing Sheets

(51) Int. Cl.
  *E03C 1/04* (2006.01)
  *E03C 1/05* (2006.01)
(52) U.S. Cl.
  CPC ........... *A61L 2202/15* (2013.01); *E03C 1/055* (2013.01); *E03C 1/057* (2013.01); *Y10T 137/9464* (2015.04)
(58) Field of Classification Search
  USPC ....................................................... 222/331
  See application file for complete search history.

(56) References Cited

U.S. PATENT DOCUMENTS

| | | | |
|---|---|---|---|
| 5,547,584 A | 8/1996 | Capehart | |
| 5,997,738 A | 12/1999 | Lin | |
| 7,552,747 B1 | 6/2009 | Sargsyan | |
| 7,819,136 B1* | 10/2010 | Eddy | G01F 11/00 137/624.11 |
| 8,089,473 B2* | 1/2012 | Koottungal | H03K 17/975 345/173 |
| 8,118,240 B2* | 2/2012 | Rodenbeck | E03C 1/0404 239/407 |
| 9,656,896 B2 | 5/2017 | Kim et al. | |
| 9,919,939 B2 | 3/2018 | Rosko | |
| 10,266,441 B2 | 4/2019 | Lee et al. | |
| 10,723,642 B2 | 7/2020 | Moon et al. | |
| 11,242,675 B2* | 2/2022 | Chung | E03C 1/0404 |
| 2002/0040867 A1 | 4/2002 | Conrad | |
| 2005/0133100 A1* | 6/2005 | Bolderheij | E03C 1/0404 137/801 |
| 2006/0075547 A1* | 4/2006 | Hamilton | E03C 1/055 4/559 |
| 2006/0151523 A1* | 7/2006 | Fetzer | E03C 1/055 222/14 |
| 2006/0162795 A1 | 7/2006 | Gloor et al. | |
| 2006/0218721 A1* | 10/2006 | Ho | A61H 33/6036 4/615 |
| 2006/0226081 A1 | 10/2006 | Lupton | |
| 2006/0253973 A1* | 11/2006 | Brooks | E03C 1/242 4/559 |
| 2007/0022529 A1* | 2/2007 | Thorne | E03C 1/0404 4/678 |
| 2007/0152074 A1* | 7/2007 | Stowe | E03C 1/055 236/12.1 |
| 2007/0261161 A1* | 11/2007 | Avigdor | E03C 1/0408 4/598 |
| 2008/0000997 A1* | 1/2008 | Smith | E03C 1/055 29/729 |
| 2008/0203195 A1* | 8/2008 | Schmitt | E03C 1/055 239/548 |
| 2008/0217358 A1 | 9/2008 | Tavolazzi | |
| 2009/0100594 A1* | 4/2009 | Chen | E03C 1/04 4/678 |
| 2009/0293189 A1* | 12/2009 | Somerville | G01K 13/02 4/597 |
| 2009/0320949 A1* | 12/2009 | Liao | E03C 1/055 137/801 |
| 2011/0062359 A1* | 3/2011 | Zelikovich | E03C 1/052 251/129.04 |
| 2011/0203364 A1* | 8/2011 | Staake | F24D 19/1063 73/198 |
| 2013/0062219 A1 | 3/2013 | Lee et al. | |
| 2014/0230143 A1* | 8/2014 | Morales | E03C 1/0404 4/676 |
| 2014/0366264 A1* | 12/2014 | Ciavarella | A47K 5/1217 4/678 |
| 2016/0022849 A1* | 1/2016 | Hecht | A61L 2/00 250/455.11 |
| 2016/0160481 A1* | 6/2016 | Lev | E03C 1/0404 137/801 |
| 2016/0177551 A1* | 6/2016 | Li | G01R 33/07 324/251 |
| 2016/0229715 A1 | 8/2016 | Kim et al. | |
| 2017/0321931 A1 | 11/2017 | Choi | |
| 2018/0002153 A1* | 1/2018 | Kim | B67D 1/0888 |
| 2018/0321070 A1* | 11/2018 | Velestuk | G01F 1/44 |
| 2019/0001006 A1* | 1/2019 | Rodenbeck | C02F 1/4672 |
| 2019/0308892 A1 | 10/2019 | Yu et al. | |
| 2019/0323215 A1 | 10/2019 | Zhou et al. | |
| 2020/0216331 A1 | 7/2020 | Jeon | |
| 2020/0270150 A1 | 8/2020 | Jeon | |
| 2020/0270851 A1 | 8/2020 | Jeong | |

FOREIGN PATENT DOCUMENTS

| | | |
|---|---|---|
| CN | 106122533 | 4/2018 |
| CN | 108561603 | 9/2018 |
| CN | 109185526 | 1/2019 |
| EP | 0 679 770 | 11/1995 |
| EP | 1686218 | 8/2006 |
| JP | H07-42210 | 2/1995 |
| JP | H10-263542 | 10/1998 |
| JP | 2010-051879 | 3/2010 |
| JP | 5010289 | 8/2012 |
| JP | 2014-178048 | 9/2014 |
| KR | 20-0276610 | 5/2002 |
| KR | 20-0371538 | 1/2005 |
| KR | 20-0371538 Y1 | 1/2005 |
| KR | 10-2005-0121371 | 12/2005 |
| KR | 10-2009-0090833 | 8/2009 |
| KR | 2010-0026589 A | 3/2010 |
| KR | 10-2010-0039770 | 4/2010 |
| KR | 10-2010-0051046 | 5/2010 |
| KR | 10-1023771 | 3/2011 |
| KR | 10-2014-0023093 | 2/2014 |
| KR | 10-2014-0033772 | 3/2014 |
| KR | 2014-0033772 A | 3/2014 |
| KR | 10-2014-0111551 | 9/2014 |
| KR | 10-2014-0130758 | 11/2014 |
| KR | 2014-0130758 A | 11/2014 |
| KR | 20-0481313 | 9/2016 |
| KR | 10-2017-0034849 | 3/2017 |
| KR | 20-2018-0000827 | 3/2018 |
| KR | 2018-0000827 U | 3/2018 |
| KR | 10-2018-0045758 | 5/2018 |
| KR | 10-2018-0063657 | 6/2018 |
| KR | 10-2018-0066578 | 6/2018 |
| KR | 10-1884736 | 8/2018 |
| KR | 10-1896201 | 9/2018 |
| KR | 10-2018-0118579 | 10/2018 |
| WO | WO 2001/042143 A2 | 6/2002 |
| WO | WO 2011/145902 | 11/2011 |

OTHER PUBLICATIONS

Korean Office Action dated Feb. 1, 2021 issued in KR Application No. 10-2020-0153979.
United States Office Action dated Jul. 28, 2021 issued in co-pending related U.S. Appl. No. 16/796,144.
Korean Office Action dated May 1, 2020 issued in KR Application No. 10-2019-0021253.
European Search Report dated Jul. 2, 2020 issued in EP Application No. 20158716.9.
U.S. Notice of Allowance issued in U.S. Appl. No. 16/796,144 dated Nov. 18, 2021.
European Notice of Allowance dated Jan. 19, 2022 issued in Application 20 158 679.9.
U.S. Office Action dated Apr. 12, 2022 issued in U.S. Appl. No. 16/796,014.
Korean Notice of Allowance dated Nov. 12, 2020 issued in KR Application No. 10-2019-0021253.
Korean Office Action dated Feb. 10, 2021 issued in KR Application No. 10-2020-0153974.
Korean Office Action dated Feb. 15, 2021 issued in KR Application No. 10-2020-0153967.
Korean Office Action dated Feb. 15, 2021 issued in KR Application No. 10-2020-0155700.
U.S. Appl. No. 16/796,014, filed Feb. 20, 2020.
U.S. Appl. No. 16/796,090, filed Feb. 20, 2020.

(56) References Cited

OTHER PUBLICATIONS

U.S. Appl. No. 17/673,289, filed Feb. 16, 2022.
U.S. Appl. No. 16/796,144, filed Feb. 20, 2020.
Korean Office Action dated Apr. 25, 2020 issued in KR Application No. 10-2019-0021251.
Korean Office Action dated Apr. 26, 2020 issued in KR Application No. 10-2019-0021252.
European Search Report dated Jun. 30, 2020 issued in EP Application No. 20158767.2.
European Search Report dated Jun. 30, 2020 issued in EP Application No. 20158679.9.
Extended European Search Report dated Jul. 29, 2022 issued in Application 22182345.3.

* cited by examiner

FIG. 4
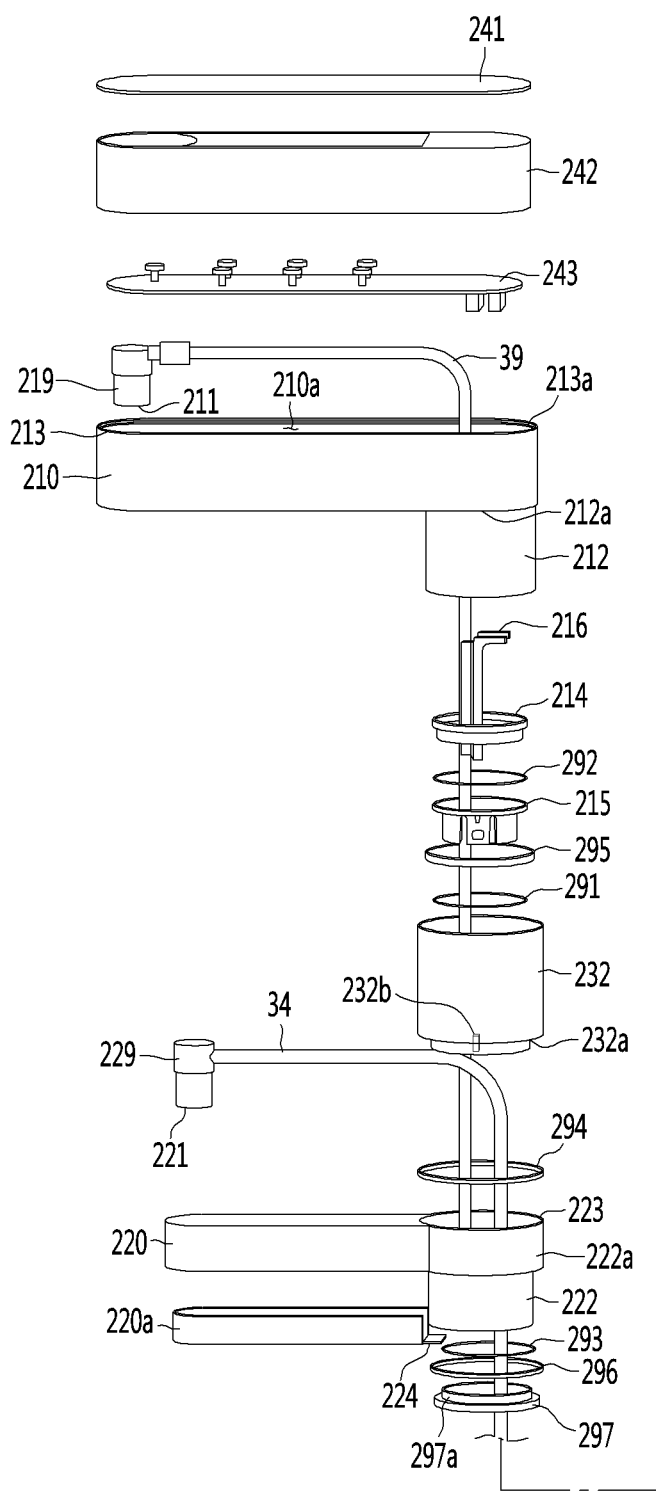
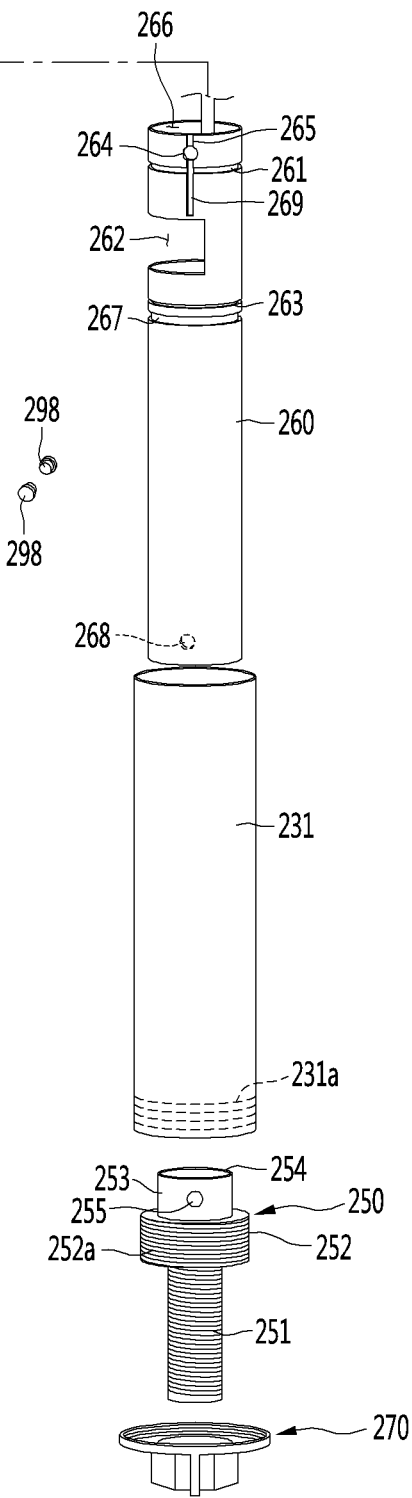

FIG. 7C
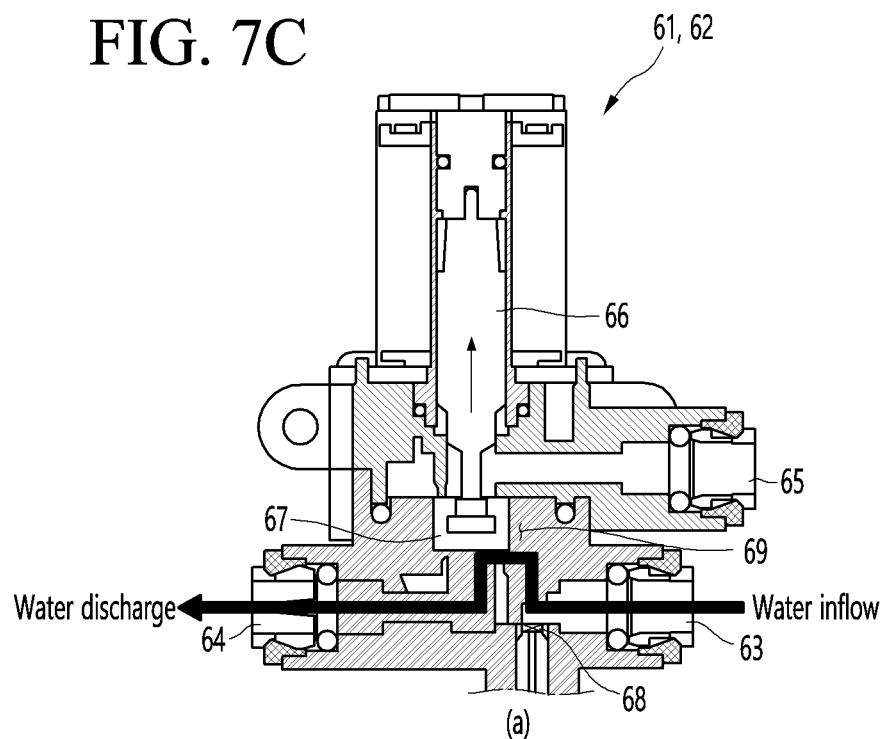
(a)
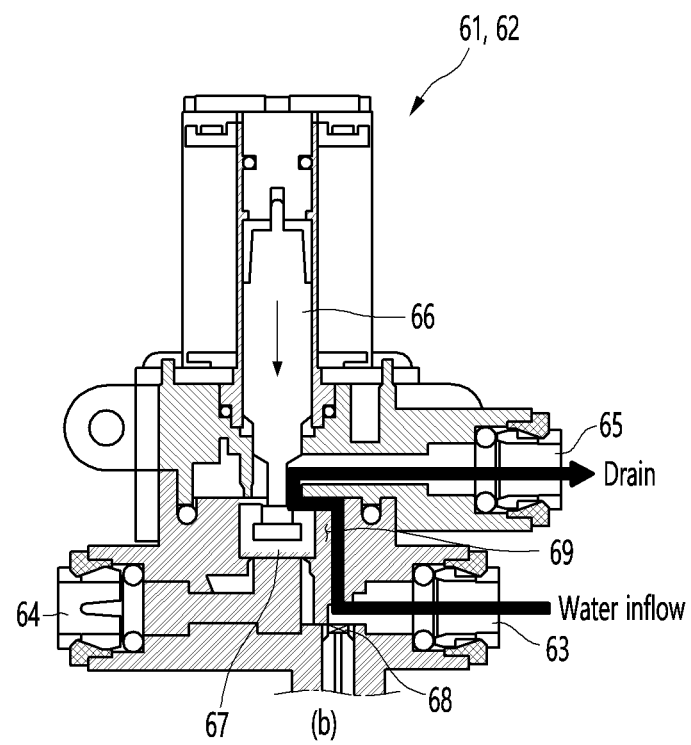
(b)

LIQUID DISPENSING DEVICE

CROSS-REFERENCE TO RELATED APPLICATION

This application claims priority under 35 U.S.C. § 119 to Korean Application No. 10-2019-0021252 filed on Feb. 22, 2019, whose entire disclosure is hereby incorporated by reference. This application is also related to U.S. application Ser. No. 16/796,014 filed Feb. 20, 2020, and U.S. application Ser. No. 16/796,144 filed Feb. 20, 2020, the entire contents of which are hereby incorporated by reference. Further, one of ordinary skill in the art will recognize that features disclosed in these above-noted applications may be combined in any combination with features disclosed herein.

BACKGROUND

1. Field

The present disclosure relates to a liquid (e.g., water) dispensing device.

2. Background

In general, liquid dispensing apparatuses are apparatuses for supplying water or other liquids, for example, apparatuses for dispensing various amounts of water through user's manipulation. In such a liquid dispensing apparatus, when the user normally operates a lever, a button, or other input device, stored liquid is dispensed through a nozzle. In detail, in the liquid dispensing apparatus, while the user manipulates the lever or the button, the nozzle is opened to dispense liquid. Then, the user stops the manipulation of the lever or the button while the user confirms an amount of liquid filled into a cup or a container.

The liquid dispensing apparatus may be applied to various fields. Representatively, the liquid dispensing apparatus may be applied to a refrigerator and a liquid purifier. For example, the liquid dispensing apparatus provided in the refrigerator and the liquid purifier may have a function of supplying an amount of liquid, which is automatically set by the user's manipulation. In recent years, liquid dispensing apparatuses capable of supplying not only purified liquid but also cold liquid and hot liquid have been developed.

An 'under sink type drinking water supply device' is disclosed in Korean Patent Registration No. 1884736. This document 1 has a feature of a discharge part provided with a main body installed below a sink and a nozzle part installed outside the sink to discharge water. Also, a manipulation panel for function selection is separably provided at an upper side of the nozzle part, a container support part foldably or rotatably connected to a display part is additionally provided, and remaining water within a tube is automatically drained. In this device, although purified water, cold water, and hot water are supplied through the nozzle part exposed to the outside of the sink, there is a disadvantage in that this device does not supply sterilized water (also referred to herein as a "sterilizing liquid") for cleaning. In addition, a specific coupling structure between the discharge part and the body part is not disclosed.

A purified water and sterilized water supply device is disclosed in Korean Patent Publication No. 10-2014-0033772. This document discusses a supply part which supplies purified water and sterilized water generated by a purified water generation part and sterilized water generation part to the outside. Also, the supply part includes a supply cock that supplies purified or sterilized water to the sink and a manipulation part installed on cock. As the sterilized water and the purified water are discharged through one cock, when the purified water is discharged, the sterilized water remaining in the tube and the cock is mixed with the purified water and then discharged. For reference, since the sterilized water may contain hypochlorous acid (HClO) and the like, the sterilized water is not suitable for drinking water. Therefore, it is necessary to discharge the purified water and the sterilized water through separate cocks.

In addition, since all of electrodes are flat, a volume of the sterilized water generation device that generates the sterilized water increases to occupy a lot of installation space. Thus, it is difficult to simply additionally install the sterilized water generation device inside the water purifier or water treatment device according to the related art. Also, when the sterilized water remains in the tube, the valve, and the cock, precipitation occurs in the tube, the valve, and the cock, such that erosion of the tube, the valve, and the cock may occur.

The above references are incorporated by reference herein where appropriate for appropriate teachings of additional or alternative details, features and/or technical background.

BRIEF DESCRIPTION OF THE DRAWINGS

The embodiments will be described in detail with reference to the following drawings in which like reference numerals refer to like elements wherein:

FIG. 4 is an exploded perspective view of the liquid discharge part that is the main component according to an embodiment.

FIG. 7C is a schematic view having partial cross-hatching added for clarity and illustrating an example of operations of a first liquid discharge valve and a second liquid discharge valve.

DETAILED DESCRIPTION

Figure 1:
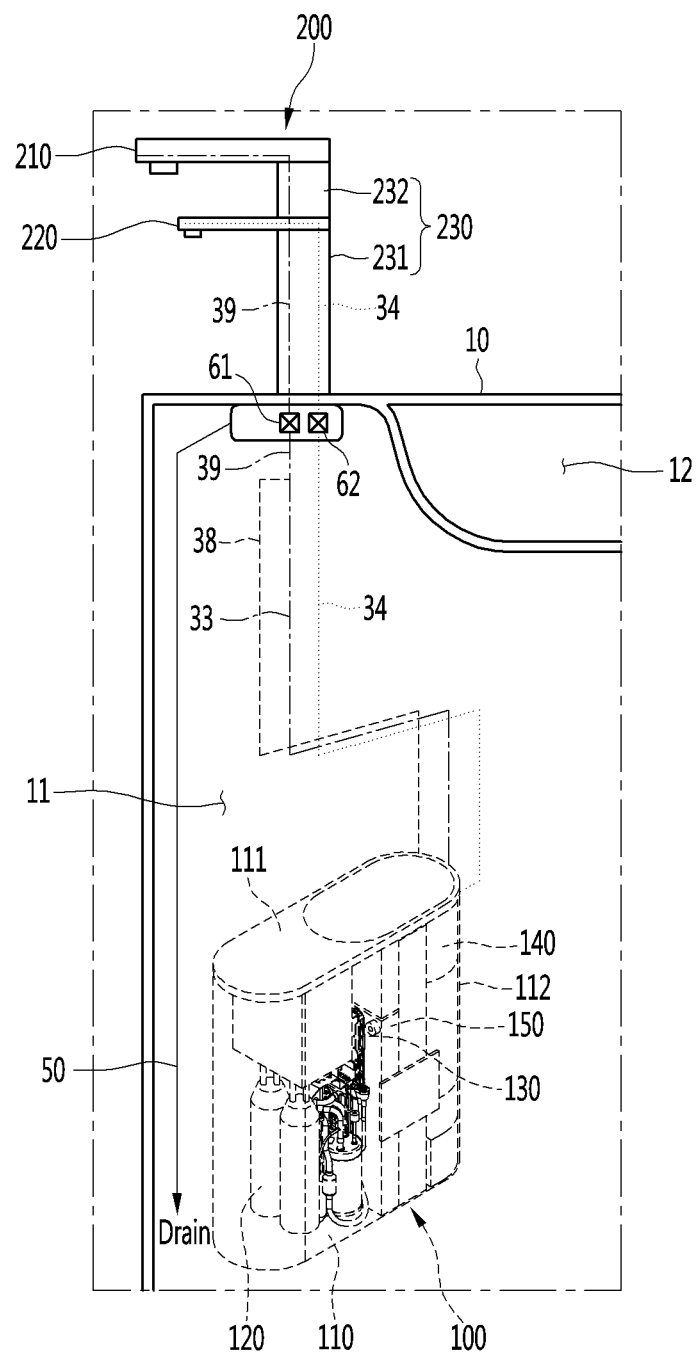
FIG. 1 is a view illustrating a state in which a liquid dispensing device is mounted in a sink according to an embodiment.

FIG. 1 is a view illustrating a state in which a liquid dispensing device is mounted in a sink 10 according to an embodiment. Also, FIG. 2 is a view illustrating tubes of the liquid dispensing device according to an embodiment.

A liquid dispensing device according to an embodiment may include various liquid treatment devices and purification devices, into which liquid is introduced from the outside, such as a liquid purifier, a refrigerator, etc., to purify the introduced liquid and then discharge the liquid. For example, the liquid dispensing device according to an embodiment may be provided with an under sink type liquid purifier of which at least a portion is disposed in a lower space of a sink 10.

Figure 2:
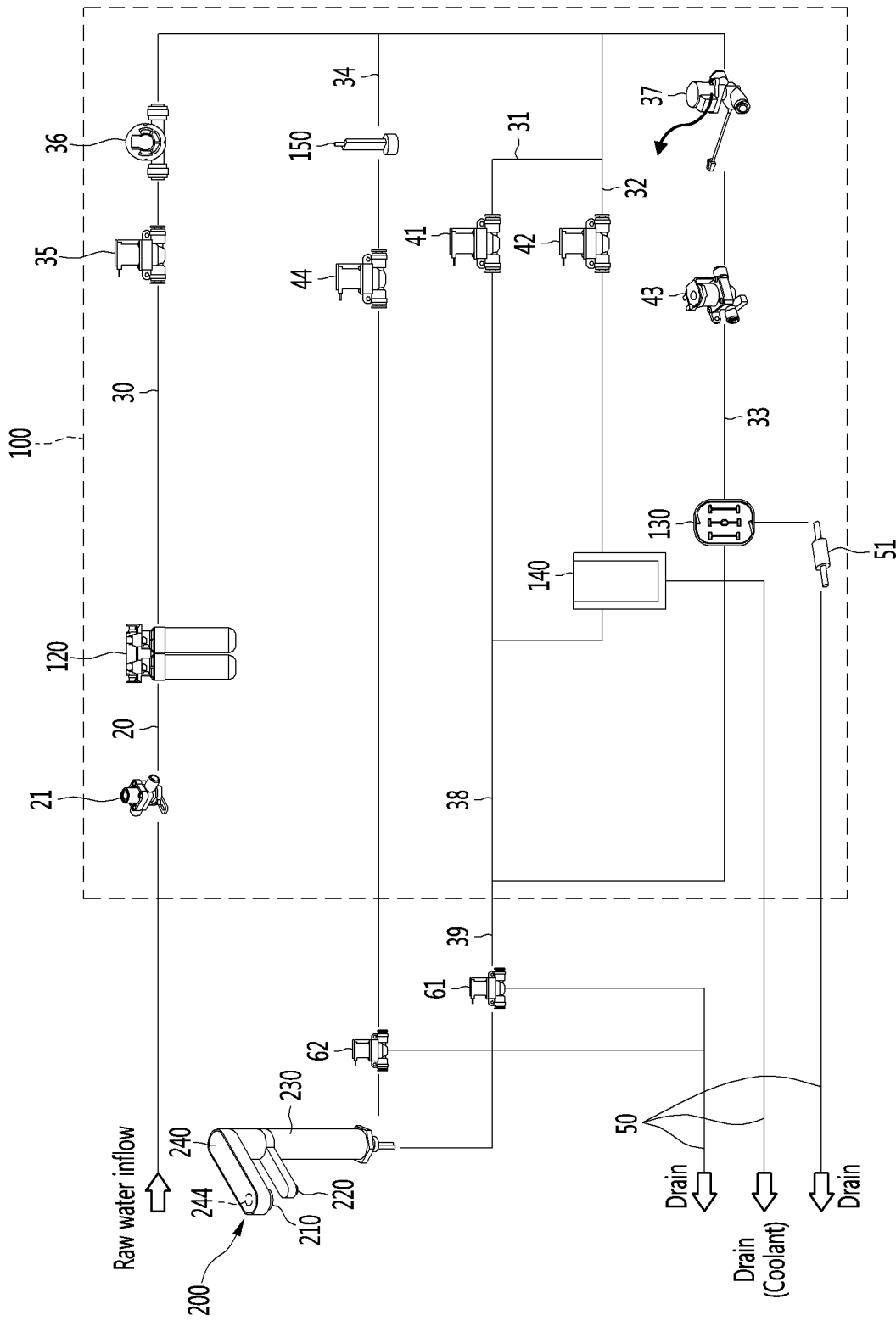
FIG. 2 is a view illustrating tubes of the liquid dispensing device according to an embodiment.

Referring to FIGS. 1 to 2, the liquid dispensing device according to an embodiment includes a body part (or liquid processing module) 100 installed inside the sink 10 and a liquid discharge part (or liquid dispenser) 200 of which at least a portion is installed to be exposed to the outside of the sink 10. First, the body part 100 includes a housing 110 defining an outer appearance thereof. The housing 110 includes a top cover 111 having a planar shape defining a top surface thereof. Also, the housing 110 may have front and rear surfaces that are convex in front and rear directions, respectively. Also, each of both side surfaces and a bottom surface connecting the front surface to the rear surface may be flat.

The housing 110 may be provided in a box shape and may be positioned in an accommodation space 11 provided below the sink 10. The housing 110 may be provided in a slim form having a narrow left and right width and a long front and rear length. Thus, the housing 110 may be positioned in a left and right direction or a front and rear direction inside the sink and also be positioned at an inner corner of the inner space of the sink to improve space utilization. Also, the front surface of the housing 110 may be separated. When the front surface of the housing 110 is separated, a filter is exposed, and a user may easily replace the filter exposed to the outside.

Also, the liquid dispensing device according to an embodiment may include a raw liquid tube 20 that guides raw liquid supplied from the outside of the housing 110 into the housing 110, a filter 120 that purifies the liquid supplied along the raw liquid tube 20, and a liquid discharge tube 30 through which the purified liquid passing through the filter 120 flows toward the liquid discharge part 200.

The raw liquid tube 20 passes through the housing 110 to connect an external liquid supply source to the filter 120 inside the housing 110. The raw liquid supplied from the liquid supply source outside the housing 110 may be supplied to the filter 120 through the raw liquid tube 20.

The liquid (the raw liquid) supplied to the filter 120 as described above is purified into purified liquid while passing through the filter 120. At least one filter 120 may be provided. For example, three or more filters 120 may be provided. Thus, the liquid passing through the raw liquid tube 20 may be purified into cleaner liquid while passing through the plurality of filters 120.

Also, the purified liquid passing through the filter 120 may flow to the liquid discharge part (or dispenser) 200 exposed to the outside of the sink 10 through the liquid discharge tube 30. For this, one end of the liquid discharge tube 30 is connected to the filter 120, and the other end of the liquid discharge tube 30 passes through the housing 110 and then is exposed to the outside of the housing 110 and connected to the liquid discharge part 200. Here, the liquid discharge tube 30 may pass through a rear end (e.g., a right side in FIG. 1) of the housing 110. Also, the liquid discharge tube 30 may include a sterilized liquid tube 34, common tubes 38 and 39, and a hot liquid tube 33, which will be described later. When the liquid discharge tube 30 passes through the rear end of the housing 110 as described above, since the liquid discharge tube 30 does not pass through the top cover 111 defining the top surface of the housing 110, the top cover 111 may be easily assembly and disassembled.

As described above, to allow the liquid discharge tube 30 to pass through the rear end of the housing 110, a recess having a shape that is concave downward in a center of an upper end of the rear cover 112 defining the rear of the housing 110. Also, at least one section of the liquid discharge tube 30, i.e., the sterilized liquid tube 34, the common tubes 38 and 39, and the hot liquid tube 33 to be described later may get out from the inside to the outside of the housing 10 through the recess. An opened upper side of the recess may be covered by the top cover 111. Thus, when the top cover 111 is separated from the housing 110, the upper side of the recess is opened, and when the top cover 111 is mounted on the housing 110, the upper side of the recess is covered so that the recess defines a closed space. Also, the liquid discharge tube 30 passing through the recess may be fixed by the recess and the top cover 111.

Also, the other end of the liquid discharge tube 30 exposed to the outside of the housing 110 may be directly connected to the liquid discharge part 200 or may be connected to the liquid discharge part 200 through a separate connection tube or a connection component. In the latter case, one end of the connection tube or the connection component may be connected to the liquid discharge tube 30, and the other end thereof may be connected to the liquid discharge part 200. Here, the liquid discharged to the outside of the housing 110 through the liquid discharge tube 30 may be supplied to the liquid discharge part 200 through the connection tube.

As described above, the liquid discharge tube 30 may include at least one of a purified liquid tube 31, a cold liquid tube 32, a hot liquid tube 33, or the sterilized liquid tube 34. That is, in the following description, the purified liquid tube 31, the cold liquid tube 32, the hot liquid tube 33, and the sterilized liquid tube 34 may be understood to be included in the liquid discharge tube 30. Also, it will be understood that the common tubes 38 and 39 described below may also be included in the liquid discharge tube 30. In the following description, the liquid discharge tube 30 may be understood to include all of the purified liquid tube 31, cold liquid tube 32, hot liquid tube 33, sterilized liquid tube 34, and the common tube 38 and 39.

One end of the liquid discharge tube 30 is connected to the filter 120, and the liquid passing through the filter 120 flows to the liquid discharge part 200 through the liquid discharge tube 30. Also, the other end of the liquid discharge tube 30 may be branched into the purified liquid tube 31, the cold liquid tube 32, the hot liquid tube 33, and the sterilized liquid tube 34 inside the housing 110.

In the liquid discharge tube 30, the liquid branched to the purified liquid tube 31 is directly supplied to the liquid discharge part 200 in the purified state. On the other hand, in the liquid discharge tube 30, the liquid branched to the cold liquid tube 32 is cooled while passing through the cold liquid tank 140 provided on the cold liquid tube 32 and then is supplied to the liquid discharge part 200 in the state of the cold liquid. Also, the liquid branched to the hot liquid tube 33 is heated through a hot liquid tank 130 provided on the hot liquid tube 33 and is supplied to the liquid discharge part 200 in the state of the hot liquid. Also, the liquid branched into the sterilized liquid tube 34 may be supplied to the liquid discharge part 200 as the sterilized liquid while passing through the sterilized liquid module 150 provided on the sterilized liquid tube 34.

A decompression valve 21 that adjusts a flow rate of the liquid supplied to the filter 120 may be installed in the raw liquid tube 20. Also, at least one of a flow sensor 36 that detects a flow rate of liquid, an inflow valve 35 that adjusts the flow rate of the liquid or controls a flow of the liquid, a flow rate sensor that detects the flow rate of the liquid may be installed in the raw liquid tube 20 or the liquid discharge tube 30. Also, a switching valve that controls the flow of the liquid in each of the tubes may be separately installed in the purified liquid tube 31, the cold liquid tube 32, the hot liquid tube 33, and the sterilized liquid tube 34, which are branched from the liquid discharge tube 30. In detail, the purified liquid tube 31 may be provided with a purified liquid valve 41 to control the flow of the liquid in the purified liquid tube 31. Also, the cold liquid tube 32 may be provided with a cold liquid valve 42 to control the flow of liquid in the cold liquid tube 32. Also, the hot liquid tube 33 may be provided with a hot liquid valve 43 to control the flow of liquid in the hot liquid tube 33. Also, the sterilized liquid tube 34 may be provided with a sterilized liquid valve 44 to control the flow of liquid in the sterilized liquid tube 34. Also, the hot liquid tube 33 may be provided with a flow rate control valve 37 that adjusts an amount of liquid flowing into the hot liquid tank 130. Also, a safety valve 51 that discharges steam may be installed in the hot liquid tank 130.

If the flow sensor 36 is provided as described above, an amount of liquid supplied to the cold liquid tank 140 and the hot liquid tank 130 may be detected to control an output supplied to the cold liquid tank 140 and hot liquid 130 by utilizing the flow rate information. Also, when the flow rate control valve 37 is provided, an amount of liquid supplied to the hot liquid tank 130 may be adjusted to generate hot liquid having a temperature desired by the user.

In addition, when the purified liquid valve 41, the cold liquid valve 42, the hot liquid valve 43, and the sterilized valve 44 are provided in the purified liquid tube 31, the cold liquid tube 32, the hot liquid tube 33, and the sterilized liquid tube 34, respectively, the flow of the liquid supplied to the cold liquid tank 140, the hot liquid tank 130, and the sterilized liquid module 150 may be controlled. The cold liquid valve 42, the hot liquid valve 43, and the sterilized liquid valve 44 may be opened only when the cold liquid, the hot liquid, or the sterilized liquid need to be generated, thereby supplying the liquid to the cold liquid tank 140, the hot liquid tank 130, and the sterilized liquid module 150. In the case of the purified liquid valve 41, the purified liquid valve 41 may be opened only when the discharge of the purified liquid is required, thereby supplying the purified liquid to the liquid discharge part 200.

The liquid discharge part 200 includes a plurality of liquid discharge nozzles 210 and 220 that supply the purified liquid, the cold liquid, the hot liquid, and the sterilized liquid supplied from the purified liquid tube 31, the cold liquid tube 32, the hot liquid tube 33, and the sterilized liquid tube 34 to the user. The plurality of liquid discharge nozzles 210 and 220 may extend in a horizontal direction from a body part 230 extending in a vertical direction so as to be exposed to an upper side of the sink 10. The liquid discharge nozzles 210 and 220 may include a first liquid discharge nozzle 210 through which the purified liquid, the cold liquid, and the hot liquid are discharged and a second liquid discharge nozzle 220 through which the sterilized liquid is discharged. For example, the first liquid discharge nozzle 210 and the second liquid discharge nozzle 220 may be spaced apart from each other in the vertical direction. Here, the first liquid discharge nozzle 210 may be positioned at an upper side, and the second liquid discharge nozzle 220 may be positioned at a lower side.

Thus, contamination of the first liquid discharge nozzle 210 by the sterilized liquid while the sterilized liquid discharged from the second liquid discharge nozzle may be prevented. Also, as the first liquid discharge nozzle 210 which is relatively frequently used to discharge the cold, hot, and purified liquid may be positioned at the upper side, the user may easily access and manipulate the first liquid discharge nozzle, and the liquid is easily discharged. Also, as the second liquid discharge nozzle 220 which is used relatively less is positioned below the first liquid discharge nozzle 210, the second liquid discharge nozzle 220 may be possible to conceal and is relatively difficult to access compared to the first liquid discharge nozzle 210, thereby preventing the sterilized liquid from being discharged accidentally.

For another example, the first liquid discharge nozzle 210 and the second liquid discharge nozzle 220 may be spaced apart from each other in the horizontal direction. The first liquid discharge nozzle 210 and the second liquid discharge nozzle 220 may be rotatably mounted based on the body part 230. The first liquid discharge nozzle 210 and the second liquid discharge nozzle 220 may independently rotate.

The purified liquid and the cold liquid, which flow along the purified liquid tube 31 and the cold liquid tube 32, are combined in one first common tube 38 and supplied to the liquid discharge part 200 through the first common tube 38. Thus, the purified liquid, the cold liquid, and the hot liquid, which flow through the first common tube 38 and the hot liquid tube 33, are supplied to the user through the first liquid discharge nozzle 210.

Also, the hot liquid tube 33 may also be combined with the first common tube 38. The second common tube 39 may connect the liquid discharge part 200 from a point at which the hot liquid tube 33 and the first common tube 38 are coupled. In this case, the purified liquid, the cold liquid, and the hot liquid flowing through the second common tube 39 may be supplied to the user through the first liquid discharge nozzle 210. Also, the sterilized liquid generated by the sterilized liquid module 150 may be supplied to the user outside the sink 10 through the second liquid discharge nozzle 220 after flowing through the sterilized liquid tube 34.

The second liquid discharge valve 62 may be installed on the sterilized liquid tube 34. The second liquid discharge valve 62 may be installed between the sterilized liquid tube 34 and the liquid discharge part 200. The second liquid discharge valve 62 may supply the sterilized liquid flowing to the liquid discharge part 200 through the sterilized liquid tube 34 to the liquid discharge part 200 or may be discharged to a separate drain tube 50.

Also, a first liquid discharge valve 61 may be installed on the second common tube 39. The first liquid discharge valve 61 may be installed between the second common tube 39 and the liquid discharge part 200. The first liquid discharge valve 61 may supply the purified liquid, the cold liquid, and the hot liquid, through the second common tube 39, to the liquid discharge part 200 or may discharge the purified liquid, the cold liquid, and the hot liquid to a separate drain tube 50.

For example, each of the first liquid discharge valve 61 and the second liquid discharge valve 62 may be provided as a 3-way valve that has one inlet, first and second outlets, which are selectively opened, and an actuator that selectively opens and closes the two outlets. Here, the first outlet may be connected to the liquid discharge nozzles 210 and 220, and the second outlet may be connected to the drain tube 50. In detail, the inlet of the first liquid discharge valve 61 is connected to the second common tube 39, the first outlet is connected to the first liquid discharge nozzle 210, and the second outlet is connected to the drain tube 50.

Also, the inlet of the second liquid discharge valve 62 is connected to the sterilized liquid tube 34, the first outlet is connected to the second liquid discharge nozzle 220, and the second outlet is connected to the drain tube 50. For reference, the drain tube connected to the first liquid discharge valve 61 and the drain tube connected to the second liquid discharge valve 62 may be provided separately and also use one drain tube in common.

As shown in FIG. 1, the liquid discharge part 200 may be mounted to the sink 10 so that at least a portion thereof is exposed to an upper side of the sink 10. Thus, the body part 230 and the first and second liquid discharge nozzles 210 and 220 extending to one side of the body part 230 may be exposed to the outside while being positioned on the upper portion the sink 10.

Thus, according to this embodiment, the liquid discharge nozzle may be provided so that the cold, hot, purified liquid and the sterilized liquid are respectively discharged through the liquid discharge parts.

Even if the liquid discharge part 200 is configured so that the purified liquid, the cold liquid, the hot liquid, and the sterilized liquid are discharged to the outside of the sink, when the liquid discharge nozzle is positioned so that the purified liquid, the cold liquid, the hot liquid, and the sterilized liquid are not discharged from the same point, the user first may primarily clean germs and dirt on the surface of vegetables and fruits under the sterilized liquid discharge nozzle and then transfer the vegetables, the fruits, etc., that are cleaned with sterile liquid below the liquid discharge nozzle. The purified liquid may be discharged to secondly clean and remove the sterile liquid attached to the vegetable fruit. Thus, as the first cleaning and the second cleaning are performed at different places, the cleaning process may be very cumbersome.

However, in this embodiment, an object to be cleaned may be positioned at one position, and the sterilized liquid may be discharged through the second liquid discharge nozzle 220 to primarily clean the object, and then, the purified liquid may be discharged through the first liquid discharge nozzle 201 positioned above the second liquid discharge nozzle 220 to clean the sterilized liquid. Thus, while the first cleaning and the second cleaning are performed at one place, the cleaning process may be relatively simple.

Also, liquid mainly used by the user may be the purified liquid, the hot liquid, or the cold liquid. The sterile liquid may only be discharged under special circumstances. Thus, in this embodiment, the first discharge nozzle 210 is positioned above the second discharge nozzle 220 so that the user selects the discharging of the purified liquid instead of the discharging of the sterilized liquid in the unconscious state.

In general, when discharging the sterilized liquid for drinking, hypochlorite (or other sterilizer) contained in the sterilized liquid may not be beneficial to the user's health.

Thus, in this embodiment, the first discharge nozzle 210 capable of discharging the cold, hot, and purified liquid is positioned at the upper side of the cylindrical body part 230, and the second discharge nozzle 220, in which sterilized liquid is discharged, is positioned at the lower side Also, as illustrated in the drawings, the width and the extended length of the first liquid discharge nozzle 210 through which the purified liquid, the hot liquid, and the cold liquid are discharged are wider and longer than those of the second liquid discharge nozzle 220 through which the sterilized liquid is discharged. Thus, the second liquid discharge nozzle 220 through which the sterilized liquid is discharged is concealed by the first liquid discharge nozzle 210.

In this embodiment, the upper liquid discharge nozzle and the lower liquid discharge nozzle have a structure that is capable of rotating separately. If the upper liquid discharge nozzle and the lower liquid discharge nozzle do not rotate independently but have a structure that rotates at the same time, when the purified, hot, and cold liquid are discharged from the upper liquid discharge nozzle, the lower liquid discharge nozzle may interfere with a container receiving the liquid. Thus, the two liquid discharge nozzles are positioned in the cylindrical body part (or outer cylinder) 230 defining an outer appearance and have a structure capable of rotating at a predetermined angle with respect to the cylindrical internal member (or cylinder body) 260. The first liquid discharge nozzle 210 and the second liquid discharge nozzle 220 may be designed to rotate about 180 degrees.

Also, in this embodiment, to prevent the two liquid nozzles 210 and 220 that rotate independently from moving arbitrarily by external interference, a plurality of O-rings and square rings may be positioned between a stationary body and a rotating body. For reference, the 'rotating body' may mean the first liquid discharge nozzle 210 and the second liquid discharge nozzle 220. Also, the 'stationary body' may mean the body part 230, the internal member 260 to be described later, first and second connection members 214 and 215 and a coupling member 216, which will be described later.

Each of the O-rings and square rings is made of a material having elasticity such as rubber or a soft plastic. Also, the first liquid discharge nozzle 210 and the second liquid discharge nozzle 220 may be fixed at a position set by the user through an action of the O-rings and the square rings. In particular, in the case of the O-ring, friction is generated in the circumferential direction, and in the case of square rings, a predetermined height is defined, and friction is generated in the vertical direction. Thus, in the case of the first liquid discharge nozzle 210 and the second liquid discharge nozzle 220, the shaking in the circumferential direction and the vertical direction (axial direction) may be prevented by the O-ring and the square ring. Also, the O-ring and the square ring may prevent the components from separating. As the friction occurs by the O-ring and the square ring, while the rotation of the first liquid discharge nozzle 210 and the second liquid discharge nozzle 220 are performed smoothly, the manipulation feeling may be improved, and the first liquid discharge nozzle 210 and the second liquid discharge nozzle 220 may be fixed to the rotating position.

Also, the liquid discharge part 200 may be provided with a display and input part (or user interface device) 240. For example, the display and input part 240 may be a touch screen. The display and input part 240 may include a liquid discharge button 244, an input part that inputs various commands and settings, and a display part displays various states to the outside.

For example, the display and input part 240 may be positioned on a top surface of the first liquid discharge nozzle 210. Therefore, the display and input part 240 may be positioned at the uppermost side of the liquid discharge part 200. Also, the display and input part 240 may perform a hot, purified, cold, sterilized liquid selection function, a liquid discharge command function, a cold and hot liquid temperature setting and display function, a drain selection function, a filter replacement cycle notification function, a function of setting capacity of liquid discharged, a function of setting a discharge time of the liquid discharged.

Also, the sterilized liquid selection button and the sterilized liquid discharge button may also be provided on the upper side of the first liquid discharge nozzle 210 so that the user may recognize the type of liquid discharged. The liquid discharge button 244 may be positioned on a vertical upper portion of a first cock 219 to be described later. That is, the liquid discharge button 244 may be positioned at a position overlapping the first cock 219 in the vertical direction.

Hereinafter, a process of discharging the purified liquid, the cold liquid, the hot liquid, and the sterilized liquid in the liquid dispensing device according to an embodiment will be described with reference to FIGS. 1 to 2. The body part 100 receives the raw liquid through the raw liquid tube 20 connected to the liquid supply source such as a liquid tube, a liquid tank, and an underground liquid tube. A decompression valve 21 is installed on the raw liquid tube 20, and the raw liquid is reduced in pressure at a predetermined pressure while passing through the decompression valve 21.

Then, the decompressed raw liquid flows to the filter 120 through a tube connecting the decompression valve 21 to the filter 120. Foreign substances are removed from the raw liquid passing through the filter 120, and thus, the raw liquid is changed into purified liquid. Then, the purified liquid passing through the filter 120 passes through the flow sensor 36 while flowing along the liquid discharge tube 30 by opening the inflow valve 35. In this case, a flow rate detected by the flow sensor 36 may be used as data that is used for controlling an output of the hot liquid tank 130 or the cold liquid tank 140.

The purified liquid passing through the flow sensor 36 flows along the liquid discharge tube 30. Also, the purified liquid may be branched to be converted to the sterilized liquid, the cold liquid-purified liquid, and the hot liquid. First, the purified liquid branched to the cold liquid-purified liquid is again branched to the cold liquid and the purified liquid to flow to the purified liquid tube 31 and the cold liquid tube 32, respectively. Each of the purified liquid tube 31 and the cold liquid tube 32 is provided with a purified liquid valve 41 and a cold liquid valve 42 to control the flow of the liquid, respectively. The purified liquid valve 41 and the cold liquid valve 42 may be selected by a user's purified liquid or cold liquid selection operation, and the selected valve is opened by operating the liquid discharge button by the user so that the purified liquid or cold liquid is supplied to the user through the first discharge nozzle 210.

In detail, when the user requests the discharging of the cold liquid discharge, the cold liquid valve 42 is opened. When the cold liquid valve 42 is opened as described above, the purified liquid of the liquid discharge tube 30 passes through the cold liquid tube 32 and the cold liquid valve 42, and the liquid in the cold liquid tube 32 passes through a cooling coil inside the cold liquid tank 140. The liquid flowing along the cooling coil is heat-exchanged with a coolant within the cold liquid tank 140 and then cooled. For this, the coolant is continuously cooled to maintain a set temperature.

The cold liquid passing through the cold liquid tank 140 may flow to the liquid discharge part 200 through a first common passage 38 and a second common passage 39 connected to the cold liquid tube 32 and may be supplied to the first liquid discharge nozzle 210 via the first liquid discharge valve 61. For reference, a compressor may be driven to cool the coolant. The driving of the compressor may be determined by a cold liquid temperature sensor provided in the cold liquid tank 140. Thus, the coolant may be always maintained at the preset temperature. For this, the driving of the compressor may be controlled. The compressor may be adjusted in frequency to correspond to a load that is required for an inverter compressor and thus adjusted in cooling capacity. That is, the compressor may be driven by an inverter control to cool the coolant with optimal efficiency.

When the user requests the discharging of the purified liquid, the purified liquid valve 41 is opened. When the purified liquid valve 41 is opened as described above, the purified liquid of the liquid discharge tube 30 passes through the purified liquid tube 31 and the purified liquid valve 41 to flow to the liquid discharge part 200 through the first and second common passages 38 and 39 connected to the purified liquid tube 31. The purified liquid may be supplied to the first liquid discharge nozzle 210 via the first liquid discharge valve 61.

When the user requests the discharging of the hot liquid, the hot liquid valve 43 is opened. When the hot liquid valve 43 is opened as described above, the purified liquid of the liquid discharge tube 30 passes through the hot liquid tube 33 and the hot liquid valve 43. Also, the liquid passing through the hot liquid tube 33 may be adjusted in flow rate by the flow rate control valve 37. While passing through the flow control valve 37 as described above, the purified liquid that is adjusted in flow rate passes through the hot liquid tank 130. Also, while passing through the hot liquid tank 130, the liquid may be heated at the set temperature. The hot liquid tank 130 may be heated by an induction heating method. For this, an output of a working coil provided in the hot liquid tank 130 may be adjusted. Also, the purified liquid passing through the hot liquid tank 130 may be heated at the set temperature.

The hot liquid heated while passing through the hot liquid tank 130 flows to the liquid discharge part 200 through the second common passage 39 connected to the hot liquid tube 33. The purified liquid may be supplied to the first liquid discharge nozzle 210 via the first liquid discharge valve 61.

Also, the hot liquid tank 130 may be further connected to the drain tube 50. The drain tube 50 may discharge steam generated when the liquid within the hot liquid tank 130 is evaporated. Also, a safety valve 51 is provided in the drain tube 50. When an internal pressure is equal to or greater than a set pressure, the safety valve 51 is opened to discharge steam.

In detail, the safety valve 51 is configured to discharge the steam generated when the hot liquid is heated in the hot liquid tank. Thus, the safety valve 51 prevents the inside of the hot liquid tank from excessively increasing in pressure by the steam. The safety valve 51 may be configured to be opened at the set pressure and have various structures as long as the steam generated in the hot liquid tank is smoothly discharged.

In the case of the drain tube for discharging the steam, the drain tube may be provided separately with respect to the drain tube connected to the first liquid discharge valve 61 and the second liquid discharge valve 62. Also, in the case of the drain tube for discharging the steam, the drain tube may be combined to the drain tube connected to the first liquid discharge valve 61 and the second liquid discharge valve 62.

For reference, the hot liquid tank 130 may generate instantaneous hot liquid in an induction heating method. Also, when the flow rate of the liquid flowing into the hot liquid tank 130 is less due to the instantaneous hot liquid, boiling may occur in the hot liquid tank 130. In the case of this embodiment, to prevent this phenomenon from occurring, a temperature sensor is mounted on a heat sink of an element (e.g., IGBT) provided in a control module for supplying output to the hot liquid tank. When the temperature of the heat sink exceeds the set temperature (for example, about 70° C.), output supply to the hot liquid tank 130 is stopped.

For example, the hot liquid tank 130 may include an induction heating assembly that generates the hot liquid and a controller that controls driving of the induction heating assembly and the valve. The induction heating assembly and the controller may be coupled to each other in a single module state and may be mounted inside the housing 110 in the coupled state. The induction heating assembly is configured to receive the purified liquid supplied to the hot liquid tank 130 so as to be heated by hot liquid in an induction heating (IH) manner. The induction heating assembly may include the walking coil that heats liquid passing through the hot liquid tank 130.

In the case of the liquid dispensing device according to an embodiment as described above, the cold liquid, the purified liquid, and the hot liquid may be discharged to the outside through one first liquid discharge nozzle 210. For reference, the first liquid discharge valve 61 is provided with a temperature sensor 68 (see FIG. 7B) that measures temperatures of the cold liquid and the hot liquid, which are supplied through the second common tube 39. The temperature sensor detects temperatures of the cold liquid and the hot liquid, which are supplied to the second common tube 39. Also, when the temperature detected by the temperature sensor is included in the preset satisfaction range, the first liquid discharge valve 61 may supply the cold liquid and the hot liquid to the first liquid discharge nozzle 210, and when the detected temperature is not included in the preset satisfaction range, the purified liquid, the cold liquid, and the hot liquid may be discharged to the drain tube 50.

The temperature sensor 68 (see FIG. 7B) may be installed on the passage of the first liquid discharge valve 61. In detail, the temperature sensor 68 (see FIG. 7B) may be installed to be exposed toward the inflow part into which the cold/hot liquid are introduced.

Also, when the hot liquid and cold liquid are discharged, if the user presses the liquid discharge button, the liquid in the tube may be drained unconditionally regardless of whether the temperature is satisfied, and the hot and cold liquid may be discharged. In detail, when the user requests the discharging of the cold liquid, the liquid (remaining liquid) filled between the cold liquid tank 140 and the first discharge valve 61 is automatically drained through the drain tube 50, and the discharging of the remaining liquid is performed. Thereafter, the liquid of the cold liquid tank 140 may be supplied to the first discharge nozzle 210 via the first discharge valve 61. Thus, only the cool cold liquid may be supplied to the user.

Also, when the user requests the discharging of the hot liquid, the liquid (remaining liquid) filled between the hot liquid tank 130 and the first liquid discharge valve 61 is automatically drained through the drain tube 50, and the discharge of the remaining liquid is performed. Thereafter, the liquid of the hot liquid tank 130 may be supplied to the first discharge nozzle 210 via the first discharge valve 61. Therefore, only the hot liquid may be supplied to the user. In the case of the purified liquid, the discharging of the purified liquid may be performed immediately without draining the remaining liquid.

When the user requests the discharging of the sterilized liquid, the sterilized liquid valve 44 is opened. When the sterilized liquid valve 44 is opened as described above, the purified liquid of the liquid discharge tube 30 passes through the sterilized liquid tube 34 and the sterilized liquid valve 44, and the liquid of the sterilized liquid tube 34 passes through the sterilized liquid module 150. The sterilized liquid generated by the sterilized liquid module 150 flows along the sterilized liquid tube 34 toward the liquid discharge part 200 and then is supplied to the outside through the second liquid discharge nozzle 220 via the second liquid discharge valve 62.

Due to a distance between the body part 100 installed inside the sink and the liquid discharge part 200 installed outside the sink, the passage connecting the body part 110 to the liquid discharge part 200 may have a long length. Also, since the remaining liquid remaining in the passage affects the discharge liquid temperature, the valves 61 and 62 are installed at positions as close as possible to the liquid discharge part 200 to selectively drain the remaining liquid remaining in the passage, thereby improving temperature performance.

That is, according to an embodiment, the remaining liquid remaining in the passage having the long length, which connects the body part 100 to the liquid discharge part 200, after the discharging may be drained in the valve 61 installed directly below the liquid discharge part 200, and then, the produced direct liquid (hot liquid or purified liquid) may be discharged to the liquid discharge nozzle 210 to satisfy a target liquid discharge temperature.

Figure 3:
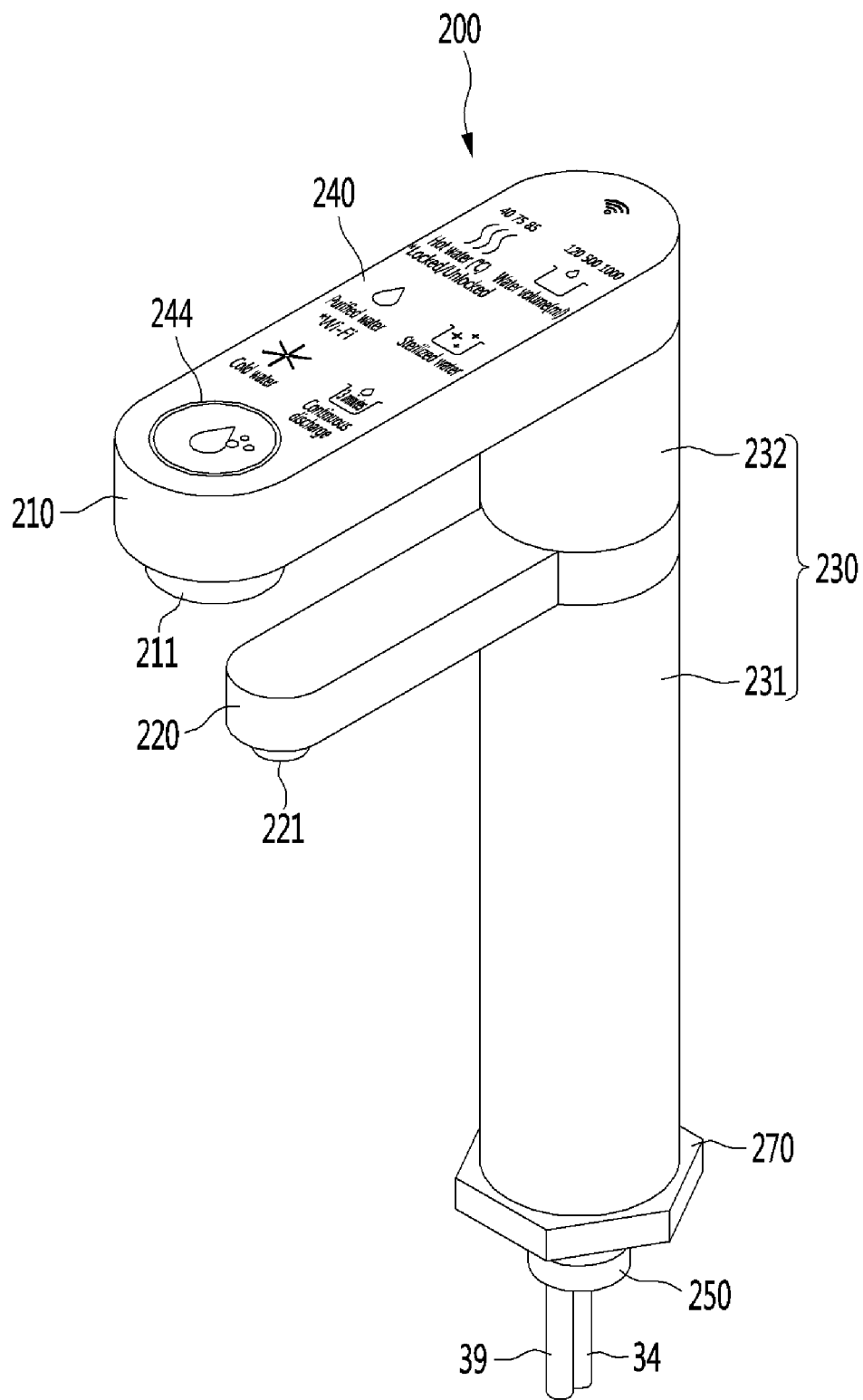
FIG. 3 is a perspective view of a liquid discharge part that is a main component according to an embodiment.
Figure 5A:
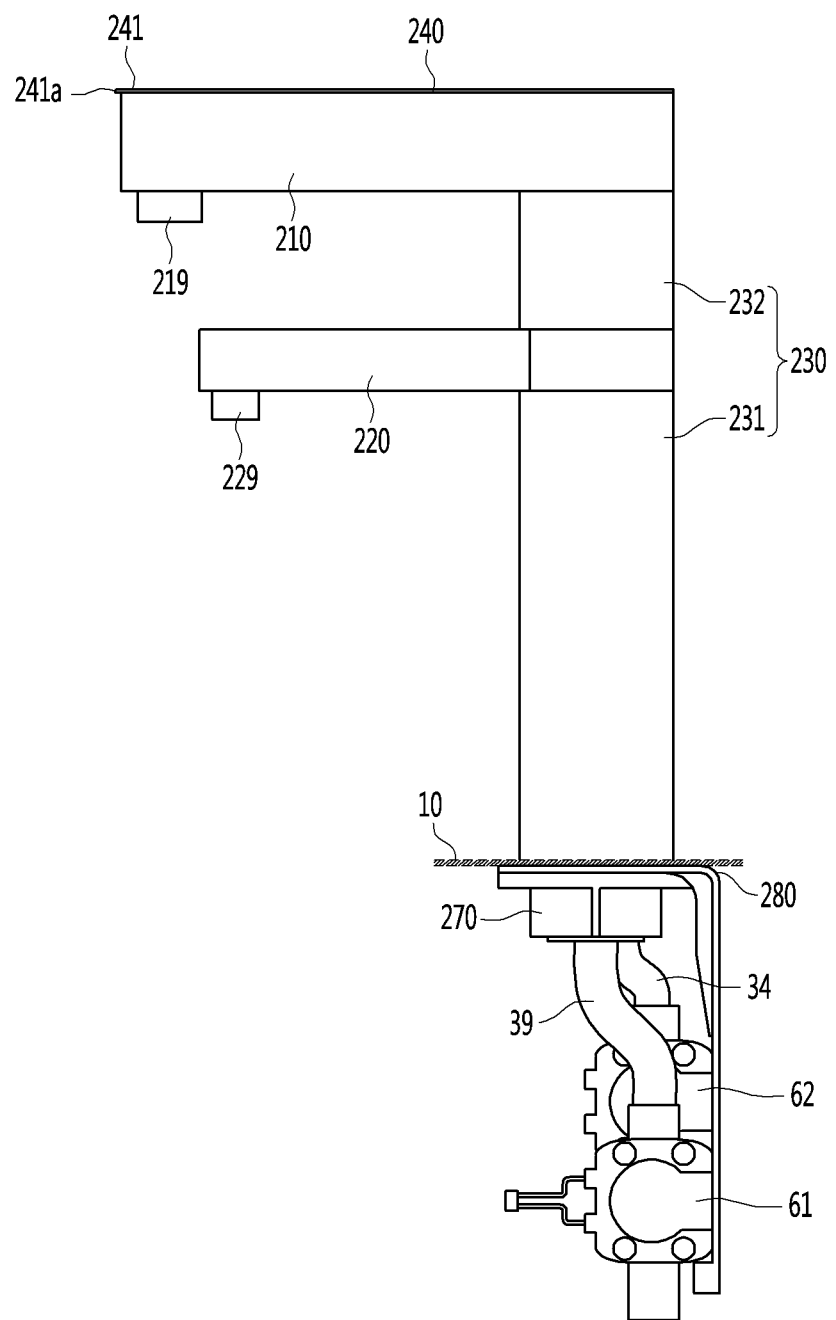
FIG. 5A is a side view of the liquid discharge part that is the main component according to an embodiment.
Figure 5B:
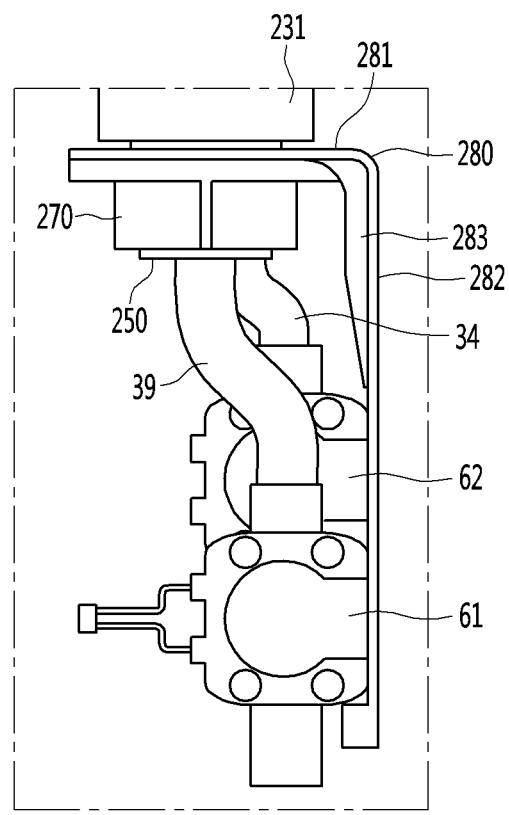
FIG. 5B is an enlarged view illustrating a portion of FIG. 5A.

FIG. 3 is a perspective view of a liquid discharge part 200 according to an embodiment. FIG. 4 is an exploded perspective view of the liquid discharge part 200 according to an embodiment. FIG. 5 is a side view of the liquid discharge part 200 according to an embodiment. FIG. 5B is an enlarged view illustrating a portion of FIG. 5A.

Referring to FIGS. 3 to 5B, the liquid discharge part 200 according to an embodiment includes the cylindrical body part 230 extending in the vertical direction and defining an outer appearance in the axial direction and the first and second liquid discharge nozzles 210 and 220 coupled rotatably with respect to the internal member 260 positioned inside the body part (or stem) 230 and positioned to be vertically spaced upward from the body part 230. Also, the body part 230 may include a first body (or first cylinder cover) 231 positioned below the second liquid discharge nozzle 220 and a second body (or second cylinder cover) 232 positioned between the first liquid discharge nozzle 210 and the second liquid discharge nozzle 220.

For example, each of the first body 231 and the second body 232 may be provided in a hollow cylindrical shape of which an upper side and a lower side are opened. The first body 231 and the second body 232 may have the same outer diameter and the same inner diameter. Also, a length of the first body 231 may be greater than that of the second body 232. In the case of the first body 231, a screw thread 231a may be positioned on an inner circumferential surface of the lower side so as to be coupled to the through-member 250 which will be described later.

The display and input part 240 may be provided on the top surface of the first liquid discharge nozzle 210 or the second liquid discharge nozzle 220. Also, the first liquid discharge nozzle 210 or the second liquid discharge nozzle 220 may be provided with outlets 211 and 221 that are opened downward, respectively.

Also, the display and input part 240 may include a plate 241 positioned at the uppermost side and exposed to the outside, a frame 242 positioned below the plate 241, and a PCB 243 positioned below the frame 242 or accommodated in the frame 242. The plate 241 may be made of a transparent or translucent material. The PCB 243 may be provided with various display parts including an LED. Also, the PCB 243 may further include a switch, a touch sensor, a button, and the like. Various elements may be installed on the PCB 243. The frame 242 serves to protect the various elements mounted on the PCB 243. The frame 242 may be provided with a plurality of opening holes through which the display part, the switch, the touch sensor, and the like are opened to the plate 241.

As illustrated in FIG. 3, the display and input part 240 may include a hot liquid selection button, a capacity selection button, a purified liquid selection button, a sterilized liquid selection button, a cold liquid selection button, a continuous liquid discharge selection button, and a liquid discharge selection button. The hot liquid selection button, the capacity selection button, the purified liquid selection button, the sterilized liquid selection button, the cold liquid selection button, and the continuous liquid selection button may be selected and activated for example when the user maintains a pressing state for 3 seconds or more.

Also, a temperature display part may be positioned above the hot liquid selection button. For example, "about 40° C.", "about 75° C.", and "about 85° C." may be displayed on the temperature display part. Thus, the user may press the hot liquid selection button to select a temperature of the hot liquid to be discharged and visually check the selected temperature of the hot liquid.

Also, a capacity display part may be positioned above the capacity selection button. For example, "about 120 ml", "about 500 ml", or "about 1000 ml" may be displayed on the capacity display part. Therefore, the user may press the capacity selection button to select a volume of liquid to be discharged and visually confirm the selected liquid discharge capacity.

Hereinafter, a method for allowing the user to manipulate the discharge of the hot liquid, the cold liquid, the purified liquid, and the sterilized liquid by using the display and input part 240 configured as described above will be described. First, when the purified liquid is to be discharged, the user presses the liquid selection button and presses the liquid discharge button 244. Thus, the purified liquid is discharged. Next, when the cold liquid is to be discharged, the user presses the cold liquid selection button and presses the liquid discharge button 244. Thus, the cold liquid is discharged.

Next, when the hot liquid is to be discharged, the user presses the hot liquid selection button, and presses the liquid discharge button 244. Thus, the hot liquid is discharged. Here, the user may select the temperature of the hot liquid according to the number of times the hot liquid selection button is pressed. Then, the selected temperature of the hot liquid may be checked. Next, when the sterilized liquid is to be discharged, the user presses a sterilized liquid selection button and presses the liquid discharge button 244. Thus, the sterilized liquid is discharged.

When the hot liquid, the cold liquid, the purified liquid, and the sterilized liquid are discharged, the user may select the capacity of each of the hot liquid, the cold liquid, the purified liquid, the sterilized liquid to be discharged through the capacity selection button. For example, when the user presses the liquid purifying button, the hot liquid button, the cold liquid button, or the sterilized liquid button and then presses the liquid dispensing button, the purified liquid, the hot liquid, the cold liquid, or the sterilized liquid of a default capacity is discharged.

For another example, when the user presses the liquid purifying button, the hot liquid button, the cold liquid button, or the sterilized liquid button and selects the capacity by pressing the capacity button and then presses the liquid discharge button, the purified liquid, the hot liquid, the cold liquid, or the sterilized liquid having the user's selected capacity is discharged. For another example, in a situation in which the purified liquid, the hot liquid, the cold liquid, or the sterilized liquid is discharged, when the user presses the discharge button again, the discharge may be ended.

The first liquid discharge nozzle 210 may have an inner space 210*a* having an opened upper side and recessed from an upper side to a lower side. Also, the frame 242 and the PCB 243 are accommodated in the inner space 210*a* defined in the first liquid discharge nozzle 210, and the plate 241 covers the opened upper side of the first liquid discharge nozzle 210.

In this case, the plate 241 may have an area larger than the opened upper area of the first liquid discharge nozzle 210. Accordingly, at least a portion of a boundary portion 241*a* of the plate 241 may protrude outward from the first liquid discharge nozzle 210, and thus, a phenomenon in which the liquid or the foreign substance flows between the plate 241 and the first liquid discharge nozzle 210 may be prevented. That is, waterproof performance may be improved.

Also, the plate 24 may have a size greater than that of the top surface of the frame 241. Therefore, at least a portion of the boundary portion 241*a* of the plate 241 may protrude outward from the frame 241, and thus, even if the liquid or foreign substance flows between the plate 241 and the first liquid discharge nozzle 210, the liquid or foreign substance may pass between sidewalls 242*g* (see FIG. 22) of the frame 241. As a result, a phenomenon in which the liquid or foreign substance is introduced onto the PCB positioned inside the sidewalls 242*g* (see FIG. 22) of the frame 241 may be prevented. That is, the waterproof performance may be improved.

Also, the opened upper portion of the first liquid discharge nozzle 210 may have a stepped protrusion 213*a* positioned on an inner side along a circumference thereof. Also, the boundary portion 241*a* of the plate 241 may be seated on the stepped protrusion 213*a*. A depth of the stepped protrusion 213*a* may be provided by a thickness of the plate 241. In this case, the opened upper portion of the first liquid discharge nozzle 210 and the plate 241 may provide a plane.

The first liquid discharge nozzle 210 provides a first insertion part (or first insertion extension) 212 extending downward so as to be inserted in a lower end of one side thereof inward from an upper end of the second body 232. The first insertion part 212 may have a hollow cylindrical shape. An outer diameter of the first insertion part 212 may be less than or equal to an inner diameter of the second body 232. The first insertion part 212 may be positioned on an opposite side of the liquid discharge hole 211. The outer diameter of the first insertion part 212 may be less than a width of the first liquid discharge nozzle 210 (a length in the direction crossing the extension direction of the liquid discharge nozzle). Accordingly, a stepped protrusion 212*a* may be positioned between the upper end of the first insertion part 212 and the lower end of the first liquid discharge nozzle 210. Also, an outer surface of the rear end (e.g., right side of FIG. 4) of the first liquid discharge nozzle 210 and an outer surface of the second body 232 may be smoothly connected to each other.

Also, the first insertion part 212 may be provided so that the outer diameter thereof gradually decreases from an upper side to a lower side. Also, the second body 232 into which the first insertion unit 212 is inserted may be provided so that the inner diameter thereof gradually decreases from the upper side to the lower side. Therefore, an operation of inserting the first insertion part 212 into the second body 232 may be easily performed.

A first cock 219 having a liquid discharge hole 211 is positioned at a front end of the first liquid discharge nozzle 210. The first cock 219 is connected to the first liquid discharge valve 61 and the second common tube 39. Therefore, the cold liquid, the hot liquid, and the purified liquid passing through the first liquid discharge valve 61 may be supplied to the first cock 219 through the second common tube 39. The second common tube 39 serves to guide the cold liquid, the hot liquid, and the purified liquid to the first liquid discharge part valve 61 and also guide the cold liquid, the hot liquid, and the purified liquid, which pass through the first liquid discharge part valve 61, to the first cock 219. In this case, the first liquid discharge valve 61 may be understood to be installed on the second common tube 39.

Also, a first cock installation hole in which the first cock 219 is installed may be defined in the front end of the first liquid discharge nozzle 210. The first cock 219 may pass through the first cock installation hole from the upper side to the lower side, and at least a portion thereof may be exposed to the lower side of the first liquid discharge nozzle 210.

The second liquid discharge nozzle 220 is provided with a second insertion part (or second insertion extension) 222 extending downward in a lower end of one side thereof so as to be inserted inward from the upper end of the first body 231. The second insertion part 222 may have a hollow cylindrical shape. An outer diameter of the second insertion part 222 may be less than or equal to the inner diameter of the first body 231. The second insertion part 222 may be provided at an opposite side of the liquid discharge part 221. An outer diameter of the second insertion part 222 may be less than a width of the second liquid discharge nozzle 220 (a length in a direction crossing the extension direction of the liquid discharge nozzle). Therefore, a stepped protrusion 222*a* may be positioned between an upper end of the second insertion part 222 and a lower end of the second liquid discharge nozzle 220. Also, an outer surface of the rear end (right side of FIG. 4) of the second liquid discharge nozzle 220 and an outer surface of the first body 231 may be smoothly connected to each other.

A second cock 229 having a liquid discharge hole 221 is positioned at a front end of the second liquid discharge nozzle 220. The second cock 229 is connected to the second liquid discharge valve 62 and the sterilized liquid tube 34. Therefore, the sterilized liquid passing through the second liquid discharge valve 62 may be supplied to the first cock 219 through the sterilized liquid tube 34. The sterilized liquid tube 34 may serve to guide the sterilized liquid to the second liquid discharge valve 62 and may also guide the sterilized liquid passing through the second liquid discharge valve 62 to the second cock 229. In this case, the second liquid discharge valve 62 may be understood to be installed on the sterilized liquid tube 34.

Also, a through-hole 220d may be defined in the lower frame 220a of the second liquid discharge nozzle 220 to be described later to expose the second cock 229 downward. The second cock 229 may pass through the through-hole 220d from the upper side to the lower side, and at least a portion thereof may be exposed to the lower side of the lower frame 220a.

The lower frame 220a may be provided with an extension wall extending upward along a circumference thereof. The extension wall is accommodated inside the second liquid discharge nozzle 220. Also, a width of the first liquid discharge nozzle 210 (a length in the horizontal direction of FIG. 4) may be greater than a width of the second liquid discharge nozzle 220. A length of the first liquid discharge nozzle 210 (a length of the liquid discharge nozzle in the extension direction) may be greater than a length of the second liquid discharge nozzle 220.

In detail, a liquid discharge hole 211 defined in the front end of the first liquid discharge nozzle 210 may be defined at a position that protrudes more than the front end of the second liquid discharge nozzle 220. Therefore, the liquid discharged from the first liquid discharge nozzle 210 may be supplied to the user without touching the second liquid discharge nozzle 220. That is, in a state in which the first liquid discharge nozzle 210 and the second liquid discharge nozzle 220 are positioned side by side to face the same direction, the liquid discharge hole 211 of the first liquid discharge nozzle 210 may be positioned at a position that does not overlap vertically the second liquid discharge nozzle 220.

Also, as described above, in the case of the second liquid discharge nozzle 220, since the length and the height are less than those of the first liquid discharge nozzle 210, the liquid discharge may be smoothly performed only in a sink bowl 12 of the sink 10. That is, since the lower space of the second liquid discharge nozzle 220 is narrow, the sterilized liquid may be easily discharged only in a state in which the second liquid discharge nozzle 220 is positioned toward the sink bowl 12 of the sink 10. Therefore, the sterilized liquid may be induced to be discharged only inside the sink bowl 12 as much as possible. Furthermore, a rotation range of the second liquid discharge nozzle 220 may be limited to only supply sterilized liquid into the sink bowl 12.

On the other hand, in the case of the first liquid discharge nozzle 210, since the length and the height are greater than those of the second liquid discharge nozzle 220, the liquid may be freely discharged from the outside of the sink 10. That is, the lower space of the first liquid discharge nozzle 210 is relatively wide, and thus, the discharging of the cold liquid, the hot liquid, and the purified liquid may be performed smoothly while the container such as a cup is positioned below the first liquid discharge nozzle 210.

Also, since the first liquid discharge nozzle 210 has a size greater than that of the second liquid discharge nozzle 220 and is positioned above the second water discharge nozzle 220, the user may recognize the first liquid discharge nozzle 210 more easily than the second liquid discharge nozzle 220 and perform the discharging of the cold/hot/purified liquid while more easily manipulating the nozzles. If the user intends to receive the cold liquid, the hot liquid, or the purified liquid in the container such as a pot that is higher than the first liquid discharge nozzle 210, the liquid discharge may be performed by positioning the container into the sink bowl 12, and the first liquid discharge nozzle 210 rotates to be positioned above the large container so that the cold liquid, the hot liquid, or the purified liquid is received into the large container.

The first liquid discharge nozzle 210 may have curved portions 213 that are convex forward and backward at both ends thereof. The second liquid discharge nozzle 220 may be provided so that the front end of the discharge port 221 is rounded. Also, a cylindrical connection part 223 may be positioned on a rear end thereof. The second insertion part 222 is positioned on a lower end of the connection part 223. An outer diameter of the connection part 223 may be greater than the width of the second liquid discharge nozzle 220. A curvature radius of an outer surface of the curved portion 213, an outer diameter of the connection part 223, and an outer diameters of the first body 231 and the second body 232 may substantially correspond to each other.

Also, the first liquid discharge nozzle 210 and the second liquid discharge nozzle 220 are freely rotatable in a state of being coupled to the sink 10. For example, the first liquid discharge nozzle 210 and the second liquid discharge nozzle 220 may rotate in a range of about 180 degrees. For another example, the first liquid discharge nozzle 210 may rotate in a range of about 180 degrees, and the second liquid discharge nozzle 220 may rotate in a range of less than 180 degrees.

The first liquid discharge nozzle 210, the second liquid discharge nozzle 220, and the body part 230 are exposed to the outside of the sink. Therefore, it has to contact with liquid and rust. Therefore, the first liquid discharge nozzle 210, the second liquid discharge nozzle 220, the body part 230 may be made of a plastic material so as not to rust.

Figure 6:
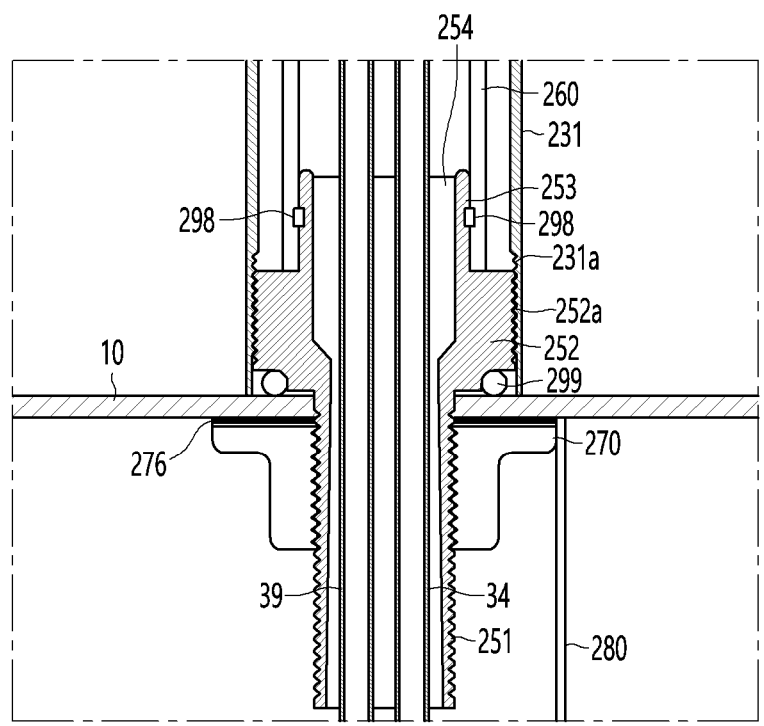
FIG. 6 is a schematic side view having partial cross-hatching added for clarity and illustrating a coupled portion between the liquid discharge part and the sink.
Figure 7A:
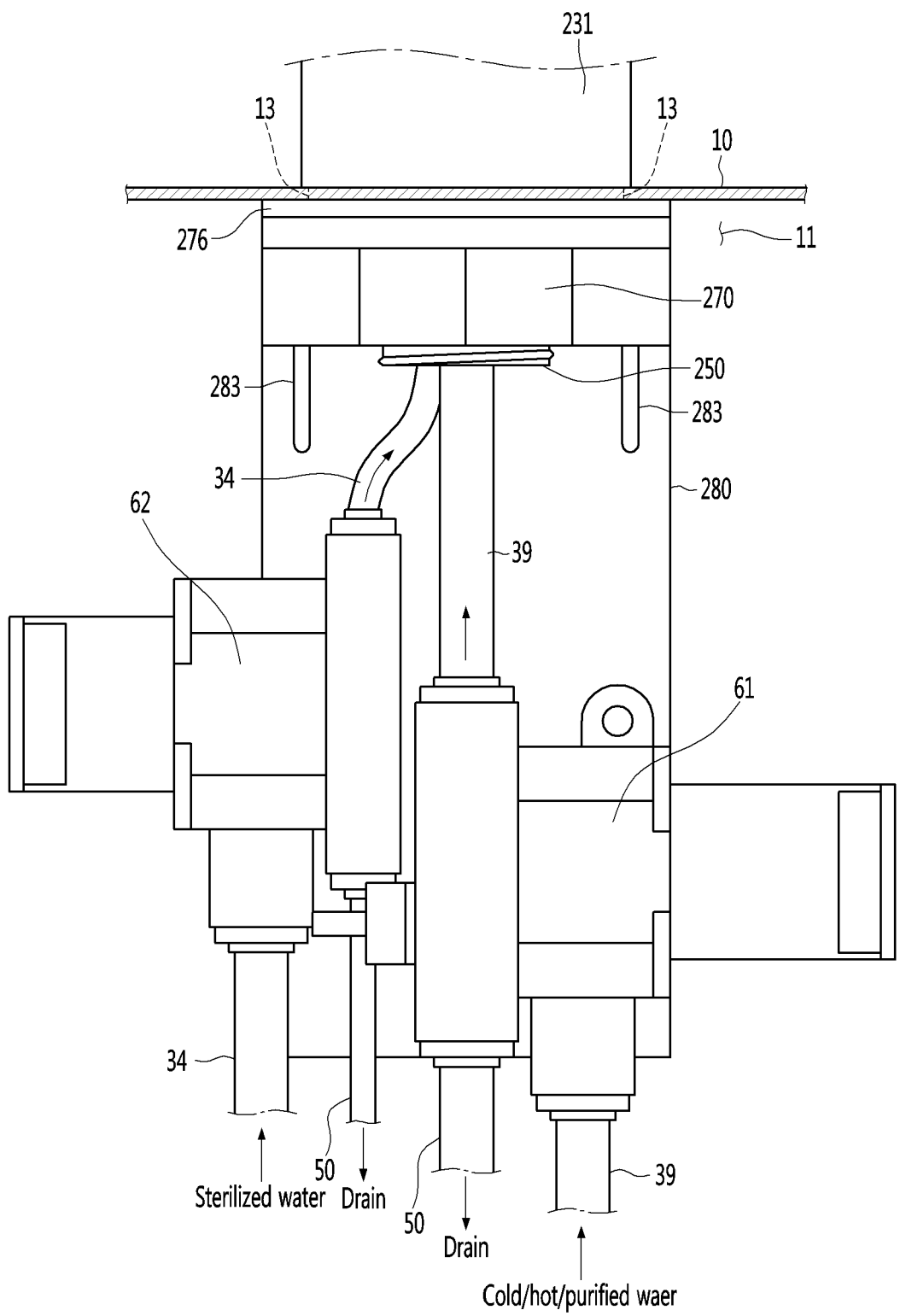
FIG. 7A is a front view illustrating an example of the coupled portion between the liquid discharge part and the sink.
Figure 7B:
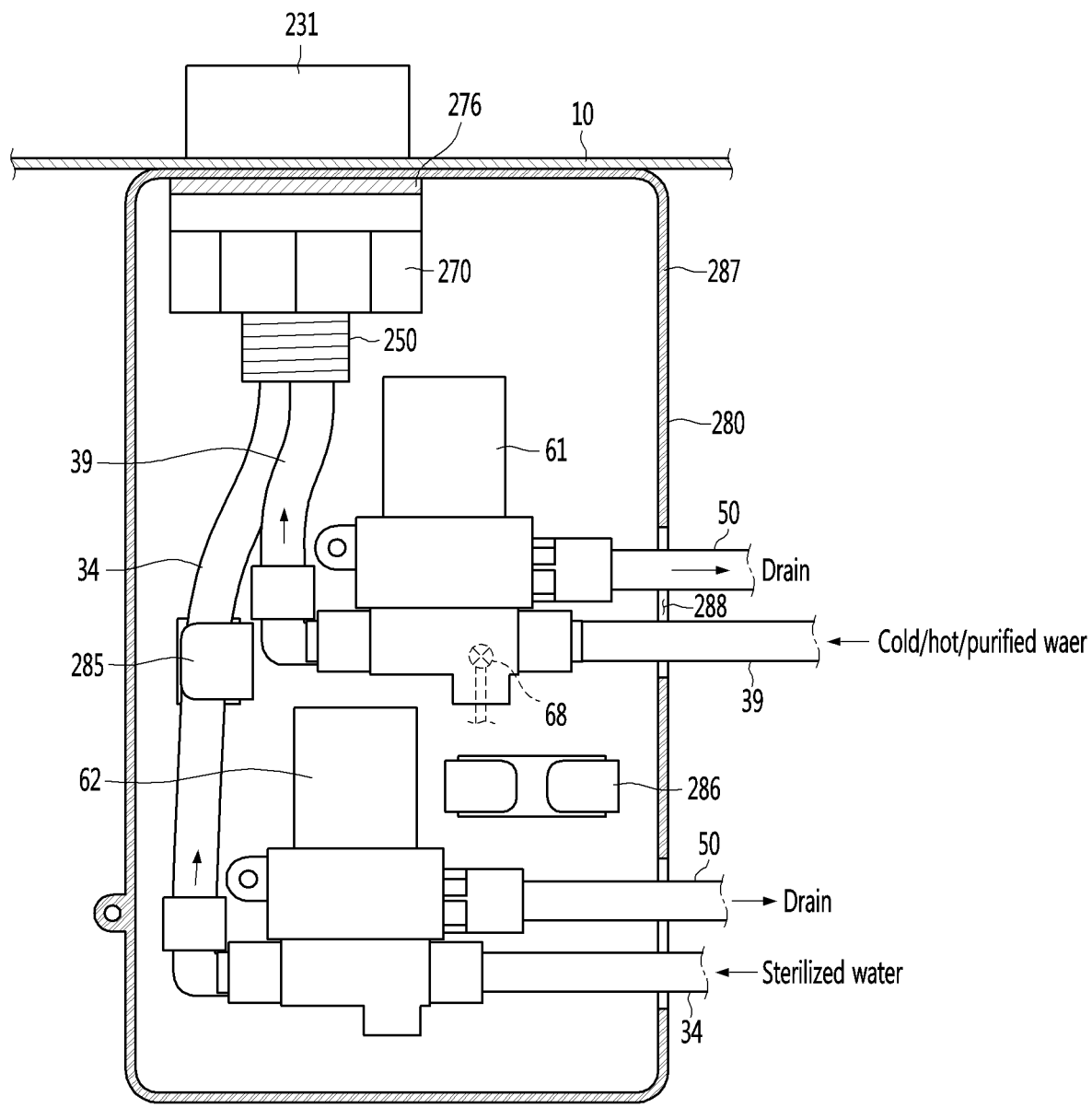
FIG. 7B is a front view illustrating another example of the coupled portion between the liquid discharge part and the sink.

FIG. 6 is a cross-sectional view illustrating a coupled portion between the liquid discharge part and the sink. FIG. 7A is a front view illustrating an example of the coupled portion between the liquid discharge part and the sink. FIG. 7B is a front view illustrating another example of the coupled portion between the liquid discharge part and the sink. FIG. 7C is a view illustrating an example of operations of a first liquid discharge valve and a second liquid discharge valve.

Hereinafter, a coupling structure of the liquid discharge part 200 and the sink 10 which are the main components according to an embodiment will be described with reference to the drawings. Referring to FIGS. 4 to 7C, the liquid discharge part 200 according to an embodiment may further include a through-member 250 passing through the sink 10.

An upper side of the through-member 250 is positioned above the sink 10, and a lower side is positioned below the sink 10. A screw 251 having a screw thread positioned on an outer circumferential surface thereof may be positioned below the through-member 250. The through-member 250 may have an extended outer diameter at a center thereof to provide a flange 252. A screw thread 252a coupled to a screw thread 231a positioned on a circumferential surface of a lower side of the first body 231 may be positioned on the outer circumferential surface of the flange 252. The flange 252 of the through-member 250 is inserted into an inner lower end of the first body 231. Also, the through-member 250 and the first body 231 may be coupled to each other by coupling the screw threads 231a and 252a to each other.

An extension part 253 having a diameter less than that of the flange 252 and extending upward may be positioned above the flange 252. Also, the through-member 250 may form a hollow part (or opening) 254 in the vertical direction. The hollow part 254 passes through the extension part 253, the flange 252, and the screw 251.

The sterilized liquid tube 34 and the second common tube 39 may pass through the hollow part 254, and the sterilized liquid tube 34 passing through the hollow part 254 may be inserted into the second liquid discharge nozzle 220, and the second common tube 39 passing through the hollow part 254 may be inserted into the second liquid discharge nozzle 210. Also, the extension part 253 is accommodated inside the internal member (or pipe) 260 which will be described later. The internal member 260 is accommodated inside the first body 231. Accordingly, when the tubes 34 and 39 are fitted inside the sink through the hollow part 254 of the through-member 250, the tube 34 passing through the hollow part 254 may be smoothly inserted into the first body 231 and the internal member 260 without being hung by a stepped portion.

The internal member 260 has a hollow tube shape having opened upper and lower portions. The upper end of the internal member 260 is accommodated inside the second body 232 and the insertion unit 212. The lower end of the internal member 260 is accommodated in the first body 231. Also, the extension part 253 of the through-member 250 is inserted into the lower end of the internal member 260.

The internal member 260 may have a cylindrical shape. The internal member 260 is fixed to the sink and serves as a rotation axis of the first liquid discharge nozzle 210 and the second liquid discharge nozzle 220. That is, the internal member 260 maintains a fixed state when the first liquid discharge nozzle 210 and the second liquid discharge nozzle 220 rotate. The internal member 260 may be made of a rigid material. The internal member 260 may be made of a metal material. The internal member 260 may be made of an aluminum material.

The second body 232 may be coupled to the upper end of the internal member 260. The upper end of the internal member 260 may be accommodated inside the second body 232. The internal member 260 and the second body 232 may have grooves and protrusions, respectively, to improve bonding force. In detail, a rotation prevention groove 269 (see FIGS. 4 and 11) may be vertically defined in an outer circumferential surface of the upper side of the internal member 260. The rotation prevention groove 269 may have a shape that is concave inward from the outer circumferential surface of the internal member 260. Also, a rotation prevention protrusion 232b (see FIGS. 4 and 11) protruding inward and vertically extending may be positioned on an inner circumferential surface of the lower end of the first body 232. When the upper end of the internal member 260 is fitted inside the second body 232, if the rotation prevention protrusion 232b is inserted into the rotation prevention groove 269, the coupling force between the internal member 260 and the second body 232 may be improved. Also, when the liquid discharge nozzles 210 and 220 rotate, the second body 232 may not rotate and may be fixed together with the internal member 260.

The sink 10 has a hole having a size greater than or equal to that of the screw 251 of the through-member 250. Then, the screw 251 of the through-member 250 passes through the sink 10 through the hole. Therefore, the screw 251 of the through-member 250 is exposed at the lower end of the sink 10. Then, the screw 251 of the through-member 250 exposed to the lower side of the sink 10 is coupled to a nut member 270. Thus, the through-member 250 may be fixed to the sink 10.

The extension part 253 provides a plurality of groove parts 255 (see FIG. 4) in an outer circumferential surface thereof, and a groove part 268 (see FIG. 4) may be defined in the inner circumferential surface under the internal member 260 into which the extension part 253 is inserted. Also, a coupling piece 298 may be inserted between the grooves 255 and 268. The coupling piece 298 may be made of an elastic material.

The groove parts 255 and 268 and the coupling piece 298 may be provided in pairs, respectively, and may be positioned at opposite positions. That is, the groove parts 255 and 268 and the coupling piece 298 may be positioned at positions symmetrical with respect to a central axis of the through-member 250 and the internal member 260. Since the groove parts 255 and 268 and the coupling piece 298 are provided as described above, a gap between the extension part 253 and the internal member 260 is secured, and the coupling force between the extension part 253 and the internal member 260 is secured.

Also, a sealing O-ring 299 may be inserted between the flange 252 of the through-member 250 and the top surface of the sink 10. For this, a groove into which the sealing member 299 is inserted may be recessed upward at an outer lower end of the flange 252 of the through-member 250. Due to the configuration of the sealing O-ring 299, a clearance between the flange 252 and the sink 10 of the through-member 250 is held, and the coupling force between the flange 252 and the sink 10 of the through-member 250 may be improved. Also, while friction occurs between the through-member 250, the internal member 260, the first body 231, and the sink 10, the through-member 250, the internal member 260, and the first body 231 may be more securely fixed to the sink 10.

Figure 8:
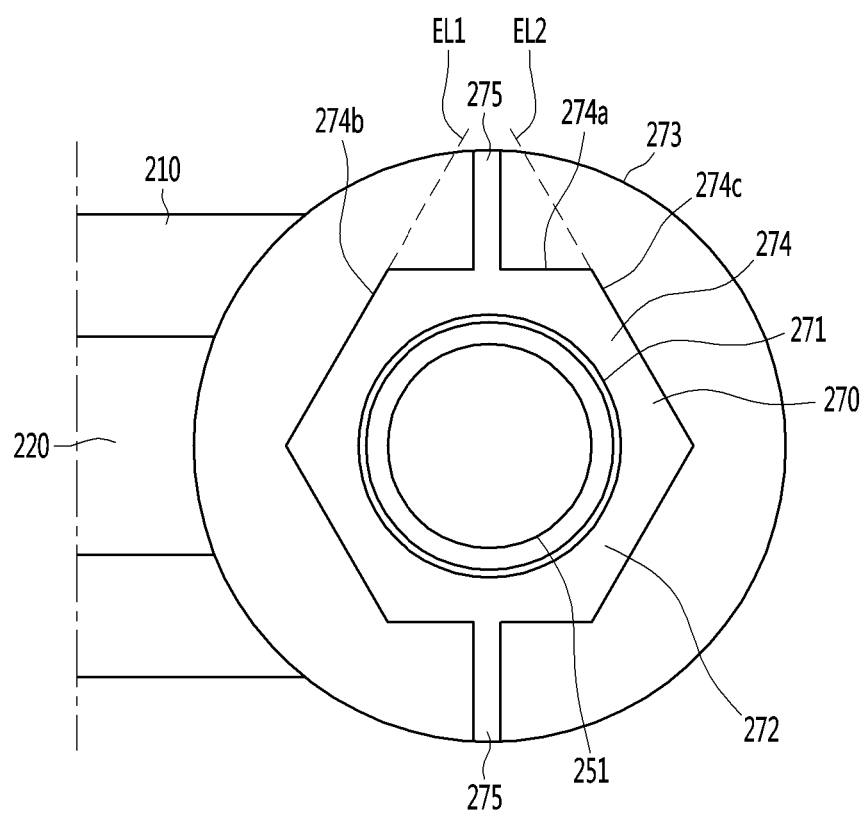
FIG. 8 is a view illustrating a state in which a nut member and a screw are coupled to each other when viewed from a lower side.
Figure 9:
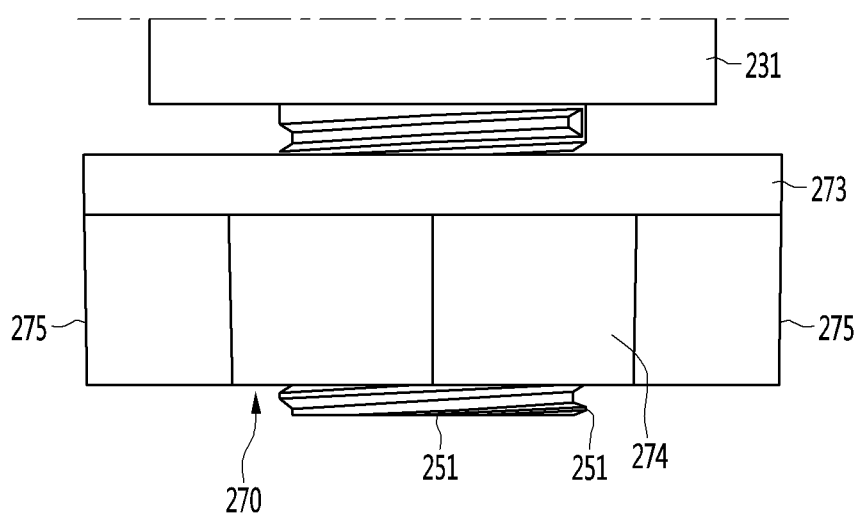
FIG. 9 is a view illustrating a state in which the nut member and the screw are coupled to each other when viewed laterally.

FIG. 8 is a view illustrating a state in which a nut member 270 and a screw 251 are coupled to each other when viewed from a lower side. FIG. 9 is a view illustrating a state in which the nut member 270 and the screw 251 are coupled to each other when viewed laterally. Referring to FIGS. 8 to 9, a screw thread is positioned on an inner circumferential surface of the nut member 270 to be engaged with the screw 251.

Also, the nut member 270 may include a body 274 having a prismatic pillar shape. For example, the body 274 may have a hexagonal pillar shape. Also, the nut member 270 may be provided with a coupling hole 271 having a screw thread positioned on an inner circumferential surface thereof. Also, the nut member 270 may be provided with an expansion part 273 extended in a disc shape at an upper end adjacent to the sink 10. A plurality of protrusion-shaped segments may be positioned on the top surface of the expansion part 273 to improve the fixing force.

Also, the nut member 270 may be provided with a pair of hook parts 275 extending along the radial direction of the expansion portion 273 at opposite sides of the body 274.

Each of the hook parts 275 may extend from the outer surface of the body 274 to a boundary of the expansion part 273.

As described above, when the body of the nut member 270 is provided in the form of a prismatic pillar including a hexagonal pillar, it is easy to allow the nut member 270 to easily rotate through a tool such as a spanner or a pliers. Also, when the hook part 275 is positioned on the nut member 270, as described above, the user may easily grip the body 274 by hand to allow the nut member 270 to be rotated manually. Also, when the expansion unit 273 is positioned as described above, the nut member 270 may be more stably coupled to the sink 10 while a contact area with the sink 10 is widened. Also, the coupling force between the liquid discharge part 200 and the sink 10 may be improved. Also, if the user rotates the nut member 270 by hand by using a fastening part, the coupling force may be strengthened.

For reference, a structure for fixing a faucet to the sink is described in Korean Utility Model Registration No. 0276610 (hereinafter, referred to as a prior art document). In detail, this document discusses a feature in which a coupling tube having a screw thread positioned on an outer circumferential surface of a lower portion of a faucet connected to a cold and hot liquid tube, and after the coupling tube passes through the coupling hole of the sink, the coupling nut is inserted into the coupling tube from a lower side of the sink to fix the liquid tap to the sink.

Here, the lower space of the sink is narrow, it may be difficult to assemble the coupling nut. Also, like this embodiment, in the case of the structure in which the liquid discharge nozzles 210 and 220 rotate, the nut member 270 may be released due to the repeated rotation of the liquid discharge nozzles 210 and 220, and thus, the nut member may intent to be more firmly coupled. In this embodiment, to solve this limitation, a shape of the nut member 270 is integrated with the disk-shaped expansion portion 273 and the hexagonal pillar-shaped body 274. Then, the linear hook parts 275 are positioned on both sides of the hexagonal pillar-shaped body 274 so as to be symmetrical with each other.

Also, the hook part 275 may overlap virtual extension lines EL1 and EL2 of inclined surfaces 275b and 274c positioned on both sides adjacent to the one surface 274a of the body 274 to which the hook part 275 is connected or may be provided so as not to protrude more than the virtual extension lines EL1 and EL2. Therefore, when the body 274 rotates using a nut coupling tool, for example, a spanner or pliers, interference with the hook part 275 may be prevented. Also, the hook part 275 may be positioned only on two sides of the body 274. The reason for this is to allow the nut member 270 to be turned by using a wrench through four sides on which the hook part 275 is not positioned.

Referring to the coupling process of the through-member 250 and the nut member 270, the user first puts the through-member 250 into the hole 13 (see FIG. 7A) defined in the sink 10 above the sink 10 and couples the nut member 270 to the screw 251 exposed to the lower side of the sink 10. Here, the user may hold the hook part 275 by hand to easily primarily couple the nut member 270 to the screw 251 even if the view is obscured. Here, since the hook part 275 is positioned to cross the rotation direction of the nut member 270, the user may allow the nut member 270 to easily rotate by holding the hook part 275 by the hand.

Also, when the primary coupling is completed as described above, the nut member 270 may be secondly coupled to the screw 251 by turning the body 274 with a tool. Therefore, the nut member 270 may be coupled more firmly to the screw 251. Also, to improve the coupling force of the through-member 250, the nut member 270, and the sink 10, a rubber washer 276 (see FIG. 7A) may be inserted between the bottom surface of the sink 10 and the extension part 273 of the nut member 270.

The hole 13 (see FIG. 7A) defined in the sink 10 is less than a diameter of the flange 252. Also, the diameter of the flange 252 is less than each of the inner diameter of the first body 231 and the inner diameter of the internal member 260. Thus, the flange 252 may be accommodated inside the first body 231 and the internal member 260.

The first liquid discharge valve 61 and the second liquid discharge valve 62 may be installed inside the liquid discharge part 200. In detail, the first liquid discharge valve 61 and the second liquid discharge valve 62 may be installed inside the first body 231 or the second body 232.

For another example, the first liquid discharge valve 61 and the second liquid discharge valve 62 may be installed outside the liquid discharge part 200. In detail, the first liquid discharge valve 61 and the second liquid discharge valve 62 may be installed outside the first body 231 or the second body 232. In this case, the first liquid discharge valve 61 and the second liquid discharge valve 62 may be installed under the sink 10.

The liquid discharge part 200 may further include a bracket 280 on which the first liquid discharge valve 61 and the second liquid discharge valve 62 are installed. The bracket 280 includes a horizontal part 281 inserted between the bottom surface of the sink 10 and the nut member 270 and a vertical part 282 extending in the vertical direction from one side of the horizontal part 281. A hole through which the screw 251 of the through-member 250 passes may be defined in the horizontal part 281. The screw 251 sequentially passes through the holes 13 (see FIG. 7A) of the sink 10 and the hole of the horizontal part 281, and then, is coupled to the nut member 270 at the lower side of the horizontal part 281. A reinforcing rib 283 may be positioned on an inner surface of an edge defined by the horizontal part 281 and the vertical part 282.

Also, the first liquid discharge valve 61 and the second liquid discharge valve 62 may be coupled to the vertical part 282. Also, the vertical part 282 may be provided with a plurality of tube fixing hooks 285 for fixing various tubes 34 and 39 in a grasping manner, and a plurality of valve fixing hooks 286 for fixing the valves 61 and 62.

Also, the vertical part 282 may define an extension wall 287 in the vertical direction with the vertical part 282 on one side or both sides. Also, a tube through-hole or a tube through-groove 288 through which the various tubes 34 and 39 pass may be defined in the extension wall 287.

The first liquid discharge valve 61 and the second liquid discharge valve 62 may be positioned on the vertical part 282 in the vertical direction. In another example, the first liquid discharge valve 61 and the second liquid discharge valve 62 may be positioned on the vertical part 282 in the horizontal direction. In another example, the first liquid discharge valve 61 and the second liquid discharge valve 62 may be positioned to be offset from each other in the vertical part 282. That is, the first liquid discharge valve 61 and the second liquid discharge valve 62 may be positioned at one upper end and the other lower end of the vertical part 282, respectively.

Referring to FIG. 7A, the first liquid discharge valve 61 and the second liquid discharge valve 62 may be positioned so that the cold, hot, purified, and sterilized liquid flow from the lower side to the upper side. Also, the cold, hot, purified, and sterilized liquid may be discharged from the lower side to the discharge nozzles 210 and 220, and the drain may be performed from the upper side to the lower side.

Referring to FIG. 7B, the first liquid discharge valve 61 and the second liquid discharge valve 62 may be positioned so that the cold, hot, purified, and sterilized liquid flow from a right side to a left side. Also, the cold, hot, purified, and sterilized liquid may be discharged from the lower side to the discharge nozzles 210 and 220, and the drain may be performed the left side to the right side.

Hereinafter, a switching operation of the first liquid discharge valve 61 and the second liquid discharge valve 62 will be described with reference to FIG. 7C.

The first liquid discharge valve 61 and the second liquid discharge valve 62 may be opened and covered by a plunger 66 which operates vertically by an electric signal.

First, as illustrated in (a) of FIG. 7C, when the plunger 66 ascends, a passage connecting an inlet 63 through which liquid is introduced and an outlet 64 through which liquid is discharged is opened. Here, the inlet 63 and the outlet 64 are positioned at opposite positions, respectively. That is, the inlet 63 and the outlet 64 may be positioned on both sides with respect to the plunger 66. Thus, the liquid flowing into the inlet 63 is discharged to the outlet 64, and the liquid discharged to the outlet 64 is supplied to the liquid discharge nozzles 210 and 220.

Here, as the plunger 66 ascends, the passage connecting the drain hole 65 to the inlet 63 is covered. The drain hole 65 may be positioned in the vertical direction (see FIG. 7C) with the inlet 63. A sealing part 67 may be positioned below the plunger 66 to prevent liquid from leaking. The temperature sensor 68 may be installed to be exposed to the inlet 63. The temperature sensor 68 may be installed to be exposed between the inlet 63 and a branch point 69 opened and closed by the plunger 66 based on the flow of liquid.

On the other hand, as illustrated in (b) of FIG. 7C, when the plunger 66 descends, a passage connecting an inlet 63 through which liquid is introduced and an outlet 64 through which liquid is discharged is blocked. Also, as the plunger 66 descends, the passage connecting the drain hole 65 to the inlet 63 is opened.

Therefore, the liquid flowing into the inlet 63 is discharged to the drain hole 65, and the liquid discharged to the drain hole 65 is drained.

For reference, the above-described temperature sensor and the temperature sensor that is described later may be installed on a side of the inlet 63. Also, the temperature sensor may be installed between the inlet 63 and the plunge 66 based on the temperature sensor and the direction in which the liquid to be described later flow.

When using an under sink liquid purifier, the liquid discharge nozzle may be provided above the sink. In the case of this embodiment, the liquid discharge nozzle for discharging the drinking liquid (the cold, hot, and purified liquid) and the liquid discharge nozzle for discharging the sterilized liquid may be distinguished from each other, but each liquid discharge nozzle may be implemented in one body and independently rotatably implemented. Also, in the case of the first liquid discharge nozzle, a touch input and a display output may be implemented. As described above, the respective liquid discharge nozzles rotate in the left and right direction to maximize user convenience.

Figure 10:
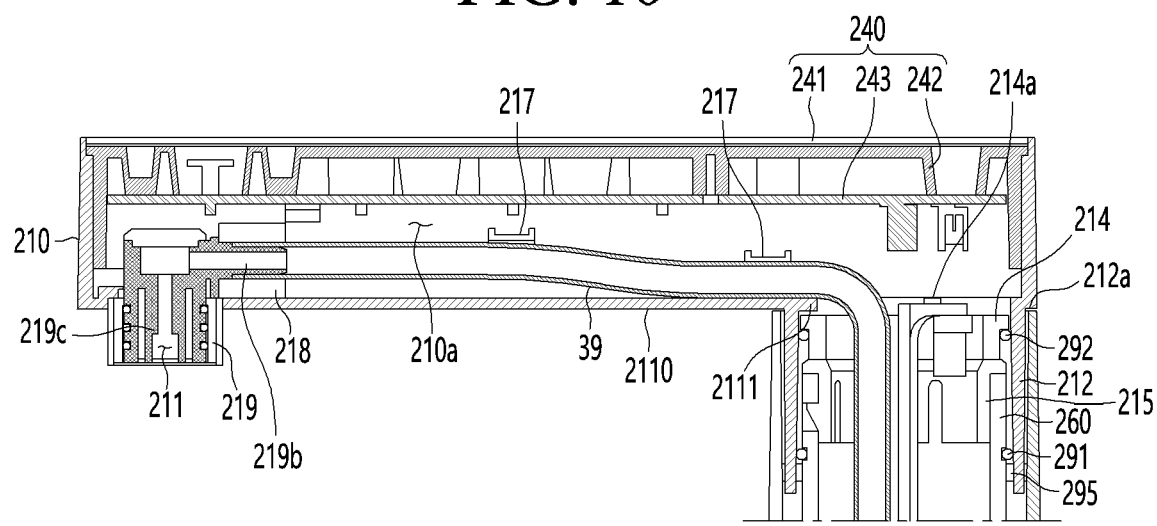
FIG. 10 is a schematic side view having partial cross-hatching added for clarity and illustrating a first liquid discharge nozzle that is a portion of components according to an embodiment.
Figure 11:
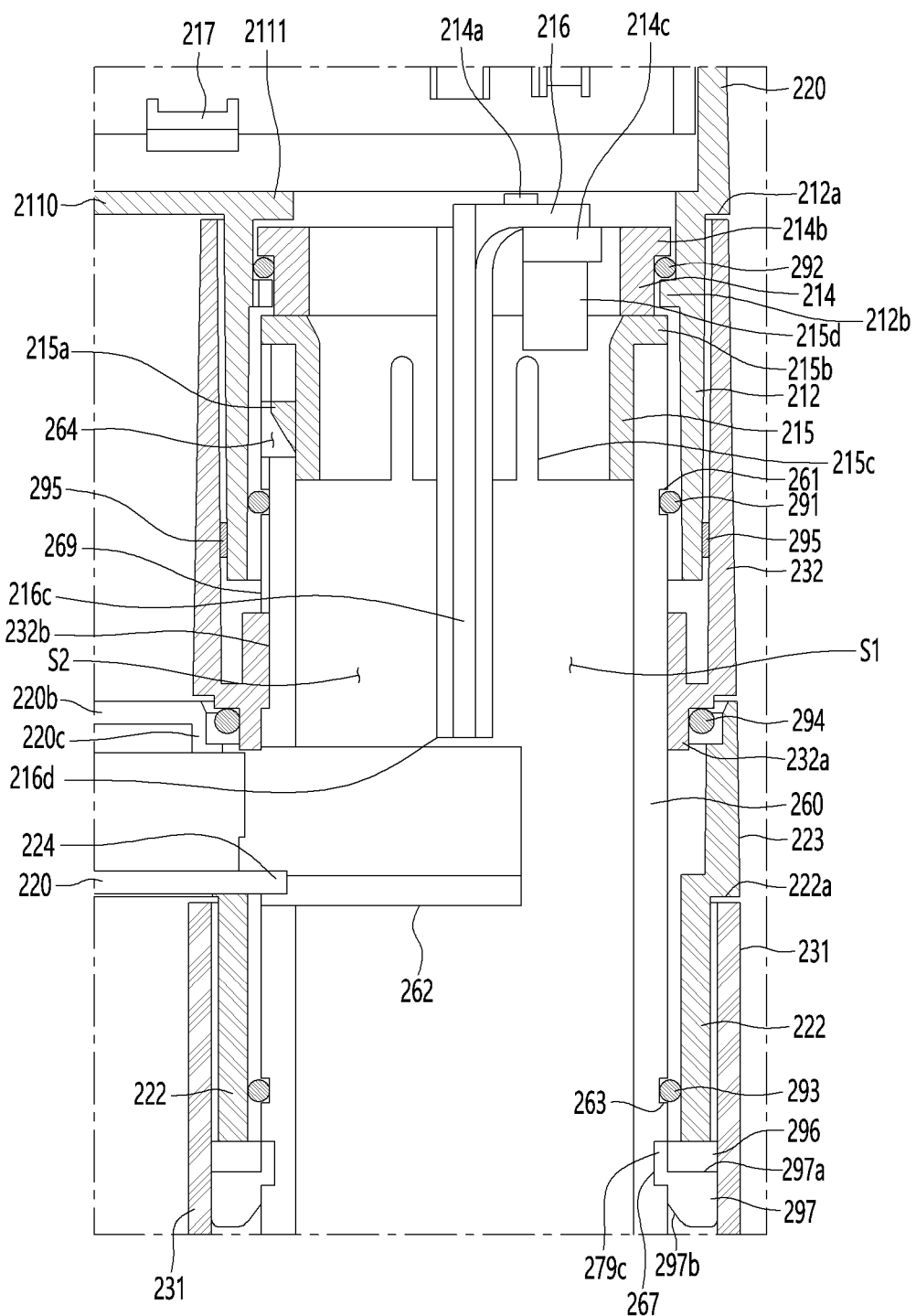
FIG. 11 is an enlarged schematic side view having partial cross-hatching added for clarity and illustrating a portion of FIG. 10.
Figure 12A:
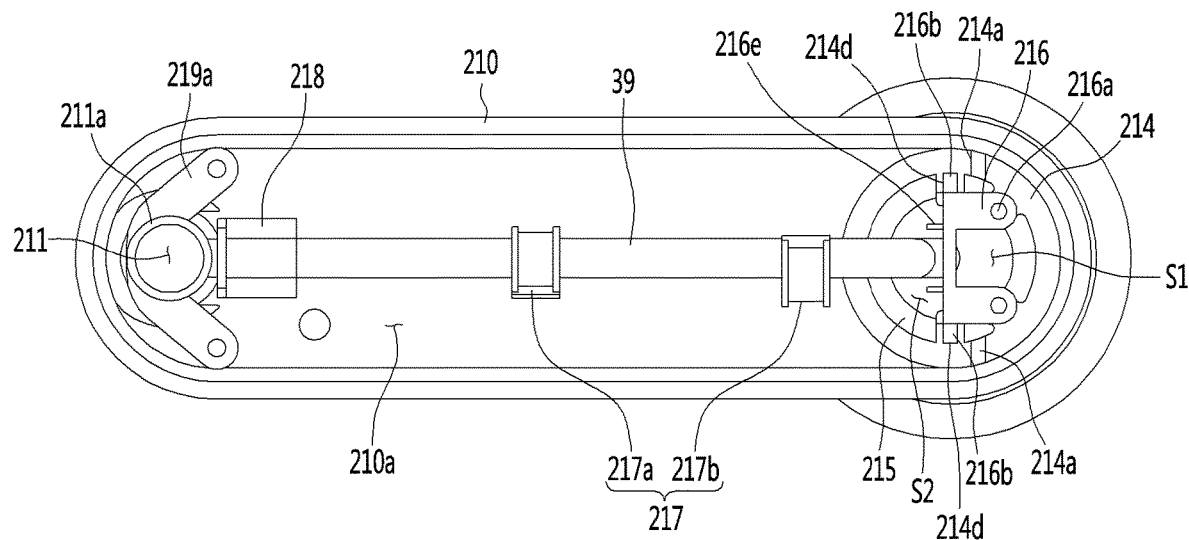
FIG. 12A is a view illustrating a state in which a display and input part is separated from the first liquid discharge nozzle when viewed from an upper side.
Figure 12B:
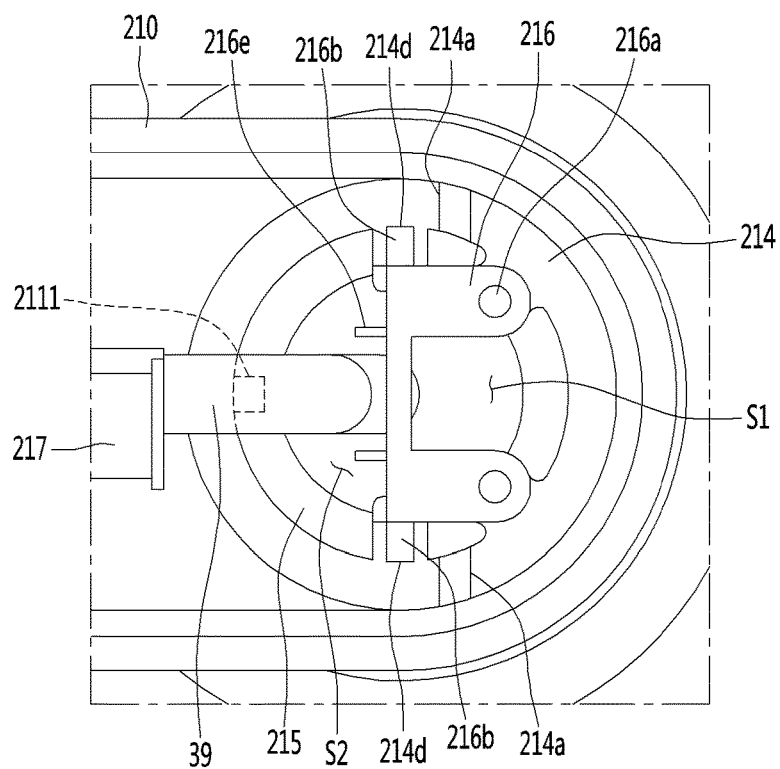
FIG. 12B is an enlarged view illustrating a portion of FIG. 5A.
Figure 13:
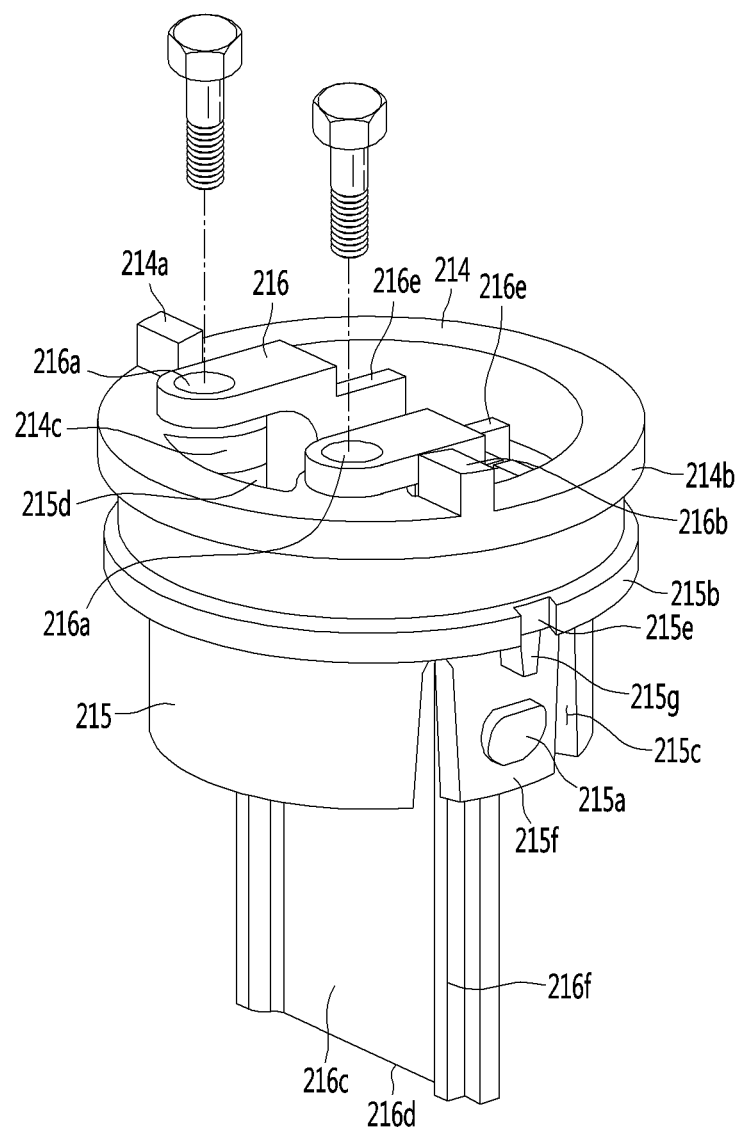
FIG. 13 is a view illustrating a state in which a first connection member and a second connection member, which are portions of the components, are coupled to a coupling member according to an embodiment.

FIG. 10 is a cross-sectional view of a first liquid discharge nozzle 210 that is a portion of components according to an embodiment. FIG. 11 is an enlarged view illustrating a portion of FIG. 10. FIG. 12A is a view illustrating a state in which the display and input part 240 is separated from the first liquid discharge nozzle 210 when viewed from an upper side. FIG. 12B is an enlarged view illustrating a portion of FIG. 5A. FIG. 13 is a view illustrating a state in which a first connection member and a second connection member are coupled to a coupling member according to an embodiment.

Referring to FIGS. 10 to 13, a rotation angle of the first liquid discharge nozzle 210 may be limited. For example, the first liquid discharge nozzle 210 may rotate in a range of about 90 degrees to about 270 degrees. For this, a rotation limit structure for limiting the rotation angle of the first liquid discharge nozzle 210 is used.

In the case of the first liquid discharge nozzle 210, a first stopper 2111 protruding into an inner hollow of the insertion part 212 may be positioned on a rear end of the lower frame 2110 defining the bottom surface. The first stopper 2111 protrudes to a right side with reference to FIG. 10.

Also, when the first liquid discharge nozzle 210 rotates inside the insertion unit 212, a ring-shaped first connection member 214 that does not rotate together with the first water discharge nozzle 210 and is maintained in a fixed state is provided. The first connection member 214 may be provided with a rotation limit protrusion 214a that protrudes upward to limit the rotation of the first stopper 2111 on each of both sides.

In the pair of rotational limit protrusions 214a, a surface facing the first liquid discharge nozzle 210 may be angled at about 180 degrees while forming a straight line (see a dotted line in FIG. 13). Therefore, the rotation angle of the first stopper 2111 is limited to about 180 degrees by the pair of rotation limit protrusions 214a, and as a result, the rotation angle of the first liquid discharge nozzle 210 may be limited to about 180 degrees. As described above, when the first liquid discharge nozzle 210 rotates, the first stopper 2111 is hooked by the pair of rotation limit protrusions 214a so that the rotation range of the first liquid discharge nozzle 210 may be limited. The first stopper 2111 may be positioned to overlap at least a portion of the pair of rotation limit protrusions 214a with respect to the horizontal direction.

Also, the first connection member 214 is fixed to an upper side of the internal member 260. Accordingly, the first connection member 214 may be maintained in a fixed state together with the internal member 260. That is, when the first liquid discharge nozzle 210 and the second liquid discharge nozzle 220 rotate, the internal member 260 and the first connection member 214 do not rotate to be maintained in the fixed state. In detail, the internal member 260 does not rotate together and is maintained in the fixed state when the first liquid discharge nozzle 210 and the second liquid discharge nozzle 220 rotate. Also, the first connection member 214 fixed to the internal member 260 is maintained in the state fixed to the internal member 260.

The first connection member 214 is provided with a pressing part 214b in the form of a flange extending outward on an upper end thereof. The upper end of the pressing part 214b is positioned below the first stopper 2111. The rotation limit protrusion 214a is positioned to protrude upward from the pressing part 214b, and the first stopper 2111 is positioned on the rotation limit protrusion 214a when the first liquid discharge nozzle 210 rotates in rotation angle while being hooked with the rotation limit protrusion. The first stopper 241 may rotate while being in contact with and supported by a top surface of the pressing part 214b.

Also, a second O-ring that generate rotation resistance so as to perform sealing, generate rotation resistance, secure fixing force, and improve rotational manipulation feeling may be inserted between the first connection member 214 and the insertion part 212 of the first liquid discharge nozzle 210. The second O-ring 292 may be inserted and fixed between the pressing part 214b of the first connection member 214 and a support protrusion 212b protruding inward from an inner side of the insertion part 212. Also, while the support protrusion 212b is fixed to a lower side of the pressing part 214b, the first liquid discharge nozzle 210 may be fixed without being separated upward.

Also, an interval between the first connection member 214 and the insertion part 212 of the first liquid discharge nozzle 210 may be maintained by the second O-ring 292. Also, shaking of the first liquid discharge nozzle 210 may be prevented by the second O-ring 292. Also, a clearance between the first connection member 214 and the insertion part 212 of the first liquid discharge nozzle 210 may be maintained by the second O-ring 292. Also, while friction is generated by the second O-ring 292, and the rotation of the first liquid discharge nozzle 210 is smoothly performed, the manipulation feeling may be improved, and the first liquid discharge nozzle 210 may be fixed to the rotating position.

The first connection member 214 may be coupled to the internal member 260 through the ring-shaped second connection member 215. A lower end of the second connection member 215 may be inserted into an upper end of the internal member 260. Also, a plurality of fixing hooks 215a may be spaced apart from each other on an outer surface of the second connection member 215 in a circumferential direction. Also, a plurality of fixing holes 264 into which the fixing hooks 215a are respectively inserted may be defined in the internal member 260 so as to be spaced apart from each other in the circumferential direction. The second connection member 214 may be provided with a seating part 215b extending outward so as to be seated on an upper end of the internal member 260 at an upper end thereof.

Also, a plurality of slits 215c, each having a shape in which the second connection member 215 is recessed upward from the lower end may be spaced apart from each other in the circumferential direction. The slits 215c may be provided in plurality. Also, a deformable part 215f may be positioned between the slits 215c to be deformed in a radial direction so as to be contracted toward a center side thereof. Also, the fixing hooks 215a are positioned on an outer surface of the deformable part 215f. Also, each of the fixing hooks 215a may gradually increase in height from a lower side to an upper side. Therefore, the fixed hook 215a may be positioned so that an outer surface thereof is inclined. As described above, the fixing hook 215a is fitted into the fixing hole 264 defined in the upper side of the internal member 260. Thus, the second connection member 215 and the internal member 260 are coupled to each other.

The internal member 260 may be positioned to open the cutoff hole 265 (see FIG. 4) while communicating with the upper end of the internal member 260 and the fixing hole 264. A diameter of the fixing hole 264 may be greater than a width of the cutoff hole 265. Also, in the second connection member 215, a hole insertion protrusion 215g inserted into the cutoff hole 265 may be positioned on an upper side of the fixing hook 215a. Therefore, as the hole insertion protrusion 215g is inserted into the cutoff hole 265, the coupling force between the second connection member 215 and the internal member 260 may be further improved.

Also, a guide groove 215e may be defined in the seating part 215b of the second connection member 215 at a position corresponding to the fixing hook 215a and the hole insertion protrusion 215g. Therefore, when assembling the second connection member 215 with the internal member 260, the second connection member 215 may be coupled to the internal member by pressing the second connection member 215 to the inside of the internal member 260 in a state in which the guide groove 215e and the fixing hole 264 are aligned with each other from the outside.

The first connection member 214 and the second connection member 215 may be integrated with each other as necessary. Alternatively, the first connection member 214 and the second connection member 215 may be provided as separate configurations and then coupled to each other in various manners.

The first connection member 214 and the second connection member 215 may be coupled to each other through a separate coupling member 216. For example, the coupling member 216 may be connected to a coupling boss 214c protruding from an inner surface of the first connection part 214 and may include a coupling hole 216a coupled to the coupling boss 215d protruding from an inner surface of the second connection part 215 through a bolt or a screw. When viewed from the top surface, the coupling member 216 may include a coupling bar connecting bars parallel to each other to one side of the coupling bar and may have a "⊏" shape. Also, when viewed from the side surface, the coupling member 216 may include a horizontal part positioned above the first connection member 214 and a vertical wall 216c extending vertically downward from one side of the horizontal part to partition the hollow of the internal member 260 into a plurality of spaces and may have a "¬" shape.

At least two or more coupling bosses 214c and 215d are positioned to protrude from positions that are symmetrical to each other on the inner surfaces of the first connection member 214 and the second connection member 215, respectively, and the coupling hole 216a may be provided one by one in the coupling bars of the coupling member 216 to correspond to the coupling bosses 214c and 215d.

The coupling member 216 may include a horizontal part on which the coupling hole 216a is defined and a vertical wall 216c extending downward from one side of the horizontal part. Also, a reinforcing rib 216f protruding outward from one side may be positioned on the vertical wall 216c in a longitudinal direction (e.g., in the vertical direction of FIG. 13). The reinforcing rib 216f may be positioned at each of both sides. At least two reinforcing ribs 216f may be provided. Also, the reinforcing rib 216f may be positioned in a space S1 of one side partitioned by the vertical wall 216c. A wire connected to the display and input part 240 may pass through the space S1.

Guide ribs 216e protruding to be spaced apart from each other are positioned on the vertical wall 126c in the longitudinal direction (e.g., in the vertical direction in FIG. 13). The guide ribs 216e are provided to define a space between the guide ribs 216e. Also, a second common tube 39 may be guided to a space between the guide ribs 216e and positioned in the vertical direction, and then connected to the first liquid discharge nozzle 210.

In another example, in the coupling member 216, the coupling protrusion 216b protruding outward may be positioned on each of both sides so as to be inserted into the coupling groove 214d protruding to be concave inward from an inner surface of the first connection member 214 or the coupling groove provided to be concave inward from an inner surface of the second connection part 215.

The coupling grooves 214d may be positioned at both sides facing each other on the inner surface of the first connection member 214. The coupling groove 214d may have a center line parallel to the direction in which the coupling protrusion 216b is inserted to be angled at about 180 degrees. Also, the coupling protrusion 216b may be positioned at both sides of the coupling member 216, and a center line parallel to the direction in which the coupling protrusion 216b is inserted into the coupling groove 214d may be angled at about 180 degrees.

The vertical wall 216c of the coupling member 216 is positioned to cross the hollow region of the first connection member 214 so that the hollow region of the first connection member 214 is partitioned into two spaces S1 and S2. Also, the space S2 is relatively close to the liquid discharge hole 211 and may be used as a space dedicated to the second common tube 39. Also, the remaining space S1 may be used as a dedicated space through which the wire connected to the display and input part 240 pass. Thus, twisting and tangling of the wires may be prevented.

A lower end 216d of the vertical wall 216c extends to the second discharge nozzle 220 to partition the sterilized liquid tube 34 from the electric wire and is bend to be connected to the second discharge nozzle 220 to function as a role of pressing the bent portion of the sterilized liquid tube 34.

The first connection member 214 and the second connection member 215 may be stacked in the vertical direction. Also, the first connection member 214 and the second connection member 215 may be combined into one body through the coupling member 216 and the screw. That is, the first connection member 214 and the second connection member 215 are coupled to the coupling member 216 in one module. Thereafter, the first connection member 214, the second connection member 215, and the coupling member 216, which are coupled to the one module, are inserted and coupled to the upper side of the internal member 260.

Also, a hook protrusion 217 for fixing the second common tube 39 positioned inside the first liquid discharge nozzle 210 is positioned on the lower frame 2110 defining the bottom surface of the first liquid discharge nozzle 210. The hook protrusion 217 has one side fixed to the lower frame 2110 and the other side spaced apart from the lower frame 2110 and has a bent shape in a hook shape. The hook protrusion 217 may be convex upward. The hook protrusion 217 may be positioned at each of a plurality of positions of the lower frame 2110. Also, a height of the hook protrusion 217 may be variously provided. Also, the hook protrusion 217 may be positioned at a position that is shifted from the lower frame 2110. When the plurality of hook protrusions 217 are provided, one hook protrusion 217a may be positioned with one side opened, and the other hook protrusion 217b may be positioned with the other side opened.

Also, an end of the second common tube 39 is connected to the first cock 219 through which the cold/hot/purified liquid are discharged. Both sides of the first cock 219 may be fixed to the lower frame 2110 by separate fixing brackets 219a coupled to the lower frame 2110. Each of the fixing brackets 219a has a shape of 'V' and 'U'. Then, both ends are fixed to the lower frame 2110 through screw screwing or the like. When replacing the cock and the tube, it may be performed by unscrewing the fixing bracket 219a.

The first cock 219 may include an inlet 219b extending in the horizontal direction and connected to the second common tube 39 and an outlet 219c communicating with the inlet 219b and extending in the vertical direction. The second common tube 39 and the inlet 219b may be fixed to each other by a separate fixing cap 218 for pressing the second common tube 39 in a state in which the second common tube 39 is fitted to the outside of the inlet 219b.

Also, the second common tube 39 and the inlet 219b may be coupled to each other in a thermal fusion manner. In this case, when the second common tube 39 is replaced, the whole replacement may be performed up to the first cock 219. For example, the first cock 219 and the second common tube 39 may be installed and separated from the first liquid discharge nozzle while being integrally coupled to each other.

When being installed, the display and input part 240 defining the top surface of the first liquid discharge nozzle 210 is separated. Then, the upper side of the first liquid discharge nozzle 210 is opened. Then, the first cock 219 and the second common tube 39 are inserted from the upper side of the first discharge nozzle 210 to the lower side, and the second common tube 39 is put into the internal member 260. Then, the display and input part 240 is coupled to the first liquid discharge nozzle 210.

On the contrary, when being separated, the display and input part 240 defining the top surface of the first liquid discharge nozzle 210 is separated. Then, the upper side of the first liquid discharge nozzle 210 is opened. Then, the first cock 219 and the second common tube 39 are withdrawn out from the lower side of the first liquid discharge nozzle 210. Then, the second common tube 39 is pulled upward. Here, the second common tube 39 is separated from the first liquid discharge valve. Thereafter, after the new first cock 219 and the second common tube 39 are installed, the display and input part 240 is re-coupled to the first liquid discharge nozzle 210. The display and input part 240 may be coupled to and separated from the first liquid discharge nozzle 210 by screwing, adhesion, or the like.

In this embodiment, the hot liquid discharging, the cold liquid discharging, and the purified liquid discharging are possible by the user's selection through the first liquid discharge nozzle positioned at the upper portion. For this functionality, the first liquid discharge nozzle is provided with the display and input part 240 that selects the type of liquid. Also, to control the display and input part 240, a substrate (PCB) is mounted therein, and a plurality of power lines or signals should be connected to a liquid purifier body positioned under the sink along the tube.

In such a structure, when the upper first liquid discharge nozzle and the lower second liquid discharge nozzle rotate, the wire twisting and entanglement may occur due to the rotation of the two nozzles, and thus short-circuit of the power line and a malfunction due to the short-circuit may occur. To solve this concern, the coupling member 216 is positioned between the upper first liquid discharge nozzle and the lower second liquid discharge nozzle. The coupling member 216 divides an inner space of the internal member 260 into two spaces. One of the spaces is used as a space through which the power lines and various wires passes. Also, the other one space may be used as a space through which the liquid discharge tubes pass.

Also, a first O-ring 291 may be inserted between an outer surface of the internal member 260 and the insertion part 212 of the first liquid discharge nozzle 210 to prevent leakage, prevent shaking, generate rotational resistance, and improve manipulation sensitivity. The internal member 260 may have a first insertion groove 261 that is concave inward so that the first O-ring 291 is inserted along the circumferential direction.

Also, an interval between the internal member 260 and the insertion part 212 of the first liquid discharge nozzle 210 may be maintained by the first O-ring 291. Also, the shaking of the first liquid discharge nozzle 210 may be prevented by the first O-ring 291. Also, a clearance between the internal member 260 and the insertion part 212 of the first liquid discharge nozzle 210 may be maintained by the first O-ring 291. Also, while friction is generated by the first O-ring 291, and the rotation of the first liquid discharge nozzle 210 is smoothly performed, the manipulation feeling may be improved, and the first liquid discharge nozzle 210 may be fixed to the rotating position.

In addition, a first square ring is inserted between the outer surface of the internal member 260 and an inner surface of the insertion part 212 and/or between an outer surface of the insertion part 212 and an inner surface of the second body 232. The first square ring 295 may be positioned below the first O-ring 291 fitted in the first insertion groove 261.

The interval between the internal member 260, which is a fixed body, and the insertion part 212, which is a rotating body, may be maintained by the first O-ring 291, and also, when the insertion part 212 rotates, the rotation resistance between the internal member 260 and the insertion part 212 may occur by the first O-ring 291. Also, the friction occurs in an axial direction to hold the first liquid discharge nozzle 210 without being shaken in the axial direction.

Also, a distance between the second body 232 and the insertion part 212 may be constantly maintained by the first square ring 295. For reference, the first square ring 295 may have a ring shape, and a cross-section thereof may have a quadrangular shape.

Figure 14:
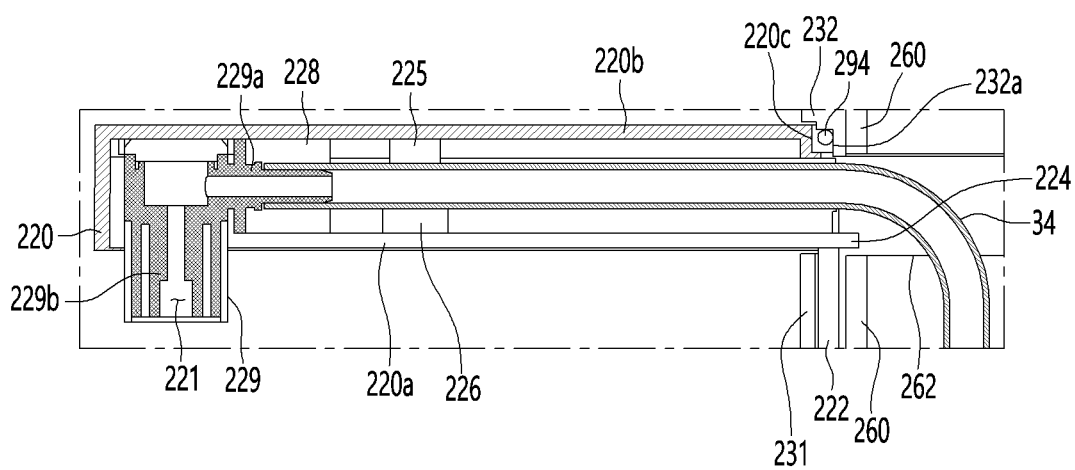
FIG. 14 is a schematic side view having partial cross-hatching added for clarity and illustrating a second liquid discharge nozzle that is a portion of components according to an embodiment.
Figure 15:
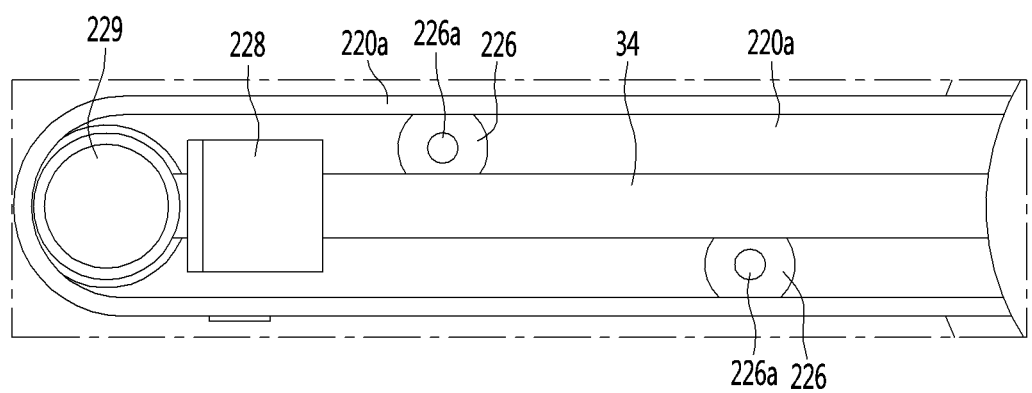
FIG. 15 is a view of the second liquid discharge nozzle from which an upper frame is removed when viewed from the upper side.
Figure 16:
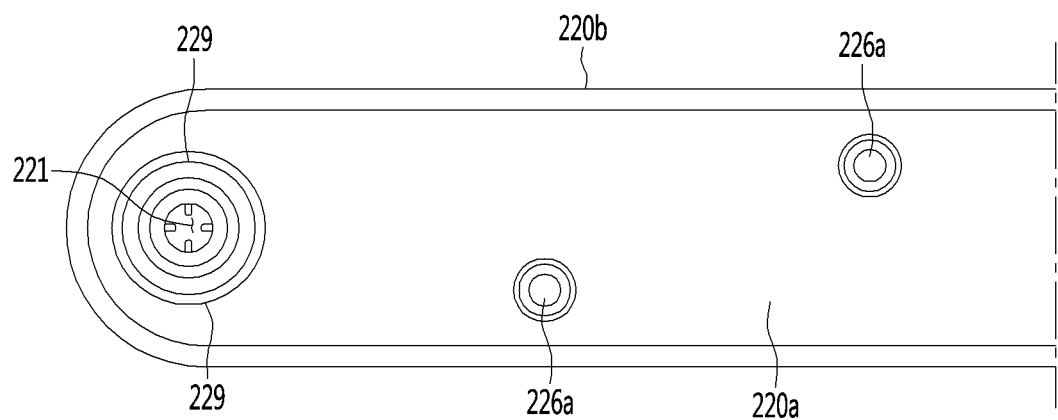
FIG. 16 is a view of the second liquid discharge nozzle when viewed from the lower side.
Figure 17:
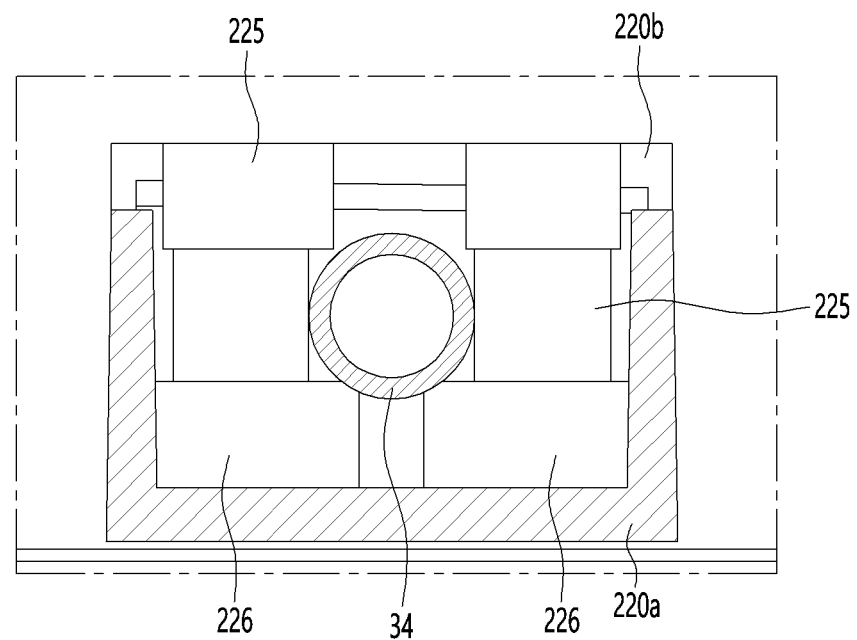
FIG. 17 is a schematic view having partial cross-hatching added for clarity and illustrating a state in which a sterilized liquid tube is fixed between the upper frame and a lower frame.
Figure 18:
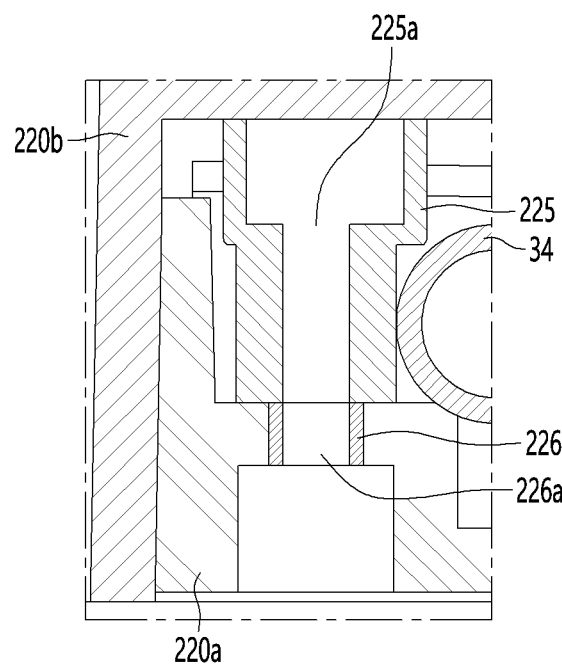
FIG. 18 is an enlarged schematic view having partial cross-hatching added for clarity and illustrating a portion of FIG. 17.

FIG. 14 is a cross-sectional view of a second liquid discharge nozzle 220 according to an embodiment. FIG. 15 is a view of the second liquid discharge nozzle 220 from which an upper frame is removed when viewed from the upper side. FIG. 16 is a view of the second liquid discharge nozzle 220 when viewed from the lower side. FIG. 17 is a cross-sectional view illustrating a state in which a sterilized liquid tube is fixed between the upper frame and a lower frame. FIG. 18 is an enlarged view illustrating a portion of FIG. 17.

Referring to FIGS. 14 to 18, like the first liquid discharge nozzle 210, the second liquid discharge nozzle 220 may also be limited in rotation angle. For example, the second liquid discharge nozzle 220 may rotate in a range of about 90 degrees to about 270 degrees. For this, a rotation limit structure for limiting the rotation angle of the second liquid discharge nozzle 212 is provided. In the case of the second liquid discharge nozzle 220, a second stopper 224 may be positioned on a rear end (a right side of FIG. 14) of a lower frame 220a defining the bottom surface of the second liquid discharge nozzle 220.

Also, the internal member 260 is provided with a rotation limit hole 262 into which the second stopper 224 is inserted. The rotation limit hole 262 may be opened in a circumferential direction of the internal member 260 and may be opened by an angle of about 120 degrees to about 180 degrees. Therefore, the second stopper 224 inserted into the rotation limit hole 262 may rotate only in a range of about 120 degrees to about 180 degrees, and as a result, the rotation angle of the second liquid discharge nozzle 220 may be limited to an angle of about 120 degrees to about 180 degrees. As described above, when the second liquid discharge nozzle 220 rotates, the internal member 260 is maintained in a fixed state.

Also, a fourth O-ring 294 may be inserted between a rear end (e.g., a right side of FIG. 14) of the upper frame 220b and an outer surface of a lower end of the second body 232 to prevent leakage and generate a rotational resistance. Also, a sidewall 220c is positioned on a rear end of the upper frame 220b so that the fourth O-ring 294 may be contacted and supported in a horizontal direction, and an extension surface extending in the horizontal direction may be positioned on a lower end of the sidewall 220c. Also, a side groove 232a may be defined in the lower end of the second body 232 so as to be recessed inward to accommodate the fourth O-ring 294. An upper side of the side groove 232a may be provided with an edge groove in which a portion of edges of the upper frame 220b is accommodated.

Also, support protrusions 225 and 226 protruding inward from the second liquid discharge nozzle 220 may be positioned on the lower frame 220a defining the bottom surface of the second liquid discharge nozzle 220 and the upper frame 220b defining the top surface of the second liquid discharge nozzle 220, respectively. The support protrusion 226 of the lower frame 220a protrudes upward, and the support protrusion 225 of the upper frame 220b protrudes downward. The support protrusions 225 and 226 may be positioned at positions facing each other. In addition, the support protrusions 225 and 226 may be adjacent to or in contact with each other.

Referring to FIG. 17, the support protrusions 225 and 226 may be positioned at both sides, respectively. The sterilized liquid tube 34 positioned inside the second liquid discharge nozzle 220 may be fixed between the support protrusions 225 and 226 while passing between the support protrusions 225 and 226.

Referring to FIG. 18, coupling holes 225a and 226a may be defined in the support protrusions 225 and 226, and the holes 225a and 226a may be coupled by bolts or screws. Here, the upper frame 220b and the lower frame 220a may be coupled to each other by coupling a screw or the like upward from the lower side of the second liquid discharge nozzle 220.

The upper frame 220b may be provided with a sidewall extending downward along the circumference of the top surface, and the lower frame 220a may be provided with a sidewall extending upward along the circumference of the lower surface. The upper frame 220b may define a concave space upward, and the lower frame 220a may define a concave space downward. The sidewall of the lower frame 220a is accommodated inside the sidewall of the upper frame 220b.

Thus, the lower frame 220a defining the bottom surface of the second liquid discharge nozzle 220 and the upper frame 220b defining the top surface of the second liquid discharge nozzle 220 may be integrally fixed. The coupling hole 226a may be defined to pass through the lower frame 220a. Accordingly, a bolt, screw, etc., is inserted into the coupling hole 226a at the lower side of the lower frame 220a to couple the coupling holes 225a and 226a of the respective support protrusions 225 and 226, thereby coupling the lower frame 220a to the upper frame 220b.

Also, a third O-ring 293 may be inserted between the outer surface of the internal member 260 and the inner surface of the second insertion part 222 to prevent shaking, prevent leakage, generate a rotational resistance, and improve a rotational manipulation feeling. Also, an O-ring insertion groove 263 into which the third O-ring 293 is inserted may be defined along the circumferential direction on the outer surface of the internal member 260.

Also, an interval between the internal member 260 and the second insertion part 222 of the second liquid discharge nozzle 220 may be maintained by the third O-ring 293. Also, the shaking of the second liquid discharge nozzle 220 may be prevented by the third O-ring 293. Also, a gap between the internal member 260 and the second insertion part 222 of the second liquid discharge nozzle 220 may be held by the third O-ring 293. Also, while friction is generated by the third O-ring 293, and the rotation of the second liquid discharge nozzle 220 is smoothly performed, the manipulation feeling may be improved, and the second liquid discharge nozzle 220 may be fixed to the rotating position.

Also, a second square ring 296 may be inserted between the outer surface of the internal member 260 and the inner surface of the first body 231 to prevent shaking, prevent leakage, generate a rotational resistance, and improve a rotational manipulation feeling. The friction occurs in the axial direction by the second square ring 296 to hold the second liquid discharge nozzle 220 without being shaken in the axial direction.

In this case, a lower end of the second insertion part 222 may be in contact with and supported on an upper side of the second square ring 296. Also, a square ring insertion groove 267 may be defined along the circumferential direction in the outer surface of the internal member 260. For example, a second square ring 296 may be inserted into the square ring insertion groove 267. In another example, a square ring support member 297 may be inserted into the square ring insertion groove 267.

The square ring support member 297 includes an insertion part 297c inserted into the square ring insertion groove 267. Also, the square ring support member 297 includes a square ring support part 297a extending in a horizontal direction from the lower end of the insertion part 297c to the outside to seat the second square ring 296.

Also, the square ring support member 297 may be provided with a vertical extension part 297d extending vertically downward from the outside of the square ring support part 297a. The vertical extension part 297d is fitted between the outer surface of the internal member 260 and the inner surface of the first body 231. The vertical extension part 297d may have an inclined surface 297b at a lower end of the inner surface facing the internal member 260. A thickness of the lower end of the vertical extension part 297d may be narrowed by the inclined surface 297b. Thus, the square ring support member 297 may be more easily inserted between the inner member 260 and the first body 231.

An interval between the internal member 260 and the first body 231 may be constantly maintained by the second square ring 296. For reference, the second square ring 296 may have a ring shape, and a cross-section thereof may have a quadrangular shape. Also, a lower end of the second insertion part 222 is supported by the square ring support member 297 and the second square ring 296 so that the second liquid discharge nozzle 220 is more stably fixed to rotate.

The second cock 229 may provide an inlet 229a extending in the horizontal direction and connected to the sterilized liquid tube 34 and to an outlet 229b communicating with the inlet 229a and extending in the vertical direction. The sterilized liquid tube 34 and the inlet 229a may be fixed to each other by a separate fixing cap 218 for pressing the sterilized liquid tube 34 in a state in which the sterilized liquid tube 34 is fitted to the outside of the inlet 229a.

Also, the sterilized liquid tube 34 and the inlet 229a may be coupled to each other in the thermal fusion manner. In this case, when the sterilized liquid tube 34 is replaced, the whole replacement may be performed up to the second cock 229.

For example, the second cock 229 and the sterilized liquid tube 34 may be installed and separated from the second liquid discharge nozzle while being integrally coupled to each other.

When being installed, the lower frame 220a defining the bottom surface of the second liquid discharge nozzle 220 is separated. Then, the second cock 229 and the sterilized liquid tube 34 are inserted from the opened lower side of the second discharge nozzle 220 to the upper side, and the sterilized liquid tube 34 is put into the rotation limit hole 262 so that the sterilized liquid tube 34 is inserted into the internal member 260. Then, the lower frame 220a is coupled to the second liquid discharge nozzle 220.

In contrast, during the separation, the lower frame 220a defining the bottom surface of the second liquid discharge nozzle 220 is separated. Then, the second cock 229 and the sterilized liquid tube 34 are withdrawn downward from the upper side of the second liquid discharge nozzle 220. Then, the sterilized liquid tube 34 is pulled through the rotation limit hole 262. Here, the sterilized liquid tube 34 is separated from the second liquid discharge valve. Then, after installing a new second cock 229 and sterile liquid tube 34, the lower frame 220a is coupled to the second liquid discharge nozzle 220.

Figure 19:
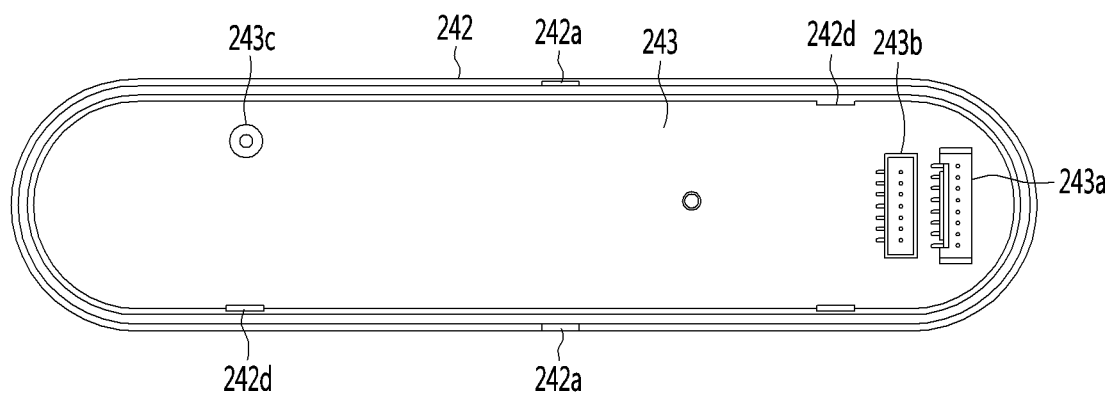
FIG. 19 is a view of the display and input part when viewed from a bottom surface.
Figure 20:
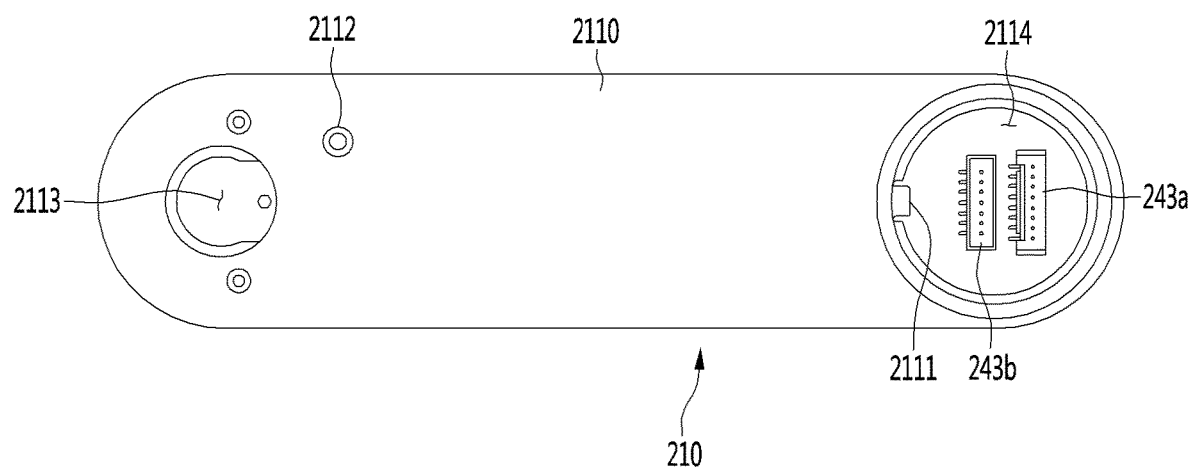
FIG. 20 is a view of the first liquid discharge nozzle when viewed from the lower side.
Figure 21:
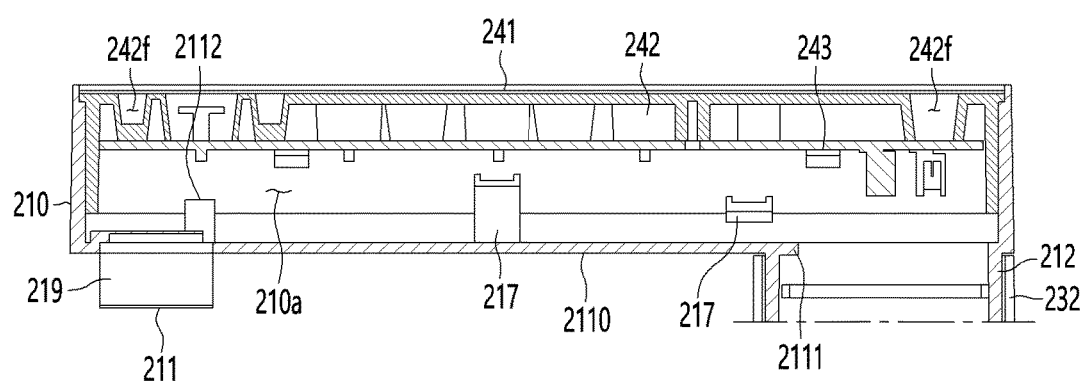
FIG. 21 is a schematic side view having partial cross-hatching added for clarity and illustrating the first liquid discharge nozzle.
Figure 22:
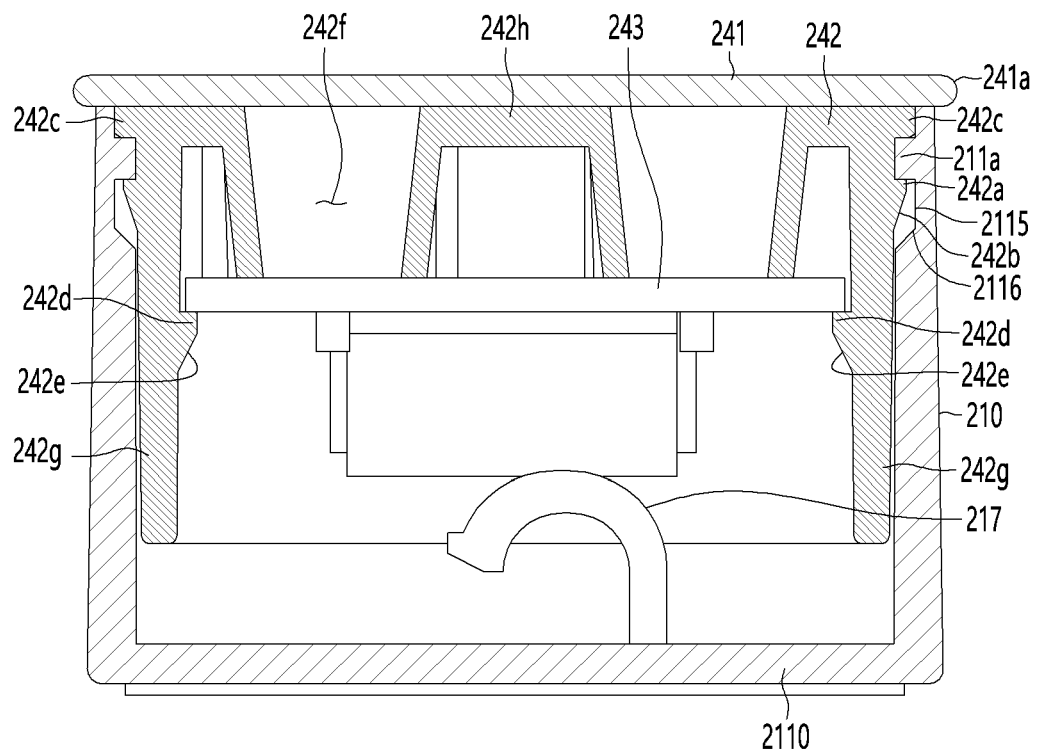
FIG. 22 is a schematic front view having partial cross-hatching added for clarity and illustrating the first liquid discharge nozzle.
Figure 23:
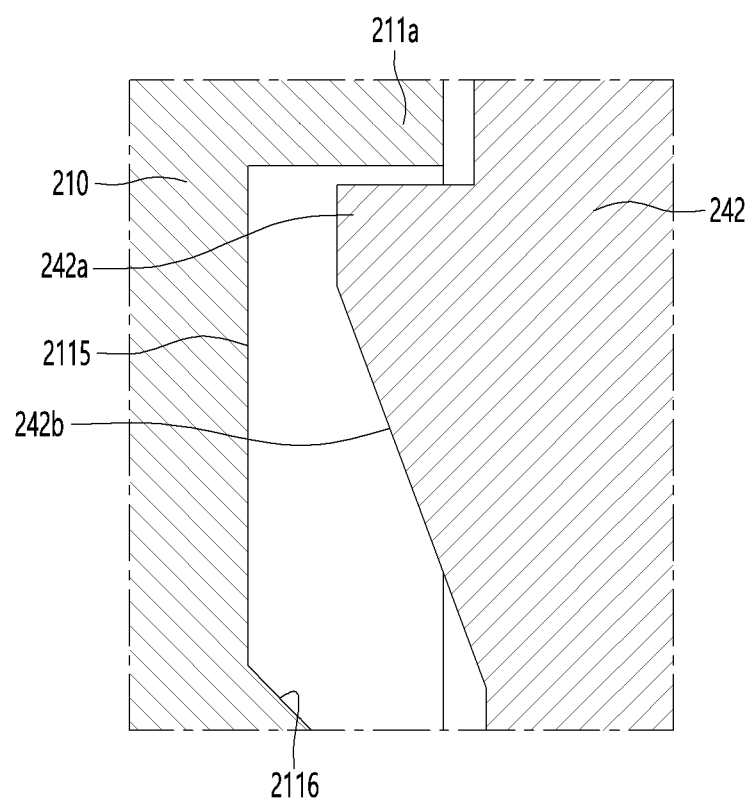
FIG. 23 is an enlarged schematic view having partial cross-hatching added for clarity and illustrating a portion of FIG. 22.

FIG. 19 is a view of the display and input part 240 when viewed from below. FIG. 20 is a view of the first liquid discharge nozzle 210 when viewed from the lower side. FIG. 21 is a side cross-sectional view of the first liquid discharge nozzle 210. FIG. 22 is a front cross-sectional view of the first liquid discharge nozzle 210. FIG. 23 is an enlarged view illustrating a portion of FIG. 22.

Referring to FIGS. 19 to 23, the display and input part 240 may be positioned above the first liquid discharge nozzle 210. Also, the display and input part 240 may be positioned above the second liquid discharge nozzle 220. The display and input part 240 may include a plate 241 positioned at the uppermost side and exposed to the outside, a frame 242 positioned below the plate 241, and a PCB 243 positioned below the frame 242.

Also, the plate 241 may be made of a transparent or translucent material. The PCB 243 may be provided with various display parts including an LED. Also, the PCB 243 may further include a switch, a touch sensor, and the like. Various connection terminals 243a and 243b may be positioned on the PCB 243. The connection terminals 243a and 243b may be positioned at positions overlapping the first insertion part 212 of the first liquid discharge nozzle 210 in the vertical direction. Therefore, the power line and various wire passing through the first insertion unit 212 may be easily coupled to the connection terminals 243a and 243b, and when the first liquid discharge nozzle 210 rotates, the twisting and entanglement may be prevented. Also, a plurality of holes may be defined in the frame 242 so that the display part, the switch, the touch sensor, and the like are exposed to the plate 241.

An adhesive layer is positioned on the bottom surface of the plate 241, and the plate 241 may adhere to a top surface of the frame 242 due to the adhesive layer. At least a portion of the frame 242 may be positioned on a plane to be in surface contact with the plate 241.

The first liquid discharge nozzle 210 may have an inner space 210a having an opened upper side and recessed from an upper side to a lower side. Also, the frame 242 and the PCB 243 may be accommodated in the inner space 210a defined in the first liquid discharge nozzle 210, and the plate 241 may cover the opened upper side of the first liquid discharge nozzle 210.

In this case, the plate 241 may have an area larger than the upper area of the first liquid discharge nozzle 210. Accordingly, a boundary portion 241a of the plate 241 may protrude outward from the first liquid discharge nozzle 210, and thus, a phenomenon in which the liquid or the foreign substance flows between the plate 241 and the first liquid discharge nozzle 210 may be prevented. That is, the liquidproof performance may be improved. The plate 241 may be fixed to the upper portion of the first liquid discharge nozzle 210 through adhesion or the like.

Also, the frame 242 may include a planar portion 242*h* and a sidewall 242*g* extending downward from a lower circumference of the planar portion 242*h*. Also, while the PCB 243 is accommodated in the sidewall 242*g*, the liquid-proofness of the PCB 243 may be secured. Also, the sidewall 242*g* may be provided with a plurality of hook parts 242*d* protruding inward from an inner surface thereof. The PCB 243 may be fixed to the frame 242 by the hook parts 242*d*.

The hook part 242*d* is positioned on a front end (e.g., left side of FIG. 19) and a rear end (e.g., right side of FIG. 19) below one side (see FIG. 19) of the sidewall 242*g* and is positioned on a rear end of the other side of the sidewall 242*g*. The hook part 242*d* may not positioned on the front end (left side of FIG. 19) of the other side (upper side of FIG. 19) of the sidewall 242*g*. When the PCB 243 is separated from the frame 242, the PCB 243 is pulled from a front end (left side of FIG. 19) of the other side (upper side in FIG. 19) at which the hook part 242*d* is not positioned to separate the PCB 243 from the frame 242. Also, the coupling holes 243*c* and 2112 to be described later may be defined in the front end (left side of FIG. 19) of the other side (upper side of FIG. 19) at which the hook part 242*d* is not positioned.

The PCB 243 may be assembled from the lower side to the upper side (see FIG. 22) of the frame 242. Also, the hook part 242*d* may be positioned to be inclined upward while a protruding thickness gradually increases from the lower side to the upper side. Thus, when the PCB 243 is inserted from the lower side to the upper side, both sides of the PCB 243 move along the inclined surface 242*e* of the hook part 242*d*, and then, when both sides of the PCB 243 are inserted into the upper end of the hook part 242*d*, the PCB 243 may be fixed to the frame 242.

Also, the frame 242 may be provided with a planar portion 242*h* connecting upper ends of both sidewalls 242*g* to each other. Also, the planar portion 242*h* may be provided with a plurality of opening grooves 242*f* that are opened in the vertical direction. A lower end of the planar portion 242*h* may be in contact with and supported above the PCB 243. Therefore, while the lower side of the PCB 243 is supported by the hook part 242*d*, and the upper side is supported by the lower end of the opening groove 242*f*, the PCB 243 is securely fixed to the frame 242.

Also, the coupling holes 243*c* and 2112 may be defined in corresponding positions of the lower frame 2110 of the PCB 243 and the first liquid discharge nozzle 210, and the coupling holes 243*c* and 2112 may be coupled through a bolt, a screw, and the like. In this case, the lower frame 2110 and the PCB 243 may be coupled to each other by coupling the screw or the like from the lower side of the first liquid discharge nozzle 210.

Also, the frame 242 may be provided with a coupling groove defined to be concave from the lower side to the upper side to couple the screw and the like passing through the coupling holes 243*c* and 2112. In this case, the coupling of the lower frame 2110, the PCB 243, and the frame may be more securely realized.

The lower frame 2110 of the first liquid discharge nozzle 210 has a cock hole 2113, in which the first cock 219 is installed, and a hollow 2114 in which the second common tube 39 is positioned. The hollow 2117 may be referred to as a hollow of the insertion part 212. Also, protrusions 211*a* protruding inward are positioned on inner surfaces of the first liquid discharge nozzles 210 that face each other. Also, the frame 242 is provided with a first protrusion 242*c* seated on an upper end of the protrusion 211*a*. The first protrusion 242*c* may have an inclined surface at an outer lower edge.

Also, a groove part 2115 having an inwardly concave shape may be defined in the inner side surfaces of the first liquid discharge nozzle 210 facing each other below the protrusion 219. The groove 2115 may have an inclined surface 2116 that is upwardly inclined outward at a lower end thereof.

Also, a pair of second protrusions 242*a* protruding outward may be positioned at both sides of the frame 242 to be inserted into the groove part 2115. The second protrusion 242*a* has a shape in which a thickness thereof gradually decreases from the upper side to the lower side. Therefore, the inclined surface 242*b* is positioned on an outer surface of the second protrusion 242*a*.

Therefore, when the frame 242 is assembled while being pressed from the upper side to the lower side of the first ejection nozzle 210, the inclined surface 242*b* descends while contacting the protruding portion 211*a*, and then when the inclined surface 242*b* is positioned below the protruding portion 211*a*, the frame 242 is hooked with the first liquid discharge nozzle 210 while the second protrusion 242*a* is accommodated in the groove part 2115.

In this embodiment, the display and input part 240 is positioned on the top surface of the first liquid discharge nozzle 210 that is accessible to the user. Therefore, when liquid splashes during the use of the liquid, such that liquid is introduced into the display and input part 240, a malfunction may occur.

To prevent this limitation, in this embodiment, the upper portion of the first liquid discharge nozzle 210 is opened, and the opened upper portion is configured to cover the plate 241. An internal space is defined between the plate 241 and the first liquid discharge nozzle 210, and an input touch sensor, a display LED, and the like are positioned in the internal space. Also, an outer side of the plate 241 is positioned to protrude more than the first liquid discharge nozzle 210, thereby ensuring the liquidproofness.

Also, the first liquid discharge nozzle 210 has a plurality of hose fixing hooks positioned inside and defines a hole. Therefore, when the display and input part 240 is separated from the first liquid discharge nozzle 210, the cock and the tube may be exposed upward, and the visit manager or the user may easily separate the tube and the cock and install a new tube and cock.

The display and input part 240 may be coupled to and separated from the upper side of the first liquid discharge nozzle 210 in a state of being coupled to a single module by screwing, adhesion, hook coupling, or the like. The display and input part 240 is separated from the first liquid discharge nozzle 210 when the screw is released from the lower side of the first liquid discharge nozzle 210. Then, the upper side of the first liquid discharge nozzle 210 is opened.

Figure 24:
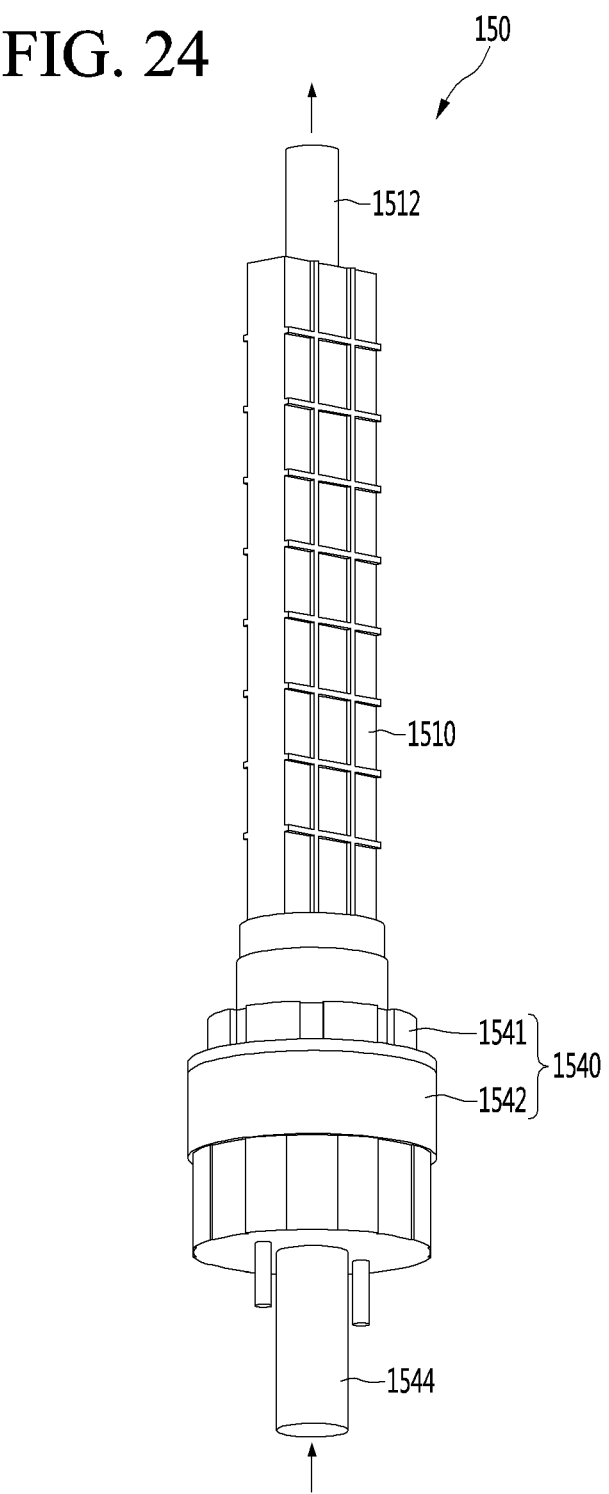
FIG. 24 is a perspective view of a sterilized liquid module that is a portion of the components according to an embodiment.
Figure 25:
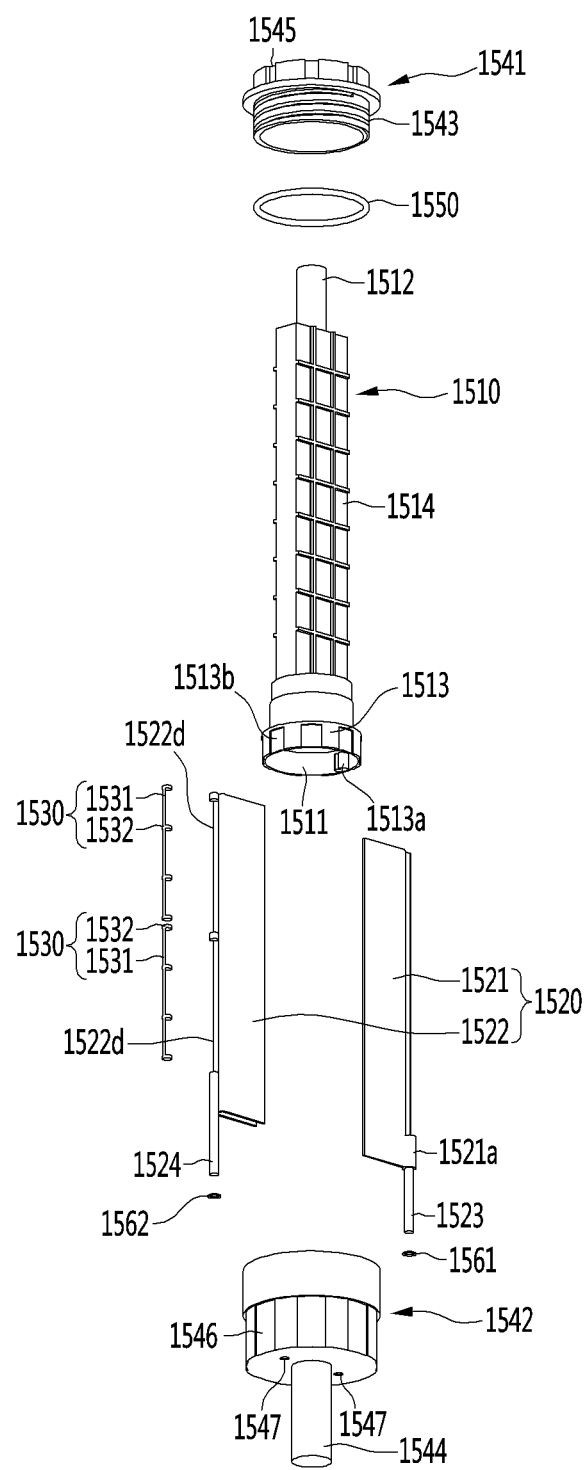
FIG. 25 is an exploded perspective view of the sterilized liquid module that is a portion of the components according to an embodiment.
Figure 26:
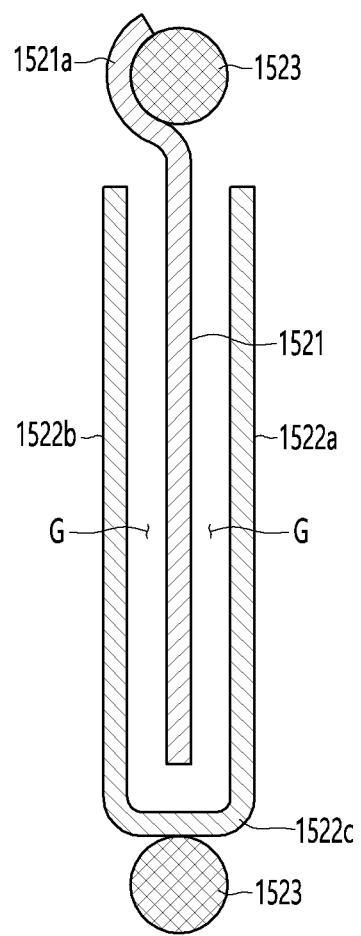
FIG. 26 is a schematic view having partial cross-hathing added for clarity and illustrating an electrode part provided in the sterilized liquid module that is a portion of the components according to an embodiment.

FIG. 24 is a perspective view of a sterilized liquid module 150 according to an embodiment. FIG. 25 is an exploded perspective view of the sterilized liquid module 150 according to an embodiment. FIG. 26 is a cross-sectional view of an electrode part provided in the sterilized liquid module 150 according to an embodiment.

Referring to the drawings, the sterilized liquid module 150 according to an embodiment includes a casing 1510, an electrode part 1520, a spacer 1530, and a cap 1540. First, the casing 1510 defines an outer body of the sterilized liquid module 150.

A space into which the electrode part 1520 and the spacer 1530 are accommodated is defined inside the casing 1510. One side of the casing 1510 is opened to define an opening 1511, and the other side of the casing 1510 is provided with a discharge tube 1512 through which the sterilized liquid is discharged. The casing 1510 may have a box shape in which at least part thereof is flat. At least a portion of the casing 1510 may have a box shape having a long length.

A thickness or width of the inner space defined by the casing 1510 may have a constant size along the longitudinal direction so that a constant liquid pressure is maintained while the liquid is introduced and discharged.

The opening 1511 of the casing 1510 may be covered by the cap 1540. For example, a cylindrical inflow part (or inflow tubing) 1513 may be provided in one end of the casing 1513 having the opening 1511, and the cap 1540 may also have a cylindrical shape. The cap 1540 surrounds the inflow part 1513 of the casing 1510 in which the opening 1511 is defined and may be coupled to the casing 1510. The inflow part 1513 may have a stair shape while gradually increasing in outer diameter from the upper side to the lower side. A plurality of grooves 1513b may be defined in an outer side of an end of the inflow part 1513.

On the other hand, the cap 1540 may be constituted by an upper cap 1541 and a lower cap 1542. The upper cap 1541 may have a hollow shape so that at least a portion of the casing 1510 passes therethrough. The upper cap 1541 may be fitted downward from the upper side (see FIG. 25) in which the discharge tube 1512 of the casing 1510 is positioned. Also, the upper cap 1541 may be seated on the upper side of the inflow part 1513 in a manner of surrounding the inflow part 1513 from above.

The lower cap 1542 is coupled to the upper cap 1541 while covering the opening 1511 from the lower side of the casing 1510. For example, a screw thread 1543 may be positioned on an outer circumferential surface of the lower side of the upper cap 1541. Also, a screw thread may be positioned on the inner circumferential surface of the upper end of the lower cap 1542 to which the screw thread 1543 of the upper cap 1541 is coupled.

When the upper cap 1541 and the lower cap 1542 are coupled to each other as described above, the opening 1511 of the casing 1510 may be covered by the cap 2540. Also, an O-ring 1550 for the sealing may be inserted between the upper cap 1541 and the lower cap 1542 or between the casing 1510 and the cap 1540.

The lower cap 1542 may be provided with an inflow tube 1544 through which the purified liquid supplied from the sterilized liquid tube 34 is introduced. The inflow tube 1544 may be connected to the filter-side sterilized liquid tube, and the discharge tube 1512 may be connected to the sterilized liquid tube of the liquid discharge part 200.

Also, an outer surface of the upper cap 1541, and an outer surface of the lower cap 1542 may have anti-slip unevenness 1545 and 1546 to prevent the user's hand from slipping, respectively. A groove and protrusion may be alternately positioned on the outer surface of the upper cap 1541 and the outer surface of the lower cap 1542 along the circumferential direction to provide the anti-slip unevenness 1545 and 1546.

Also, the casing 1510 may include a plurality of reinforcing ribs 1514 integrated with the outer surface thereof.

The casing 1510 may have flat surfaces facing each other. The plurality of reinforcing ribs 1514 provided on the outer surface of the casing 1510 may include a plurality of transverse reinforcing ribs and a longitudinal reinforcing rib. The plurality of longitudinal reinforcement ribs and the plurality of transverse reinforcing ribs may cross each other to provide a lattice pattern. With the configuration of the plurality of reinforcing ribs 1514 as described above, pressure resistance performance of the casing 1510 may be further improved.

An outer appearance of the sterilized liquid module 150 is defined by the casing 1510 and the cap 1540 as described above. The sterilized liquid module 150 may be positioned so that the inflow tube 1544 faces downward and the discharge tube 1512 faces upward. Accordingly, the liquid obtained through the inflow tube 1544 may flow upward from the inner lower portion of the casing 1510. The discharge tube 1512 may be positioned above the casing 1510, and the sterilized liquid may be discharged to the outside of the casing 1510 through the discharge tube 1512.

The inflow tube 1544 and the discharge tube 1512 are connected to the sterilized liquid tube 34, respectively. Thus, the purified liquid introduced into the sterilized liquid tube 34 is introduced into the sterilized liquid module 150 through the inflow tube 1544, and the sterilized liquid generated in the sterilized liquid module 150 is discharged from the sterilized liquid module 150 through the discharge tube 1512 and then supplied to the liquid discharge part 200 through the sterilized liquid tube 34.

As described above, when the discharge tube 1512 positioned below the inflow tube 1544 through which the purified liquid flows, and the sterilized liquid is discharged is provided at the upper side, the liquid slowly flows from the lower side to the upper side, and bubbles generated in the process of generating the sterilized liquid are collected to an upper side and then discharged to the discharge tube 1512. If the inflow tube 1544 is positioned above the casing 1510, the liquid obtained through the inflow tube 1544 quickly flows downward by the gravity, and the purified liquid is discharged without sufficiently reacting with the electrode part 1520. As a result, it is difficult to secure a desired sterilized liquid concentration.

When the inflow tube 1544 and the discharge tube 1512 are positioned in the horizontal direction, the air bubbles generated during the sterilized liquid generation process are not smoothly discharged, resulting in low efficiency of the sterilized liquid generation. To prevent such a limitation, the inflow tube 1544 and the discharge tube 1512 are arranged in the vertical direction. Here, the sterilized liquid tube 150 is installed so that the inflow tube 1544 is positioned at the lower side, and the discharge tube 1512 is positioned at the upper side.

As a result, a contact area between the liquid and the electrode part 1520 is expanded while a liquid level gradually increases from the lower side to increase in sterilized liquid generation efficiency due to chemical reaction between the electrode part 1520 and the liquid. A passage through which liquid flows along the longitudinal direction of the casing 1510 is provided inside the casing 1510.

In the casing 1510, two electrode parts 1520 may be positioned to overlap each other. Also, a spacer 1530 may be provided inside the casing 1510 to maintain an interval between the two electrode parts 1520. The electrode parts 1520 include a first electrode 1521 and a second electrode 1522. The casing 1510 may be provided with one or more holders for holding at least a portion of the first electrode 1521 and the second electrode 1522 fixed to an inner surface thereof. For example, each of the first electrode 1521 and the second electrode 1522 may be provided in a plate shape. In another example, the first electrode 1521 may be provided in a plate shape, and the second electrode 1522 may have a folded shape facing one side and the other side. The second electrode 1522 may have a cross section of a "U" shape.

The second electrode 1522 may include a pair of electrode plates 1522a and 1522b facing each other and a bent portion 1522c connecting sides of the electrode plates 1522a and 1522b to each other. At least one slit 1522d having a cutoff shape may be defined in the bent portion 1522a. The first electrode 1521 may be positioned between the electrode plates 1522a and 1522b. The electrode plates 1522a and 1522b and the first electrode 1521 are positioned in parallel to each other and are spaced apart from each other. That is, a gap G is defined between the electrode plates 1522a and 1522b and the first electrode 1521.

Also, to maintain the gap G formed between the electrode plates 1522a and 1522b and the first electrode 1521 as described above, a spacer 1530 is inserted between the electrode plates 1522a and 1522b and the first electrode 1521 or between the electrode plates 1522a and 1522b. The spacer 1530 may be provided in plurality. The spacer 1530 may be inserted into the slit 1522d. For example, two slits 1522d may be spaced apart from each other in the longitudinal direction, and two spacers 1530 may be provided corresponding to the slits 1522d.

The spacer 1530 has a central portion 1531 defined in parallel with the longitudinal direction of the electrode 1520 and a plurality of protrusions, each of which has a thickness greater than that of the central portion 1531 and spaced apart from each other along the longitudinal direction of the central portion 1531. For example, the protrusion 1532 may be fitted between the electrode plates 1522a and 1522b to maintain the gap between the electrode plates 1522a and 1522b. In another example, the protrusion 1532 may be fitted between the electrode plates 1522a and 1522b and the first electrode 1521 to maintain the gap between the electrode plates 1522a and 1522b and the first electrode 1521.

As described above, when the spacer 1530 is positioned between the central portion 1531 and the protrusion 1532, the liquid may flow between the protrusions 1532 while maintaining the gap between the electrodes 1521 and 1522 to reduce flow resistance. Also, the terminal parts 1523 and 1524 may be positioned on the first electrode 1521 and the second electrode 1522, respectively. The first electrode 1521 may protrude to surround at least a portion of the terminal part 1523, and a grip part 1521a having a curved surface may be provided. The terminal parts 1523 and 1524 may be exposed to the outside through the lower cap 1542. The terminal parts 1523 and 1524 may be positioned to be parallel to each other.

The inflow part 1513 of the casing 1513 may be provided with a fitting part 1513a to which the terminal parts 1523 and 1524 are fixed. Also, a through-hole 1547 through which the terminal parts 1523 and 1524 pass may be defined in the lower cap 1542. Also, O-rings 1561 and 1562 may be inserted between the through holes 1547 and the terminal parts 1523 and 1524 to prevent the leakage.

The first electrode 1521 and the second electrode 1522 receive power from the outside through the terminal parts 1523 and 1524 exposed to the outside of the lower cap 1542 to electrolyze the liquid (purified liquid) in which chlorine ions are dissolved to generate hypochlorous acid liquid having bactericidal power. The hypochlorous acid liquid contains a large amount of bubbles and is clouded due to its characteristics. Therefore, the user may visually check the sterilized liquid containing a lot of bubbles and distinguish the purified liquid from the sterilized liquid. In this case, a concentration of the sterilized liquid may be set in a range in which an accident does not occur when the user drinks the sterilized liquid.

Also, the first electrode 1521 and the second electrode 1522 are positioned to face each other on both sides of a solid polymer electrolyte layer and induce an electrolysis reaction in liquid to generate a high concentration of ozone, thereby generating the sterilized liquid having strong sterilizing power. As described above, the terminal parts 1523 and 1524 are provided at the two electrodes 1521 and 1522, and an external power source (current) may be applied to the electrodes 1521 and 1522 through the terminal parts 1523 and 1524. Each of the terminal parts 1523 and 1524 may protrude in the same direction from one side of each electrode 1521 and 1522 and may extend to protrude outward through the lower cap 1542. Also, each of the terminal parts 1523 and 1524 may be spaced apart from each other in the horizontal direction (width direction) of the electrodes 1521 and 1522.

As described above, when the electrode part 1520 is provided with a flat plate-shaped first electrode 1521 and a folded second electrode 1522, a size of the electrode part 1520 may decrease, and consequently, the sterilized liquid module 150 may decrease in size. On the other hand, since the second electrode 1522 has a folded shape, and the first electrode 1521 is positioned between the electrode plates 1522a and 1522b of the second electrode 1522, a contact area between the liquid and the electrodes 1521 and 1522 may increase, and further, the chemical reaction between the electrodes 1521 and 1522 and liquid may efficiently increase.

For reference, the first electrode 1521 and the second electrode 1522 may be applied on the opposite surface to provide a coating layer. For example, the first electrode 1521 and the second electrode 1522 may be made of a titanium (Ti) material. The coating layer may be provided as a mixture of iridium (Ir) and platinum (Pt). Each of the first electrode 1521 and the second electrode 1522 may have a thickness of about 0.5 mm, and the coating layer may have a thickness of about 1.6 μm. The coating layer may be positioned on both surfaces of the first electrode 1521. The coating layer may be positioned on inner surfaces of the second electrode 1522 facing each other.

In the sterilized liquid module 150 as described above, the generated sterilized liquid is provided to the sink through the second liquid discharge nozzle 210, and the user may perform cleaning dishes and cleaning fruits using the sterilized liquid.

Hereinafter, an arrangement and coupling structure of the controller for controlling the sterilized liquid module and the valve will be described.

Figure 27:
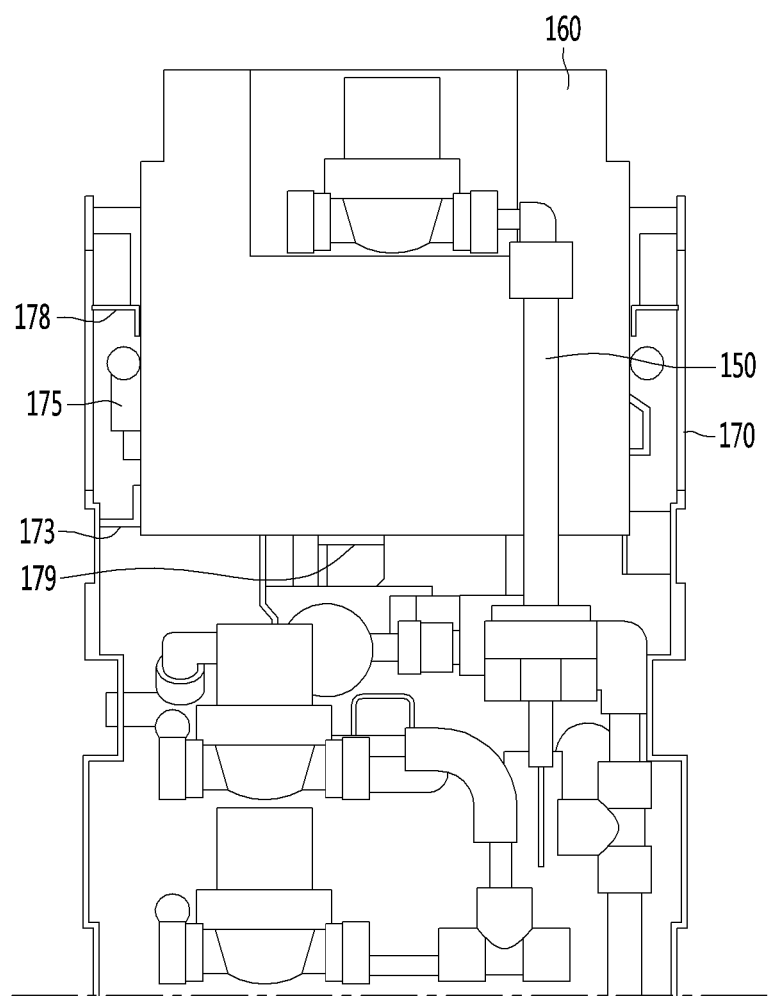
FIG. 27 is a front view illustrating a state in which the sterilized liquid module and the controller are coupled to a filter bracket.
Figure 28:
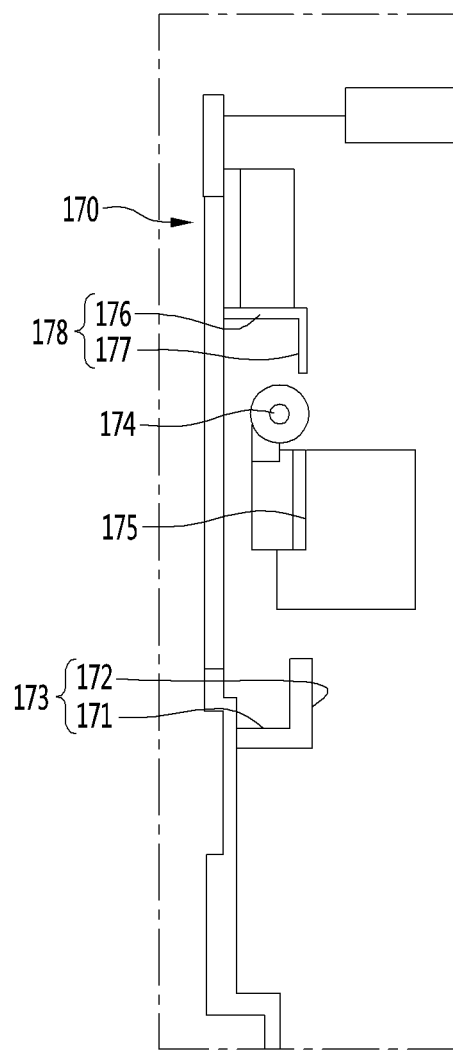
FIG. 28 is a front view illustrating a portion of the filter bracket.

FIG. 27 is a front view illustrating a state in which the sterilized liquid module and the controller are coupled to a filter bracket. FIG. 28 is a front view illustrating a portion of the filter bracket. Referring to FIGS. 27 and 28, the housing 110 includes a filter bracket 170 on which various valves are mounted. The filter bracket 170 may be positioned inside the housing 110 to be adjacent to the front cover 113 (see FIG. 1) defining the front surface of the housing 110.

The filter 120 is coupled to the lower side of the filter bracket 170, and the controller 160 for the control of the sterilized liquid module 150 may be coupled to the upper side. The controller 160 may be detachably coupled to the filter bracket 170. The controller 160 may include a box-shaped case. For example, the filter bracket 170 and the controller 160 may be provided with screw coupling holes 174 in positions facing each other, and the filter bracket 170 and the controller may be coupled in a screw coupling manner. In this case, a protrusion protruding outward on one side or both sides is positioned on the controller 160, and a coupling hole may be defined on the protrusion.

For another example, a first extension protrusion including a first extension part 171 extending in the horizontal direction from an inner surface of the filter bracket 170 and a second extension part 172 extending vertically from an end of the first extension part may be positioned on the filter bracket 170. The second extension part 172 may support one side of the controller 160 while contacting a lower side of one side of the controller 160.

Also, a second extension protrusion 178 including a third extension part 176 extending in a horizontal direction from an inner surface of the filter bracket 170 and positioned above the first extension part and a fourth extension part 177 extending vertically downward from an end of the third extension part 176 may be positioned on the filter bracket 170. The fourth extension part 172 may support one side of the controller 160 while contacting an upper side of one side of the controller 160.

The first extension protrusion 173 and the second extension protrusion 178 may be positioned on opposite sides of the filter bracket 170 so as to be symmetrical with each other. Also, the filter bracket 170 may include a support protrusion 179 extending toward the front side provided with the front cover 113 (see FIG. 1) to support the lower side of the controller 160.

Thus, the controller 160 may be positioned and coupled to the upper side of the filter bracket 170. That is, the filter 120 is mounted on the lower side of the filter bracket 170, and the controller 160 (PCB assembly) that provides an electrical signal to a bacteria module 150 and the sterilized liquid module 150 is mounted above the filter bracket 170.

While adding the sterilized liquid discharge function to a liquid purifier in one example, the controller 160 (PCB assembly) provides electrical signal to the sterilized liquid module 150 and is positioned in the housing 110. In this liquid purifier, a volume of the sterilized liquid module 150 is minimized to add the sterilized liquid module 150 and the controller 160 (PCB assembly) without structurally large changes, and the sterilized liquid discharge passage is added. Also, while the purified liquid passes through the sterilized liquid module 150, platinum and iridium are applied on an electrode of titanium material inside the sterilized liquid module 150 to form the sterilized liquid and generate the hypochlorous acid.

In this embodiment, to mount the sterilized liquid module 150 and the controller 160 (PCB assembly) for applying an electrical signal to the sterilized liquid module 150 in the housing 110, only a mold of the filter bracket 170 used in the existing liquid purifier may be modified to simply realize a structure in which the sterilized liquid module 150 and the controller 160 (PCB assembly) are seated and coupled. Also, a length of the passage connecting the filter 120 to the sterilized liquid module 150 may be minimally set.

Figure 29:
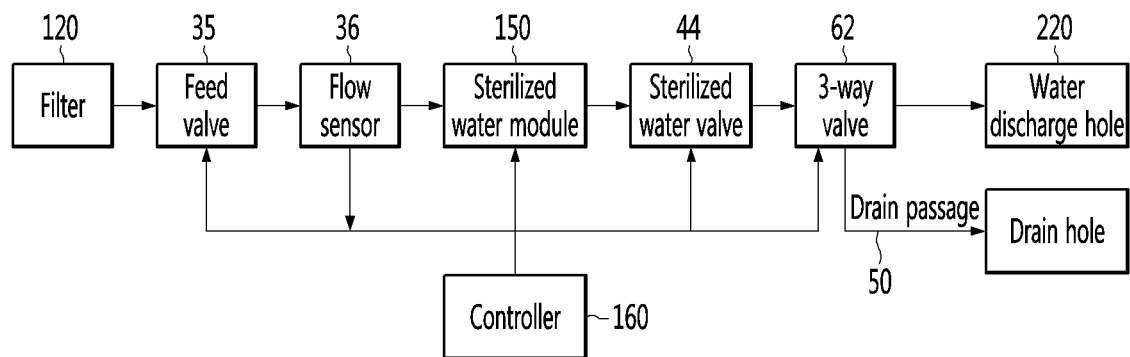
FIG. 29 is a block diagram illustrating a configuration for explaining a process of discharging sterilized liquid in the liquid dispensing device according to an embodiment.
Figure 30:
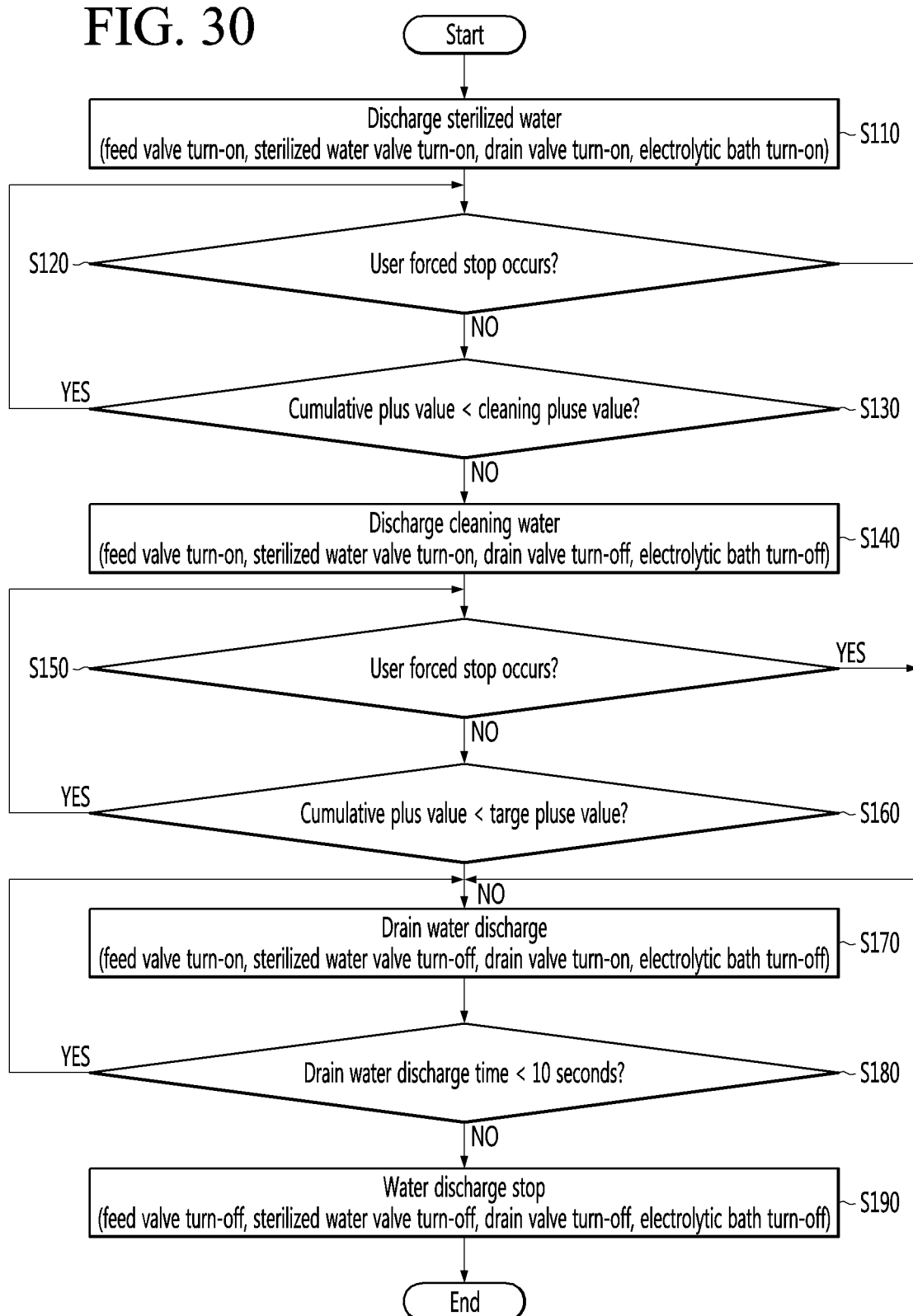
FIG. 30 is a flowchart illustrating a method for controlling discharging of sterilized liquid in the liquid dispensing device according to an embodiment.
Figure 31:
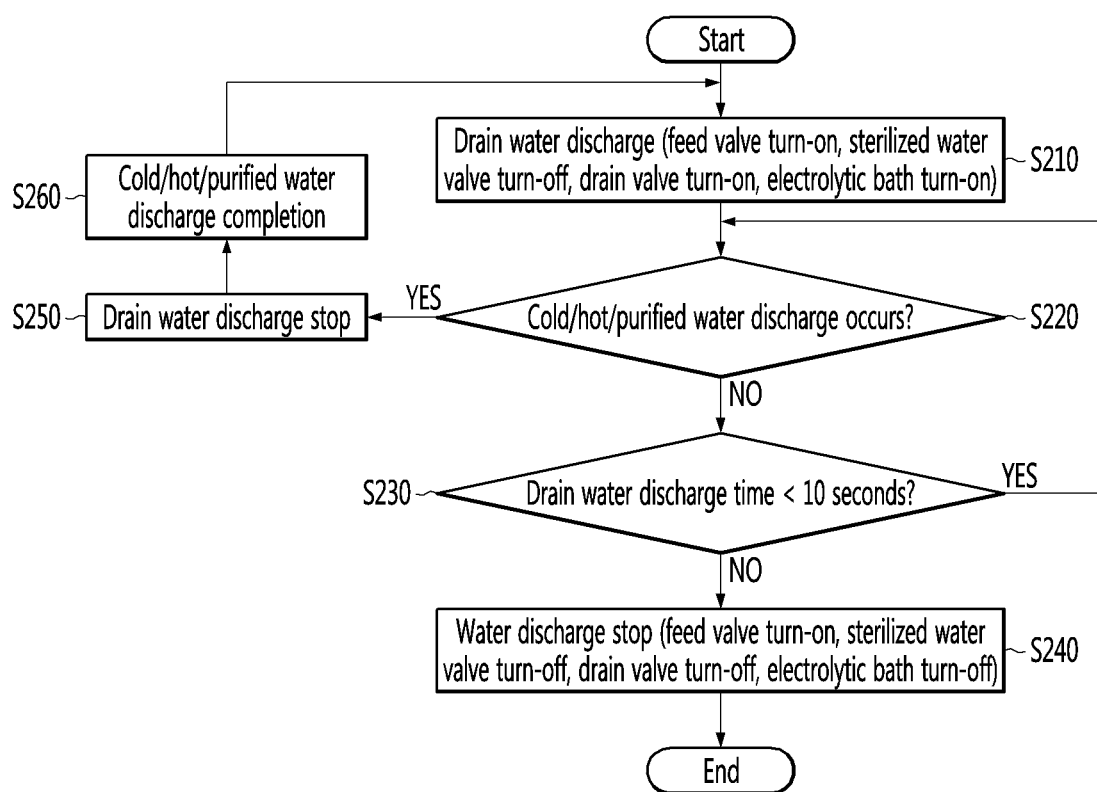
FIG. 31 is a flowchart for explaining a method for controlling discharging of sterilized liquid in the liquid dispensing device according to another embodiment.

FIG. 29 is a block diagram illustrating a configuration for explaining a process of discharging sterilized liquid in the liquid dispensing device according to an embodiment. FIG. 30 is a flowchart illustrating a method for controlling the discharging of the sterilized liquid in the liquid dispensing device according to an embodiment. FIG. 31 is a flowchart for explaining a method for controlling the discharging of the sterilized liquid in the liquid dispensing device according to another embodiment.

First, referring to FIG. 29, raw liquid passes through a filter 120, and purified liquid passes through an inflow valve 35 and a flow sensor 36 and then flows into a sterilized liquid module 44. The purified liquid passing through the sterilized liquid module 44 is changed into sterilized liquid, as previously described, and the sterilized liquid discharged from the sterilized liquid module 44 flows into a second liquid discharge valve 62.

Thereafter, according to the opened position of the second liquid discharge valve 62, the sterilized liquid introduced into the second liquid discharge valve 62 is introduced into a liquid discharge part 200 and then supplied to a user through a second liquid discharge nozzle 220 or is discarded to a drain hole through a drain tube 50. The second liquid discharge valve 62 is opened and closed by a controller 160. In detail, when the controller 160 triggers an opening of a first outlet connected to the second liquid discharge nozzle 220, the second liquid discharge valve 62 opens the first outlet connected to the second liquid discharge nozzle 220 to supply the introduced sterilized liquid to the second liquid discharge nozzle 220. On the other hand, in detail, when the controller 160 initiates an opening of the second outlet connected to the drain tube 50, the second liquid discharge valve 62 opens the second outlet connected to the drain tube 50 to supply the sterilized liquid to the drain tube 50.

As described above, when generating the sterilized liquid by electrolysis of the purified liquid through the sterilized liquid module 150, after discharging the sterilized liquid, hypochlorous acid liquid may remain in the casing 1510 or the electrode portion 1520, and the like. As a result, electrolytic performance may be reduced. Also, undesirable changes such as discoloration and corrosion may occur in the sterilized liquid module 150, the sterilized liquid tube 34, the second liquid discharge valve 62, and the second liquid discharge nozzle 220.

In detail, as illustrated in Formula 1 below, manganese ions (Mn 2+) contained in liquid are rapidly precipitated in the form of manganese oxide.

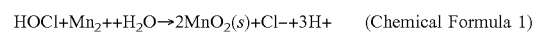

$$HOCl + Mn_2{++} H_2O \rightarrow 2MnO_2(s) + Cl{-} + 3H+ \quad \text{(Chemical Formula 1)}$$

Therefore, after the sterilized liquid is discharged, it is necessary to clean and drain the sterilized liquid module 150, the sterilized liquid tube 34, the second discharge nozzle 220, and the like.

FIG. 30 illustrates a method for controlling the cleaning of the sterilized liquid module 150. Referring to FIG. 30, first, when a user requests sterilized liquid discharge, the sterilized liquid may be discharged (S110). At this time, an amount of sterilized liquid one time may be automatically set to a reference value.

Here, an inflow valve 35 and a sterilized liquid valve 44 are opened, and a second liquid discharge valve 62 covers a second outlet connected to a drain tube 50 and opens a first outlet connected to a second liquid discharge nozzle 220. Then, power is supplied to the sterilized liquid module 150. Accordingly, the purified liquid passing through the filter 120 passes through the sterilized liquid module 150 and then is converted into the sterilized liquid so as to be supplied to the second liquid discharge nozzle 220, and the user may receive the sterilized liquid.

Thereafter, it is determined whether a forced stop command is generated from the user (S120). In operation S120, if the forced stop occurs, a process (S190) of proceeding to the drain to be described is performed. On the other hand, in operation S120, if the forced stop does not occur, an amount of cleaning liquid (cumulative pulse value) discharged to the second liquid discharge nozzle 220 is compared to a preset reference value (cleaning pulse value).

In operation S130, if the amount of the discharged wash liquid (cumulative pulse value) exceeds the preset reference value (cleaning pulse value), the generation of the sterilized liquid is stopped, the purified liquid introduced into the sterilized liquid module 150 is supplied to the user in the form of purified liquid (S140).

Here, the inflow valve 35 and the sterilized liquid valve 44 are opened, and the second liquid discharge valve 62 covers the second outlet connected to the drain tube 50 and opens the first outlet connected to the second liquid discharge nozzle 220. Then, the power supply to the sterilized liquid module 150 is cut off.

Thereafter, it is determined whether the forced stop command is generated from the user (S150). In operation S150, if the forced stop occurs, a process (S190) of proceeding to the drain to be described is performed. On the other hand, in operation S150, if the forced stop does not occur, an amount (cumulative value) of the purified liquid discharged to the second liquid discharge nozzle 220 is compared to a predetermined target value (S160). In operation S160, if the amount of discharged liquid (cumulative pulse value) exceeds the predetermined target value (target pulse value), the discharging of the purified liquid to the second liquid discharge nozzle 220 is stopped and the draining is performed (S170).

Here, the inflow valve 35 and the sterilized liquid valve 44 are covered, and the second liquid discharge valve 62 covers the second outlet connected to the drain tube 50 and covers the first outlet connected to the second liquid discharge nozzle 220. Then, the power supply to the sterilized liquid module 150 is cut off.

Then, it is determined whether the drain is performed for a predetermined reference time (S180). For example, the reference time may be set to about 10 seconds. Thereafter, when it is determined that the drain is performed for the reference time, the drain is stopped (S190). In this case, the inflow valve 35 and the sterilized liquid valve 44 are also covered, and the second outlet of the second liquid discharge valve 62, which is connected to the drain tube 50 is covered to cover the first outlet connected to the second liquid discharge nozzle 220. Then, the power supply to the sterilized liquid module 150 is maintained in a cutoff state.

According to the above, after the discharging of the sterilized liquid is completed, the purified liquid is supplied to the second discharge nozzle 220, and the cleaning of the tube connecting between the sterilized liquid module 150 and the second discharge nozzle 220 is performed to clean the second liquid discharge nozzle 220. Therefore, discoloration of the passage due to MnO$_2$ may be prevented. Also, as the drain is performed, the remaining liquid of the sterilized liquid module 150 and the sterilized liquid tube 44 may be discharged to the drain through the drain tube 50.

For example, the amount of liquid discharged once in the cleaning liquid may be set to about 120 ml, about 500 ml, or about 1000 ml. Also, when the amount of liquid discharged once is about 120 ml, the reference value (pulse value) may be set to about 205, and the target value (pulse value) may be set to about 248. Also, when the amount of liquid discharged once is about 500 ml, the reference value (pulse value) may be set to about 849, and the target value (pulse value) may be set to about 999. Also, when the amount of liquid discharged once is about 1000 ml, the reference value (pulse value) may be set to about 1848, and the target value (pulse value) may be set to about 1998.

Although not shown in the drawings, the sterilized liquid module 150 is drained, and then, while allowing the purified liquid passing through the filter to flows from the sterilized liquid module 150 to the drain tube 50, a reverse process of reversely applying the current direction to each electrode 1521 and 1522 may be performed to secure reliability of the electrodes 1521 and 1522. Also, after the reverse process as described above, the additional drain may be optionally performed. Further, the sterilized liquid may be produced for a period of time with the current direction reversed.

FIG. 31 illustrates a method for controlling the drain. Referring to FIG. 31, first, the drain is performed (S210). The drain as described above may be performed by an operation by a user or may be performed automatically.

In the latter case, an amount of cleaning liquid and purified liquid discharged to the second liquid discharge nozzle 220 (cumulative value) exceeds the preset target value, the cleaning liquid or the discharging of purified liquid to the second liquid discharge nozzle 220 is stopped, and the drain is performed automatically. In operation S210, the inflow valve 35 and the sterilized liquid valve 44 are opened, and the second liquid discharge valve 62 opens the second outlet connected to the drain tube 50 and covers the first outlet connected to the second liquid discharge nozzle 220. Then, the power supply to the sterilized liquid module 150 is blocked.

In the process of the draining as described above, the controller determines whether there is cold liquid, hot liquid, purified liquid discharge is requested from the user (S220). If, in operation S220, it is determined that the cold liquid, hot liquid, purified liquid discharge command is generated from the user, the drain is stopped (S250). Then, the cold liquid, the hot liquid, or the purified liquid is discharged according to the user's request (S260).

On the other hand, in operation S220, if the cold liquid, hot liquid, purified liquid discharge command by the user does not occur, it is determined whether the drain is performed for a predetermined reference time (S230). For example, the reference time may be set to about 10 seconds.

Thereafter, when it is determined that the drain is performed for the reference time, the drain is stopped (S240). In this case, the inflow valve 35 and the sterilized liquid valve 44 are also covered, and the second outlet of the second liquid discharge valve 62, which is connected to the drain tube 50 is covered to cover the first outlet connected to the second liquid discharge nozzle 220. Then, the power supply to the sterilized liquid module 150 is maintained in the blocked state.

According to the above, when the cold/hot/purified liquid discharge request from the user occurs in the process of the drain, the drain is stopped so that the cold/hot/purified liquid discharge is immediately stopped according to the user's request. Thus, the user may immediately receive the purified liquid having a desired temperature regardless of whether it is drained or not, thereby increasing in user's satisfaction.

Figure 32:
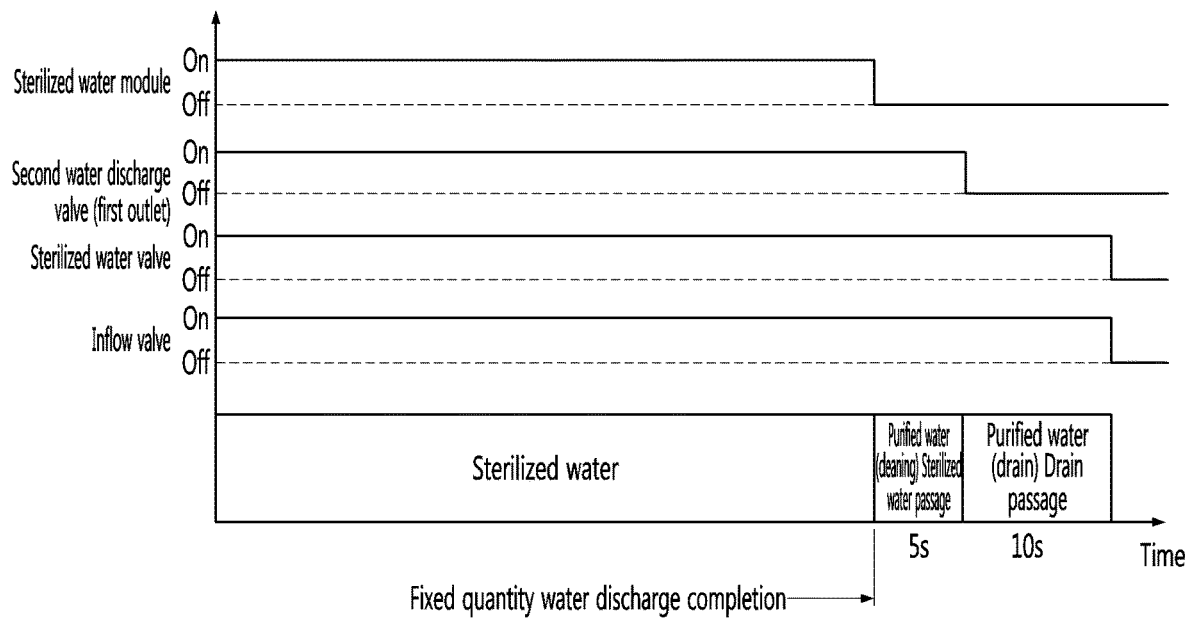
FIG. 32 is a timing view illustrating operation states of a sterilized liquid module and each of valves when a fixed quantity of sterilized liquid is discharged.
Figure 33:
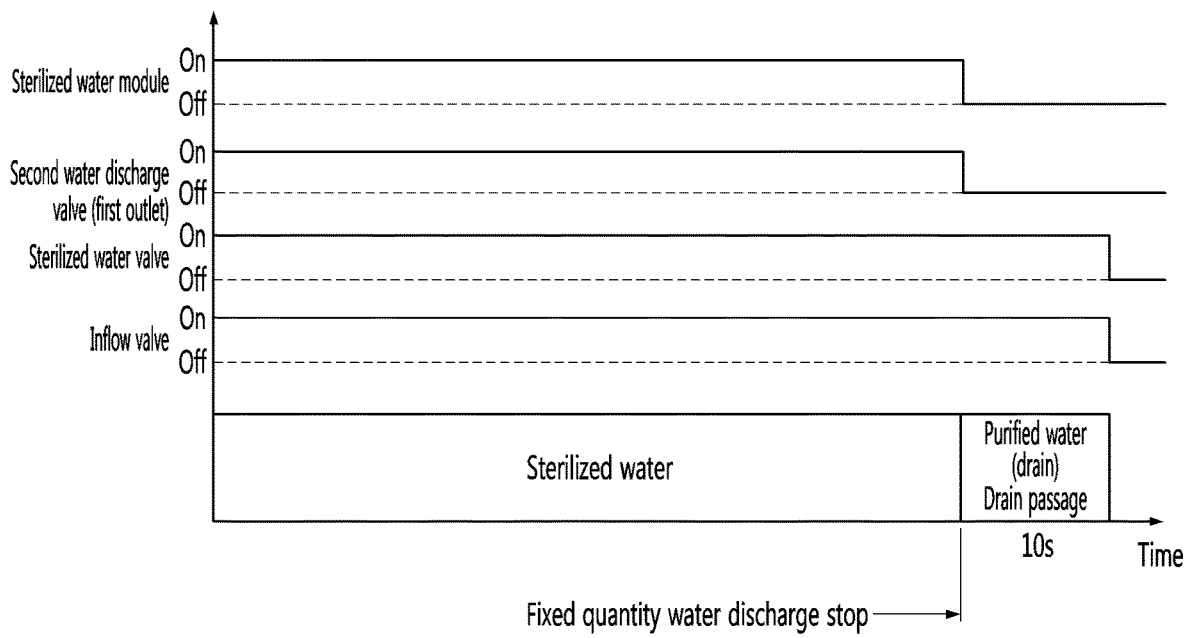
FIG. 33 is a timing view illustrating operation states of the sterilized liquid module and each of the valves when the discharging of the sterilized liquid is forcibly ended before the fixed quantity of sterilized liquid is discharged.
Figure 34:
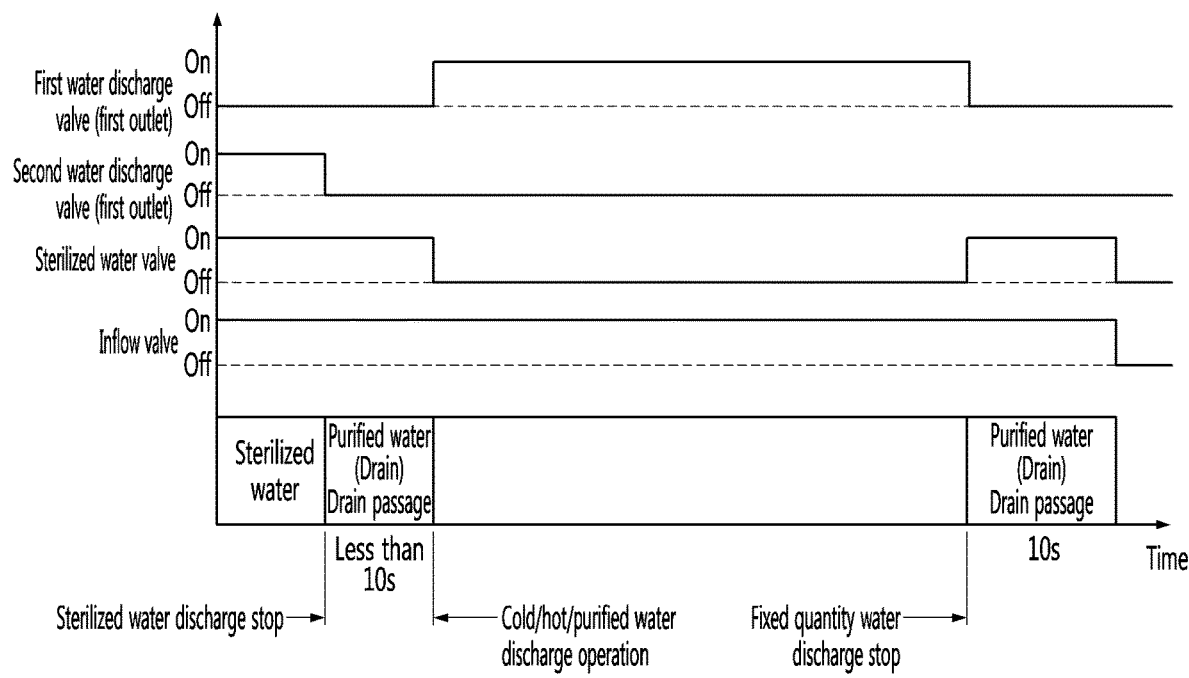
FIG. 34 is a timing view illustrating operation states of the sterilized liquid module and each of the valves when cold liquid/hot liquid/purified liquid are discharged before the fixed quantity of sterilized liquid is discharged.

FIG. 32 is a timing view illustrating operation states of a sterilized liquid module and each of valves when a fixed quantity of sterilized liquid is discharged. FIG. 33 is a timing view illustrating operation states of the sterilized liquid module and each of the valves when the discharging of the sterilized liquid is forcibly ended before the fixed quantity of sterilized liquid is discharged. FIG. 34 is a timing view illustrating operation states of the sterilized liquid module and each of the valves when cold liquid/hot liquid/purified liquid are discharged before the fixed quantity of sterilized liquid is discharged.

First, referring to FIG. 32, after a quantity of sterilized liquid is completely discharged, the purified liquid may be discharged, and the tube cleaning may be performed. In detail, when the sterilized liquid output is requested from the user, power is supplied to the sterilized liquid module 150, and the inflow valve 35 and the sterilized liquid valve 44 are opened. The first outlet of the second liquid discharge valve 62, which is connected to the second liquid discharge nozzle 220, is opened.

After a specified quantity of the sterilized liquid is discharged, the discharge of the sterilized liquid is ended, purified liquid is discharged to the second discharge nozzle 220, and then, tube cleaning between the sterilized liquid module 150 and the second discharge nozzle 220 is performed. In this process, the second liquid discharge nozzle 220 is also cleaned. Here, the power is turned off to the sterilized liquid module 150, and the inflow valve 35 and the sterilized liquid valve 44 remain in the opened state. The second liquid discharge valve 62 is maintained in the state in which the first outlet connected to the second liquid discharge nozzle 220 is opened. For example, a time for which the purified liquid is discharged to the second liquid discharge nozzle 220 may be set to about 5 seconds.

As described above, if the purified liquid is discharged after the sterilized liquid is discharged through the second discharge nozzle 220, the user cleans the fruits, vegetables, bowls, and the like using sterilized liquid, and then the fruits, vegetables, and/or bowls are rinsed by the purified liquid. Then, the user may easily rinse the sterilized liquid on the back of the cleansing object.

As described above, when the liquid discharge part through the second liquid discharge nozzle 220 is completed, the drain is started. In this process, the remaining liquid of the sterilized liquid module 150 and the sterilized liquid tube 34 may be discharged through a drain passage 50. Here, the sterilized liquid module 150 is maintained in the state in which the power is turned off, and the inflow valve 35 and the sterilized liquid valve 44 remain in the opened state. The second liquid discharge valve 62 closes the first outlet connected to the second liquid discharge nozzle 220 and opens the second outlet connected to the drain tube 50. For example, a time for the purified liquid to be drained into the drain tube 50 as described above may be set to about 10 seconds. When the drain is completed, the process enters a standby mode. In the standby mode, the sterilized liquid module 150 is maintained in the power off state, and the inflow valve 35 and the sterilized liquid valve 44 are closed.

In FIG. 32, when the first outlet of the second liquid discharge valve 62 is opened, the second outlet is blocked. On the contrary, when the second outlet of the second liquid discharge valve 62 is opened, the first outlet is blocked. That is, when the liquid is supplied from the second liquid discharge valve 62 to the second liquid discharge nozzle 220, the discharge of the liquid to the drain tube 50 is blocked. When the liquid is supplied from the second liquid discharge valve 62 to the drain valve 50, the discharging of the liquid of the second liquid discharge nozzle 220 is blocked.

Referring to FIG. 33, when forced termination is requested from the user before the sterilized liquid quantitative discharging is completed, it may be confirmed that draining is performed immediately. In detail, when the sterilized liquid output is requested from the user, power is supplied to the sterilized liquid module 150, and the inflow valve 35 and the sterilized liquid valve 44 are opened. The first outlet of the second liquid discharge valve 62, which is connected to the second liquid discharge nozzle 220, is opened. Also, before a quantity of the sterilized liquid is discharged, the forced sterilized liquid termination request is generated. As described above, when the forced termination is input, the sterilized liquid outlet is ended, and the drain immediately starts.

In this process, the remaining liquid of the sterilized liquid module 150 and the sterilized liquid tube 34 may be discharged through a drain passage 50. Here, the power is turned off to the sterilized liquid module 150, and the inflow valve 35 and the sterilized liquid valve 44 remain in the opened state. The second liquid discharge valve 62 closes the first outlet connected to the second liquid discharge nozzle 220 and opens the second outlet connected to the drain tube 50. For example, a time for the purified liquid to be drained into the drain tube 50 as described above may be set to about 10 seconds. When the drain is completed, the process enters a standby mode. In the standby mode, the sterilized liquid module 150 is maintained in the power off state, and the inflow valve 35 and the sterilized liquid valve 44 are closed.

In FIG. 33, when the first outlet of the second liquid discharge valve 62 is opened, the second outlet is blocked, and conversely, when the second outlet of the second liquid discharge valve 62 is opened, the first outlet is blocked. That is, when the liquid is supplied from the second liquid discharge valve 62 to the second liquid discharge nozzle 220, the discharge of the liquid to the drain tube 50 is blocked. When the liquid is supplied from the second liquid discharge valve 62 to the drain valve 50, the discharging of the liquid of the second liquid discharge nozzle 220 is blocked.

As described above, when the quantity of sterilized liquid is not discharged, the drain process may be immediately performed, and only when the quantity of the sterilized liquid is discharged, the first cleaning may be performed while supplying the purified liquid to the second liquid discharge nozzle 220. When the first cleaning is ended, the draining process may be performed. When the drain is forcibly ended by the cold/hot/liquid discharge request without proceeding for the set time, the drain is re-performed after the cold/hot/liquid discharge, and there is an advantage that the tube cleaning is reliably performed.

On the other hand, referring to FIG. 34, during the drain, when the cold/hot/purified liquid discharge request, the drain process is stopped, it may be seen that after the cold/hot/purified liquid discharge are performed, the drain is performed again. In detail, when the sterilized liquid output is requested from the user, power is supplied to the sterilized liquid module 150, and the inflow valve 35 and the sterilized liquid valve 44 are opened. The first outlet of the second liquid discharge valve 62, which is connected to the second liquid discharge nozzle 220, is opened.

Also, before a quantity of the sterilized liquid is discharged, the forced sterilized liquid termination request is generated. As described above, when the forced termination is input, the sterilized liquid outlet is ended, and the drain process immediately starts. In this process, the remaining liquid of the sterilized liquid module 150 and the sterilized liquid tube 34 may be discharged through a drain passage 50. Here, the power is turned off to the sterilized liquid module 150, and the inflow valve 35 and the sterilized liquid valve 44 remain in the opened state. The second liquid discharge valve 62 closes the first outlet connected to the second liquid discharge nozzle 220 and opens the second outlet connected to the drain tube 50. For example, a time for the purified liquid to be drained into the drain tube 50 as described above may be set to about 10 seconds.

In the process of draining as described above, the cold/hot/purified liquid discharge is requested from the user before the drain process is ended. As described above, if the cold/hot/purified liquid output is input, the drain process is ended, and the cold/hot/purified liquid discharge are immediately performed. In the cold/hot/clean liquid discharge process, the first liquid discharge valve 61 opens the first outlet connected to the first liquid discharge nozzle 21.

The sterilized liquid valve 44 is closed, and the inflow valve 35 is maintained in the opened state. Then, if the cold/hot/purified liquid is quantitatively output, the cold/hot/ purified liquid discharge is completed. To terminate the cold/hot/liquid purification as described above, the first liquid discharge valve 61 blocks the first outlet connected to the first liquid discharge nozzle 21 and opens the second outlet connected to the drain tube 50.

The drain process is then performed again. Here, the power is turned off to the sterilized liquid module 150, and the inflow valve 35 and the sterilized liquid valve 44 remain in the opened state. The second liquid discharge valve 62 closes the first outlet connected to the second liquid discharge nozzle 220 and opens the second outlet connected to the drain tube 50. For example, a time for the purified liquid to be drained into the drain tube 50 as described above may be set to about 10 seconds. When the drain process is completed, the process enters a standby mode. In the standby mode, the sterilized liquid module 150 is maintained in the power off state, and the inflow valve 35 and the sterilized liquid valve 44 are closed.

In FIG. 34, when the first outlet of the first liquid discharge valve 61 is opened, the second outlet is blocked, and conversely, when the second outlet of the first liquid discharge valve 61 is opened, the first outlet is blocked. That is, when the liquid is supplied from the first liquid discharge valve 61 to the second liquid discharge nozzle 210, the discharge of the liquid to the drain tube 50 is blocked. When the liquid is supplied from the first liquid discharge valve 61 to the drain valve 50, the discharging of the liquid of the first liquid discharge nozzle 210 is blocked.

Also, when the first outlet of the second liquid discharge valve 62 is opened, the second outlet is blocked, and conversely, when the second outlet of the second liquid discharge valve 62 is opened, the first outlet is blocked. That is, when the liquid is supplied from the second liquid discharge valve 62 to the second liquid discharge nozzle 220, the discharge of the liquid to the drain tube 50 is blocked. When the liquid is supplied from the second liquid discharge valve 62 to the drain valve 50, the discharging of the liquid of the second liquid discharge nozzle 220 is blocked.

According to the above, when the drain is forcibly ended by the cold/hot/liquid discharge request without proceeding for the set time, the drain is re-performed after the cold/hot/ liquid discharge, and there is an advantage that the tube cleaning is reliably performed.

Figure 35:
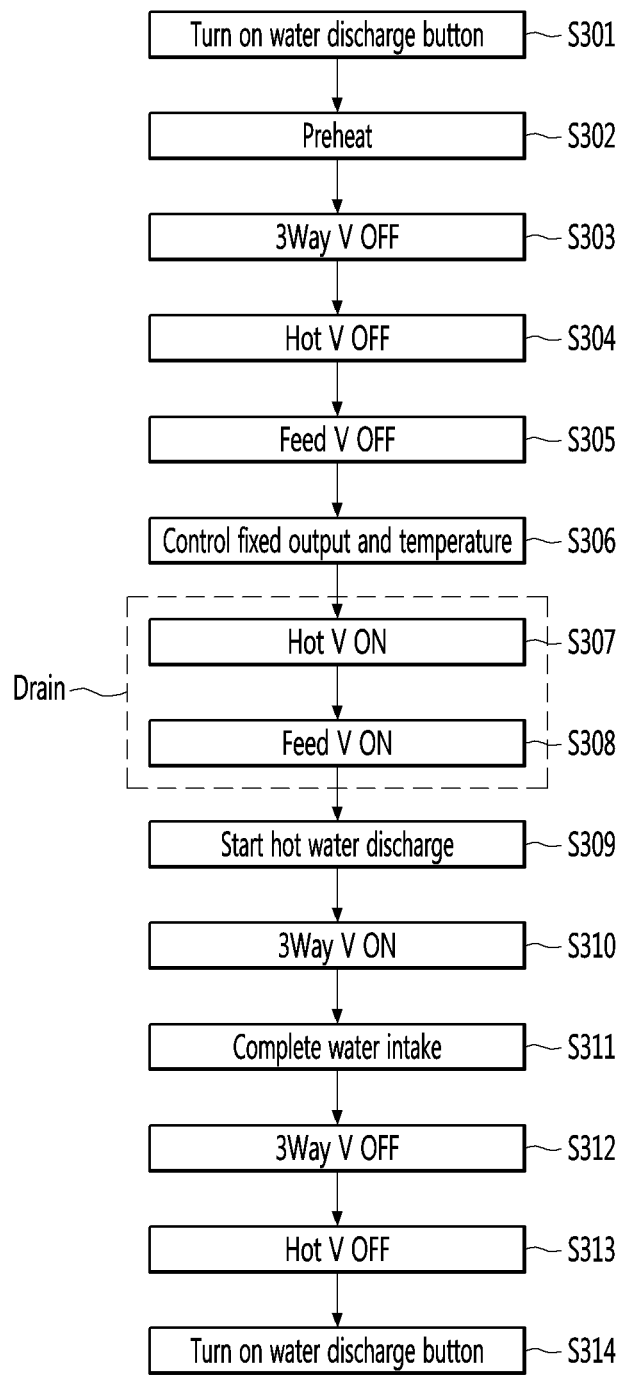
FIG. 35 is a flowchart illustrating a method for controlling discharging of hot liquid in the liquid dispensing device according to an embodiment.
Figure 36:
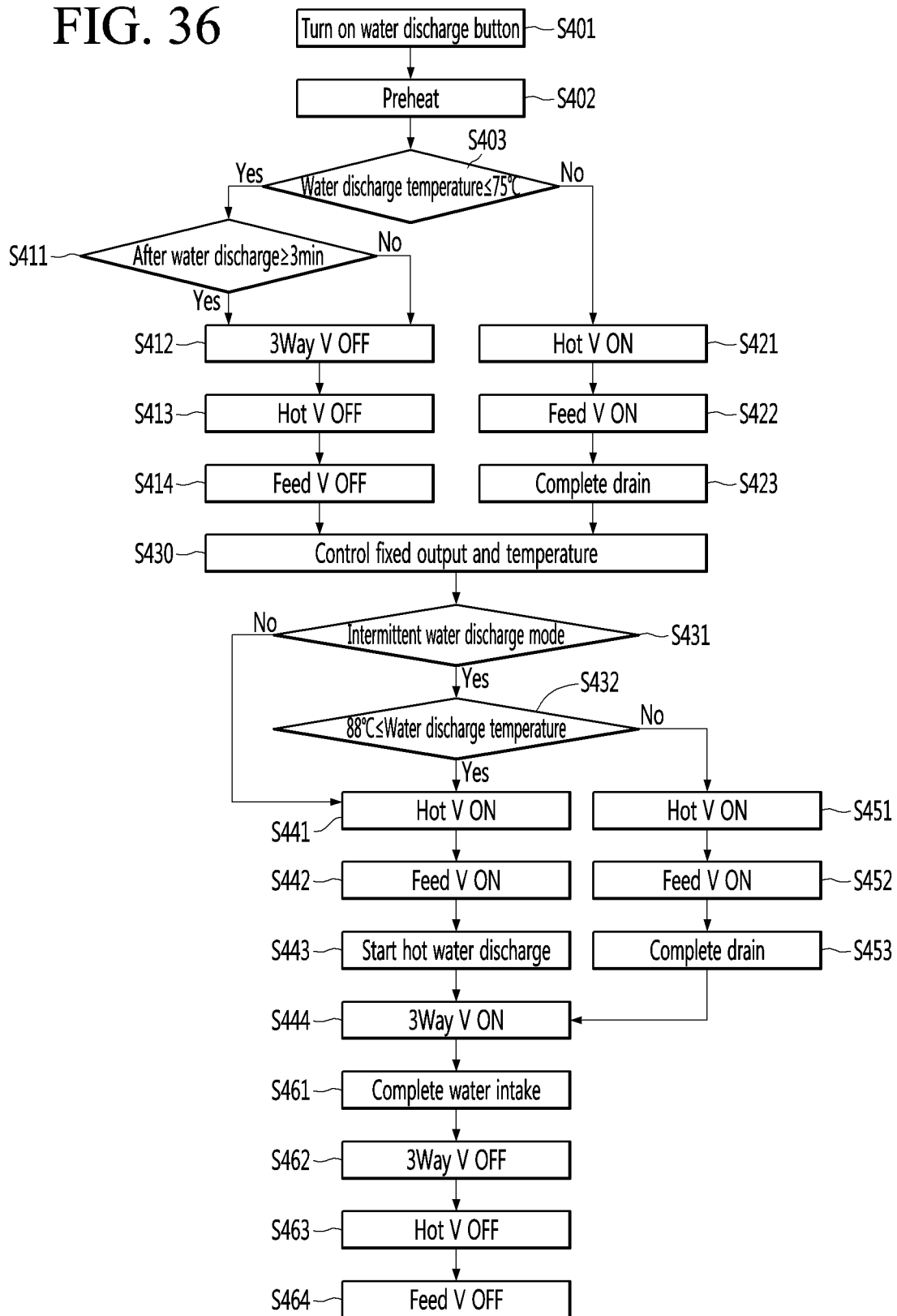
FIG. 36 is a flowchart for explaining a method for controlling discharging of hot liquid in the liquid dispensing device according to another embodiment.

FIG. 35 is a flowchart illustrating a method for controlling discharging of hot liquid in the liquid dispensing device according to an embodiment. FIG. 36 is a flowchart for explaining a method for controlling discharging of hot liquid in the liquid dispensing device according to another embodiment.

Referring to FIG. 35, the hot liquid discharging process will be described when the hot liquid corresponds to a "first cup". The reference for the first cup and the repeat cup may be set in various manners. For example, when an 'n-th' hot liquid discharging command is input, the first cup and the repeated cup may be determined according to whether a waiting time elapses after discharging the 'n-th' hot liquid. When the waiting time elapses for about 3 minutes, it may be determined as the first cup.

As another example, the first cup and the repeated cup may be determined according to a temperature of the remaining liquid detected by the hot liquid or a temperature of the first liquid discharge valve 61 of the hot liquid tank. In another example, the first cup and the repeated cup may be determined by a temperature difference between a temperature of the purified liquid flowing into the hot liquid tank and the remaining liquid detected by the first liquid discharge valve 61. For another example, the first and second cups may be determined by a temperature difference between the temperature of the hot liquid detected by the hot liquid tank and the remaining liquid detected by the first liquid discharge valve 61.

First, while the user presses the liquid discharge button 240, a hot liquid discharge command is input (S301). Then, it is determined whether the first cup or the repeated cup, and in the case of the first cup, preheating is performed immediately (S302).

In the preheated state, the first liquid discharge valve 61, the inflow valve 35, and the hot liquid valve 43 are maintained in the closed state (S303, S304, S305). However, the first liquid discharge valve 61 may be maintained in the state in which the outlet connected to the first liquid discharge nozzle 210 is closed, and the outlet connected to the drain is opened.

Then, after finishing the preheating, a predetermined fixed output is supplied to the hot liquid tank 130, and real-time temperature control is performed (S306). For example, in operation S306, an output of a working coil for heating the hot liquid tank 130 may be maintained constantly.

For example, in operation S306, an output of a working coil for heating the hot liquid tank 130 may be maintained in real-time. In detail, factors such as a temperature of the hot liquid tank 130, a temperature of the hot liquid heated in the hot liquid tank 130, the temperature of the purified liquid flowing into the hot liquid tank 130, or a flow rate of the purified liquid flowing into the hot liquid tank 130 are detected in real time, and an output of the working coil for heating the hot liquid tank 130 according to each factor may be adjusted. The preheating process may be performed, for example, in a range of about 4.2 seconds to 5.0 seconds.

Thereafter, the inflow valve 35 and the hot liquid valve 43 are sequentially opened (S307, S308). Then, the drain of the remaining liquid and/or the hot liquid in the tube starts (S309). When the hot liquid is drained, the outlet of the first liquid discharge valve 61 is opened. The drain time may be set in various manners. For example, the drain may be performed for about 3.6 seconds. When the drain is completed, the hot liquid is discharged through the first liquid discharge nozzle 210.

For the discharging of the hot liquid, the drain of the first liquid discharge valve 61 is closed, and the outlet connected to the first liquid discharge nozzle 210 is opened (S310). Then, after the set amount of hot liquid is discharged, the hot liquid discharge is ended (S311).

Thereafter, the first liquid discharge valve 61 is closed (S312). Also, the hot liquid valve 43 and the inflow valve 35 is closed in sequence (S313, S314). However, the first liquid discharge valve 61 may be maintained in the state in which the outlet connected to the first liquid discharge nozzle 210 is closed, and the outlet connected to the drain is opened.

Hereinafter, referring to FIG. 36, the hot liquid discharging process will be described when the hot liquid corresponds to the "repeated cup". The reference for the first cup and the repeat cup may be set in various manners. For example, when an 'n-th' hot liquid discharging command is input, the first cup and the repeated cup may be determined according to whether a waiting time elapses after discharging the 'n-th' hot liquid. When the waiting time elapses for about 3 minutes, it may be determined as the first cup.

As another example, the first cup and the repeated cup may be determined according to a temperature of the remaining liquid detected by the hot liquid or a temperature of the first liquid discharge valve 61 of the hot liquid tank. For another example, the first cup and the repeated cup may be determined by a temperature difference between a temperature of the purified liquid flowing into the hot liquid tank and the remaining liquid detected by the first liquid discharge valve 61. For another example, the first and second cups may be determined by a temperature difference between the temperature of the hot liquid detected by the hot liquid tank and the remaining liquid detected by the first liquid discharge valve 61.

First, while the user presses the liquid discharge button 240, a hot liquid discharge command is input (S401). Then, preheating is performed immediately (S402). Then, in the preheated state, the liquid discharge temperature is compared to the reference temperature (S403).

Here, the 'liquid discharge temperature' means a temperature of the hot liquid detected by the temperature sensor mounted on the first liquid discharge valve 61. For example, the reference temperature may be set to about 75° C. If the discharge liquid temperature is below the reference temperature (about 75° C.), the preheating is performed.

Then, to predict the temperature of the hot liquid tank 130, it is determined whether the waiting time elapses more than the reference time after the discharge. Here, the meaning of 'waiting time after the liquid discharge' means 'waiting time after '(n−1)-th' hot liquid discharging when the 'n-th' hot liquid discharging is performed.

If after the liquid discharge, the waiting time does not elapse for more than the reference time (about 3 minutes), the first liquid discharge valve 61, the inflow valve 35, and the hot liquid valve 43 are maintained in the closed state. In detail, the first liquid discharge valve 61 is controlled to be closed (S412). However, the first liquid discharge valve 61 may be maintained in the state in which the outlet connected to the first liquid discharge nozzle 210 is closed, and the outlet connected to the drain is opened.

Then, the hot liquid valve 43 is controlled to be closed (S413). Then, the inflow valve 35 is controlled to be closed (S414). The hot liquid valve 43 is installed in front of the hot liquid tank 130 based on the flow of liquid.

Also, even if the hot liquid valve 43 is closed, when the liquid is boiled in the hot liquid tank 43, the pressure of the hot liquid tank 43 increases, and a portion of the heated hot liquid is discharged from the hot liquid tank 130. The hot liquid discharged is drained through the first liquid discharge valve 61. Also, the temperature of the hot liquid to be drained is sensed in real time by the temperature sensor installed on the inlet of the first liquid discharge valve 61.

Also, even when the waiting time elapses for more than the reference time (about 3 minutes), the first liquid discharge valve 61, the inflow valve 35, and the hot liquid valve 43 are maintained in the closed state. In detail, the first liquid discharge valve 61 is controlled to be closed (S412). However, the first liquid discharge valve 61 may be maintained in the state in which the outlet connected to the first liquid discharge nozzle 210 is closed, and the outlet connected to the drain is opened.

Then, the hot liquid valve 43 is controlled to be closed (S413). Then, the inflow valve 35 is controlled to be closed (S414). Similarly, the hot liquid valve 43 is installed in front of the hot liquid tank 130 based on the flow of liquid.

Also, even if the hot liquid valve 43 is closed, when the liquid is boiled in the hot liquid tank 43, the pressure of the hot liquid tank 43 increases, a portion of the heated hot liquid is discharged from the hot liquid tank 130. The hot liquid discharged is drained through the first liquid discharge valve 61. Also, the temperature of the hot liquid to be drained is sensed in real time by the temperature sensor installed on the inlet of the first liquid discharge valve 61.

In operation S403, if the liquid discharge temperature exceeds the reference temperature (about 75° C.), preheating drain (primary drain) is performed. For this, the hot liquid valve 43 is controlled to be opened (S421). The hot liquid valve 43 is installed in front of the hot liquid tank 130 based on the flow of liquid.

Then, the inflow valve 35 is controlled to be opened (S422). Here, the first liquid discharge valve 61 may be maintained in the state in which the outlet connected to the first liquid discharge nozzle 210 is closed, and the outlet connected to the drain is opened. Therefore, the preheat drain is performed, and when the set time elapses, the preheat drain is ended (S423).

Then, in the preheating drain process, the hot liquid discharged from the hot liquid tank 130 is drained through the first liquid discharge valve 61. Also, the temperature of the hot liquid to be drained is sensed in real time by the temperature sensor installed on the inlet of the first liquid discharge valve 61. For example, the preheat drain may be performed for about 0.8 seconds to 1 second.

That is, in operation S403, if the hot liquid temperature exceeds the reference temperature (about 75° C.), while opening the hot liquid valve 43 and the inflow valve 35, preheating and draining for about 1 second are performed. In operation S403, when the liquid discharge temperature falls below the reference temperature (about 75° C.), only the preheating is performed in the state in which the hot liquid valve 43 and the inflow valve 35 are closed. As described above, the "preheating time" may be performed for about 1.0 second to about 5.2 seconds.

Thereafter, a predetermined fixed output is supplied to the hot liquid tank 130, and real-time temperature control is performed (S430). That is, after operation S414 or S423, a predetermined fixed output is supplied to the hot liquid tank 130, and real-time temperature control is performed. Then, it is determined whether the intermittent liquid discharging occurs (S431). The intermittent liquid discharging may be detected according to the determination of operation S411.

For example, in operation S411, if the waiting time is greater than or equal to the reference time after the discharging, in operation S431, it is determined that the intermittent liquid discharging is occurring. For another example, in operation S411, if the waiting time is less than the reference time after exiting, in operation S431, it is determined as the repeated cup, but is not determined that the intermittent liquid discharging is occurring.

In operation S431, if it is determined that the intermittent liquid discharge is occurring, the discharge liquid temperature detected by the temperature sensor in real-time is compared to the second reference temperature (e.g., about 88° C.) (S432). On the other hand, in operation S431, if it is not determined that the intermittent liquid discharge is not occurring, operation S432 is omitted, and operation S441 described below may be immediately performed.

On the other hand, in operation S432, when the real-time liquid discharged temperature exceeds the second reference temperature (about 88° C.), the hot liquid discharging is performed. For this, first, the hot liquid valve 43 is opened (S441). Then, the inflow valve 35 is opened (S442). Thereafter, the hot liquid is discharged (S443).

Also, for the discharging of the hot liquid, the drain of the first liquid discharge valve 61 is closed, and the outlet connected to the first liquid discharge nozzle 210 is opened (S444). Then, after the set amount of hot liquid is discharged, the hot liquid discharge is ended (S461). Thereafter, the first liquid discharge valve 61 is closed (S462). Also, the hot liquid valve 43 and the inflow valve 35 is closed in sequence (S463, S464).

However, the first liquid discharge valve 61 may be maintained in the state in which the outlet connected to the first liquid discharge nozzle 210 is closed, and the outlet connected to the drain is opened. On the other hand, in operation S432, when the liquid discharge temperature is less than the second reference temperature (about 88° C.), an additional drain process is performed before the hot liquid is discharged.

For this, the hot liquid valve 43 is controlled to be opened (S451). Then, the inflow valve 35 is controlled to be opened (S452). Here, the first liquid discharge valve 61 may be maintained in the state in which the outlet connected to the first liquid discharge nozzle 210 is closed, and the outlet connected to the drain is opened. Therefore, the additional drain process is performed, and when the set time elapses, the additional drain is ended (S453).

When the additional drain process is ended as described above, for the discharging of the hot liquid, the drain of the first liquid discharge valve 61 is closed, and the outlet connected to the first liquid discharge nozzle 210 is opened (S444). Then, after the set amount of hot liquid is discharged, the hot liquid discharge is finished (S461).

Thereafter, the first liquid discharge valve 61 is closed (S462). Also, the hot liquid valve 43 and the inflow valve 35 is closed in sequence (S463, S464). In sum, when the liquid discharge temperature exceeds about 75° C., the preheating drain (primary drain) may be performed in the preheating process. This action is to prevent boiling in the hot liquid tank.

On the other hand, when the hot liquid temperature is about 75° C. or less, since possibility of boiling in the hot liquid tank is low, the preheating drain (primary drain) may be omitted, and only the preheating may be performed. However, even a small amount of hot liquid is drained due to the boiling in the hot liquid tank.

Also, after the preheating, when the temperature of the hot liquid sensed by the first liquid discharge valve 61, i.e., the 'liquid discharge temperature' is about 88° C. or less, an additional drain process (e.g., a secondary drain) may be performed. On the other hand, after the preheating, if the temperature of the hot liquid sensed by the first liquid discharge valve 61, i.e., the 'liquid discharge temperature' exceeds about 88° C., an additional drain process (secondary drain) may be omitted, and the hot liquid discharge part may be performed immediately. Here, a time of the additional drain (secondary drain) may vary depending on the acquisition temperature. The higher the inflow temperature into the hot liquid tank, the shorter the additional drain time. For example, when the inflow temperature flowing into the hot liquid tank is less than about 30° C., the additional drain time may be performed by the time minus the preheating time from about 9.5 seconds.

For another example, when the inflow temperature flowing into the hot liquid tank ranges about 30° C. to about 40° C., the additional drain time may be performed by the time minus the preheating time from about 9.0 seconds. In another example, when the inflow temperature flowing into the hot liquid tank ranges of about 45° C. to about 60° C., the additional drain time may be performed by the time minus the preheating time from about 5.0 seconds. In another example, when the inflow temperature flowing into the hot liquid tank is about 60° C. or more, the additional drain time may be omitted.

Although not shown, when the hot liquid discharging command is input at the n-th discharge, and when the cold liquid is discharged at the (n−1)-th discharge, the drain is performed unconditionally. Here, the drain may be performed in the range in which the remaining liquid in the passage between the hot liquid tank and the first liquid discharge valve 61 is completely discharged.

Also, even when the hot liquid discharging command is input in the n-th discharging, and the integer is discharged with the (n−1)-th discharging, the drain is performed unconditionally. Here, the drain may be performed in the range in which the remaining liquid in the passage between the hot liquid tank and the first liquid discharge valve 61 is completely discharged.

On the other hand, only when the hot liquid discharging command is input in the n-th discharge, and the hot liquid is discharged even in the (n−1)-th discharge, the drain is performed immediately or without the draining according to the temperature of the remaining liquid detected by the first liquid discharge valve 61.

Further, even in the n-th discharging, even when the cold liquid discharge command is input, the drain may be performed unconditionally. Here, the drain may be performed in the range in which the remaining liquid in the passage between the cold liquid tank and the first liquid discharge valve 61 is completely discharged.

Hereinafter, another example of a process of discharging the hot liquid from the liquid dispensing device according to an embodiment will be described. First, hot liquid output is requested from the user. Then, it is determined whether the reference time elapses after the previous discharge. For example, the reference time may be set to about 3 minutes.

If the hot liquid discharging is requested in the n-th discharging, and in the (n−1)-th discharging, after the hot liquid is discharged, when the elapses time is above the reference time, only the preheating is performed without the draining. If the hot liquid discharging is performed in succession, and the time between successive hot liquid discharging is more than the reference time, it is determined as the first cup, and only preheating is performed without the draining. The reason why only preheating is performed without the draining is that the boiling does not occur due to overheating of the hot liquid tank.

In one example, the preheating may proceed for about 1.8 seconds to about 3.9 seconds. The preheating time may vary depending on a target hot liquid temperature, an intake temperature of liquid introduced into the hot liquid tank, an inflow flow rate, and an output supplied to the hot liquid tank.

Thereafter, when the preheating is ended, the discharge liquid temperature is compared to the reference temperature. For example, the 'liquid discharge temperature' may mean the temperature of the remaining liquid detected by the first liquid discharge valve 61. For another example, the 'liquid discharge temperature' may be refer to the temperature of the hot liquid discharged from the hot liquid tank. Here, the reference temperature may be set to about 88° C.

If the hot liquid is higher than the reference temperature, the hot liquid discharging is performed immediately from the first hot liquid nozzle 210. Then, when the set time elapses or the hot liquid of the target flow rate is discharged, the hot liquid discharging is ended.

On the other hand, when the liquid discharge temperature is less than the reference temperature, after the drain is selectively performed, the hot liquid discharging is performed from the first liquid discharge nozzle 210. In this case, the drain time may vary depending on the temperature of the liquid introduced into the hot liquid tank or the temperature of the hot liquid tank itself.

The higher the temperature of the liquid introduced into the hot liquid tank or the temperature of the hot liquid tank itself, the shorter the drain time. For example, when the temperature of the liquid flowing into the hot liquid tank or the temperature of the hot liquid tank itself is less than about 30° C., the drain time may be performed by about 8.5 seconds minus the preheating time.

For another example, when the temperature of the liquid flowing into the hot liquid tank or the temperature of the hot liquid tank itself is about 30° C. or more and less than about 45° C., the drain time may be performed by about 8.0 seconds minus the preheating time. For another example, when the temperature of the liquid flowing into the hot liquid tank or the temperature of the hot liquid tank itself is about 45° C. or more and less than 60° C., the drain time may be performed by about 4.0 seconds minus the preheating time. For another example, when the temperature of the liquid flowing into the hot liquid tank or the temperature of the hot liquid tank itself is about 60° C. or more, the drain time may be omitted. Also, the hot liquid discharging is performed immediately from the first hot liquid nozzle 210.

Hereinafter, another example of a process of discharging the hot liquid from the liquid dispensing device according to an embodiment will be described. First, the hot liquid output is requested from the user. Then, it is determined whether the reference time elapses after the previous discharge. For example, the reference time may be set to about 3 minutes.

If the hot liquid discharging is requested in the n-th discharging, and in the (n−1)-th discharging, after the hot liquid is discharged, when the elapses time is below the reference time, the drain in addition to the preheating is performed. That is, when the hot liquid discharge is performed successively and the time between successive hot discharge operations is less than the reference time, it is determined as a repeated cup, and the drain is performed simultaneously with the preheating. The reason why the drain is performed at the same time as the preheating is to prevent the boiling due to overheating in the hot liquid tank. The drain time may be within about 0.6 seconds to about 1.8 seconds.

Also, when the drain and preheating are ended, the hot liquid discharging is performed immediately from the first hot liquid nozzle 210. Then, when the set time elapses or the hot liquid of the target flow rate is discharged, the hot liquid discharged liquid is ended.

In another embodiment, the temperature sensor may be mounted on the first liquid discharge valve 61 positioned adjacent to the first liquid discharge nozzle 210. Therefore, the temperature satisfaction of the cold liquid and the hot liquid discharged to the first liquid discharge nozzle 210 may be improved.

If the temperature sensor is positioned on the side of the liquid purifier body installed inside the sink, even if the temperature of the hot liquid or cold liquid is satisfied in the liquid purifier body, the long tube connecting the liquid purifier body of the sink to the liquid discharge part of the outside of the sink may be changed in temperature, and as a result, the user may not have a satisfactory temperature of the hot or cold liquid. On the other hand, when the temperature sensor is mounted on the first liquid discharge valve 61 positioned near the liquid discharge nozzle for supplying the liquid to the user, the user may be provided with the hot or cold liquid of a desired temperature.

As described in this embodiment, when the temperature sensor is mounted on the first liquid discharge valve 61, the temperature sensor detects the temperature of the hot liquid or cold liquid, and if the detected temperature of the hot or cold liquid is not satisfactory, the hot liquid or cold liquid in the tube is drained without supplying the liquid to the liquid discharge nozzle, and supplying the hot liquid or cold liquid to the liquid discharge nozzle only when the temperature of the hot or cold liquid detected by the temperature sensor is satisfactory. Also, the distance between the liquid discharge nozzle and the first liquid discharge valve 61 is short, and there is little change in liquid temperature during the flow of hot liquid or cold liquid from the first liquid discharge valve 61 to the liquid discharge nozzle. Although the liquid purifier body is positioned inside the sink, and the discharge nozzle is positioned outside the sink, the discharge nozzle and the discharge valve 61 are positioned adjacent to each other, and the temperature sensor is mounted on the first discharge valve 61. The structure allows the user to receive the hot and cold liquid at the desired temperature. The drain time may be set differently according to the temperature of the purified liquid flowing into the hot liquid tank.

The liquid dispensing device according to an embodiment may include the following aspects. In one liquid discharge part installed outside the sink, one selected from the purified liquid, the cold liquid, the hot liquid and the sterilized liquid having the cleaning power may be discharged, and thus, the user may perform the cleaning and rinsing operation in one place. Also, the drinking liquid and sterilized liquid may be discharged through a separate cock and a separate tube, and thus, the user may receive only the drinking liquid without receiving the drinking liquid mixed with a portion of the sterilized liquid.

Also, the drinking liquid and the sterilized liquid may be discharged at the same point, wherein the drinking liquid may be discharged from the upper side, and the sterilized liquid may be discharged from the lower side so that the drinking liquid is not contaminated by the sterilizing liquid, and the drinking liquid discharge nozzle may be maintained in the clean state.

Also, the discharge nozzle through with the drinking liquid is discharged may have a length greater than that of the sterilized liquid nozzle, and when the drinking liquid is discharged, the interference of the sterilized liquid discharge nozzle may be prevented, and the user may place the container such as the cup under the drinking liquid discharge nozzle and discharge the drinking liquid. Also, the sterilized liquid discharge nozzle may be concealed by the discharge nozzle in which the drinking liquid is discharged, thereby preventing the accident in which the user unknowingly discharges the sterilized liquid from occurring.

Also, the nozzle control button for discharging the liquid may be provided on the top surface of the liquid discharge nozzle from which the drinking liquid positioned at the upper side is discharged to improve the user's perception of the type of discharged liquid and prevent the liquid discharge error.

Also, the liquid discharge nozzle through which sterilized liquid is discharged may be positioned at the relatively lower side so that the sterilized liquid discharge is performed only within a sink. Also, the liquid discharge nozzles for the drinking liquid may be rotatable without being interlocked with the sterilized liquid nozzle and may rotate individually. Thus, the upper discharge nozzle and the lower discharge nozzle may rotate for the user's convenience and then discharge the liquid.

Also, in the state where the liquid discharge nozzle rotates, the liquid discharge nozzle may be fixed at the position desired by the user without any rotation. The rotation operation of the liquid discharge nozzle may be performed more smoothly to improve the rotation operation feeling that the user feels.

The liquid discharge direction of the liquid discharge nozzle may be prevented from being shaken and moving in the circumferential direction, thereby stably realizing the rotation operation of the liquid discharge nozzle. The liquid discharge nozzle through which the drinking liquid is discharged and the liquid discharge nozzle through which sterilized liquid is discharged may rotate with the range set by the user.

The upper discharge nozzle and the lower discharge nozzle may be connected to one rotation shaft, and the hollow of one rotation shaft may be utilized as the tube and wire space. The inner space of the rotation shaft may be partitioned to individually secure the space for the tube and the space for the wire.

The display and input part defining the top surface of the upper liquid discharge nozzle may be separated so that the cock and the tube of the upper liquid discharge nozzle may be replaced in a state of opening an upper side. The lower frame defining the bottom surface of the lower liquid discharge nozzle may be separated so that the cock and the tube of the lower liquid discharge nozzle may be replaced in the state of opening the lower side.

Even if the liquid leaks into the display and input part defining the top surface of the upper liquid discharge nozzle, the liquid may not be introduced into the PCB but be blocked. Even if the upper discharge nozzle and the lower discharge nozzle rotate, the tangling and twisting of the tubes and wires passing through the hollow of the rotation shaft may be maximally prevented. The PCB installed on the upper liquid discharge nozzle and the wire may be easily connected to each other.

Embodiments provide a liquid dispensing device in which one driving liquid selected from purified liquid, cold liquid, and hot liquid and sterilized liquid are discharged from one liquid discharge part installed outside a sink. Embodiments also provide a liquid dispensing device in which drinking liquid and sterilized liquid are discharged through a separate cock and a separate tube. Embodiments also provide a liquid dispensing device in which drinking liquid and sterilized liquid are discharged at the same point, wherein the drinking liquid is discharged from an upper side, and the sterilized liquid is discharged from a lower side so that the drinking liquid is not contaminated by the sterilizing liquid.

Embodiments also provide a liquid dispensing device in which a liquid discharge nozzle through which drinking liquid is discharged is provided longer than a nozzle for sterilizing liquid, an interference of the sterilized liquid discharge nozzle is prevented when the drinking liquid is discharged. Embodiments also provide a liquid dispensing device in which a sterilized liquid discharge nozzle is concealed by a liquid discharge nozzle through which drinking liquid is discharged.

Embodiments also provide a liquid dispensing device in which a nozzle control button for discharging liquid is provided on a top surface of a liquid discharge nozzle from which the drinking liquid positioned at an upper side is discharged to improve user's perception of a type of discharged liquid and prevent a liquid discharge error.

Embodiments also provide a liquid dispensing device in which a liquid discharge nozzle through which sterilized liquid is discharged is positioned at a relatively lower side so that the sterilized liquid discharge is performed only within a sink.

Embodiments also provide a liquid dispensing device in which a liquid discharge nozzle through which drinking liquid is discharged is not interlocked with a nozzle through which sterilized liquid is discharged but individually rotates. Embodiments also provide a liquid dispensing device in which a liquid discharge nozzle is fixed without rotating arbitrarily in a state in which the liquid discharge nozzle rotates.

Embodiments also provide a liquid dispensing device in which a rotation operation of a liquid discharge nozzle is performed more smoothly to improve rotation operation feeling that a user feels. Embodiments also provide a liquid dispensing device in which a liquid discharge nozzle through which drinking liquid is discharged and a liquid discharge nozzle through which sterilized liquid is discharged rotate with a range set by a user.

Embodiments also provide a liquid dispensing device in which an upper discharge nozzle and a lower discharge nozzle are connected to one rotation shaft, and a hollow of one rotation shaft is utilized as a tube and wire space. Embodiments also provide a liquid dispensing device in which an inner space of a rotation shaft is partitioned to individually secure a space for a tube and a space for a wire.

Embodiments also provide a liquid dispensing device in which a display and input part defining a top surface of an upper liquid discharge nozzle is separated so that a cock and a tube of the upper liquid discharge nozzle are replaced in a state of opening an upper side. Embodiments also provide a liquid dispensing device in which a lower frame defining a bottom surface of a lower liquid discharge nozzle is separated so that a cock and a tube of the lower liquid discharge nozzle are replaced in a state of opening a lower side.

Embodiments also provide a liquid dispensing device in which, even if liquid leaks into a display and input part defining a top surface of an upper liquid discharge nozzle, the liquid is not introduced into a PCB but is blocked. Embodiments also provide a liquid dispensing device in which, even if an upper discharge nozzle and a lower discharge nozzle rotate, tangling and twisting of tubes and wires passing through a hollow of a rotation shaft are maximally prevented.

Embodiments also provide a liquid dispensing device in which a PCB installed on an upper liquid discharge nozzle and a wire are easily connected to each other. Embodiments also provide a liquid dispensing device which includes a liquid discharge part, of which at least a portion is installed to be exposed to an upper side of a sink and in which at least one of drinking liquid or sterilized liquid is discharged to the liquid discharge part.

In one embodiment, a liquid discharge part includes a first liquid discharge nozzle configured to supply at least one driving liquid selected from purified liquid, hot liquid, and cold liquid, and a second liquid discharge nozzle positioned to be spaced downward from the first liquid discharge nozzle to supply sterilized liquid having cleaning power.

The liquid discharge part may include an internal member coupled to a sink to extend vertically. The first liquid discharge part may have one side coupled to an upper side of the internal member to extend horizontally and the other side coupled to the internal member to extend horizontally.

An extension length of the first liquid discharge nozzle is greater than an extension length of the second liquid discharge nozzle.

A first cock through which at least one drinking liquid selected from the purified liquid, the hot liquid, and the cold liquid is discharged may be positioned on a lower end of one side of the first liquid discharge nozzle, and a tube connected to the first cock and having the other side passing through a hollow of the internal member may be accommodated inside the first liquid discharge nozzle.

A tube on which a second cock through which sterilized liquid is discharged is positioned and having one side connected to the second cock inside second liquid discharge nozzle and the other side passing through a hollow of the internal member may be accommodated inside the first liquid discharge nozzle.

The first liquid discharge nozzle may have a width greater than a width of the second liquid discharge nozzle. The first liquid discharge nozzle may have a thickness greater than a thickness of the second liquid discharge nozzle. A display and input part configured to select a kind of liquid discharged to the first liquid discharge nozzle and/or the second liquid discharge nozzle and having a function of a liquid discharge command may be positioned above the first liquid discharge nozzle.

A liquid discharge button may be positioned above a first cock. In a state in which the first liquid discharge nozzle and the second discharge nozzle are positioned parallel to each other, the first cock may be positioned at a position that more protrudes than the second cock, and the first cock may be positioned at a position that does not overlap the second liquid discharge nozzle. The first liquid discharge nozzle and the second liquid discharge nozzle may be rotatably coupled to the internal member.

The first liquid discharge nozzle and the second liquid discharge nozzle may rotate independently without being interlocked with each other. A first insertion part having a hollow shape into which an upper side of the internal member may be accommodated is defined in a lower end of one side of the first liquid discharge nozzle, and a second insertion part having a hollow shape through which the internal member passes may be defined in a lower end of one side of the second liquid discharge nozzle.

A first body having a hollow shape and defining an outer appearance while covering the second insertion part and the internal member may be positioned between an upper end of the sink and the second liquid discharge nozzle. A second body having a hollow shape and defining an outer appearance while covering the first insertion part and the internal member may be positioned between the first liquid discharge nozzle and the second discharge nozzle.

At least one O-ring or square ring, which is made of an elastic material to hold a clearance may be inserted between the internal member and the first insertion part and/or between the internal member and the second insertion part. At least one O-ring or square ring, which is made of an elastic material to hold a clearance may be inserted between the first insertion part and the second body and/or between the second insertion part and the first body. A square ring insertion groove that is recessed inward may be defined in an outer surface of the internal member in a circumferential direction.

An insertion part of a square ring support member may be inserted into the square ring insertion groove, and the square ring insertion member may further include a square ring support part extending horizontally from a lower end of the insertion part to the outside.

A second square ring may be seated on an upper end of the square ring support part. An upper end of the second square ring may be in contact with and supported on a lower end of the second insertion part.

An internal member may have a hollow cylindrical shape with upper and lower portions opened and may include a rotation limit hole opened by a predetermined height is defined along a circumference of a side surface thereof, and may be coupled to the sink to extend vertically.

A second liquid discharge nozzle may have one side at which a second insertion part having a cylindrical shape and rotatably connected to the internal member is defined and the other side at which a second cock connected to a tube passing through the hollow of the internal member and the rotation limit hole is positioned. The second liquid discharge nozzle may be provided with a second stopper accommodated in the rotation limit hole at one side thereof to limit a rotation range within the rotation limit hole.

At least a portion of the second stopper may protrude to the inside of the second insertion part. The liquid dispensing device may further include a first liquid discharge nozzle having one side at which a first insertion part having a cylindrical shape and rotatably connected to an upper side of the internal member is defined and the other side at which a first cock connected to a tube passing through the hollow of the internal member and an upper end of the internal member is positioned.

A first connection member having a ring shape may be coupled to an upper end of the internal member, and a pair of first stoppers may protrude upward from both sides of an upper end of the first connection member. A first stopper of which at least a portion may extend to an upper side of the first connection member to limit a rotation range of the first liquid discharge nozzle while being hung on the first stopper when the first liquid discharge nozzle rotates. At least a portion of the first stopper may protrude to the inside of the first insertion part.

The liquid dispensing device may further include a second connection member which is positioned below the first connection member and of which at least a portion is inserted into and coupled to the hollow of the internal member. The liquid dispensing device may further include a coupling member configured to connect the first connection member to the second connection member, the coupling member extending upward to partition the hollow of the internal member into a plurality of spaces.

The first liquid discharge nozzle may have the other side at which a first cock connected to a tube passing through the hollow of the internal member and an upper side of the internal member is positioned, the first liquid discharge nozzle having a shape of which a top surface is opened. The liquid discharge part may include a display and input part separably coupled to an upper side of the first liquid discharge nozzle to cover the opened top surface of the first liquid discharge nozzle.

The display and input part may include: a plate positioned at the uppermost side to define the top surface of the first liquid discharge nozzle; a frame positioned below the plate to provide a plurality of opening grooves and a sidewall extending downward along a circumference thereof; and a PCB positioned below the frame or positioned inside the frame. An outer circumference of the plate may further protrude outward than the sidewall of the frame.

A first insertion part having a hollow shape and rotatably coupled to the internal member may be defined in a lower end of one side of the first liquid discharge nozzle, and at least one connection terminal may be positioned on the PCB at a position facing the hollow of the first insertion part. At least one hook protrusion may have a shape that is convexly curved upward to hold the tube.

In a state in which the display and input part is separated from the first liquid discharge nozzle to open the upper side of the first liquid discharge nozzle, the tube and the first cock may be replaced. The second liquid discharge nozzle may have an opened lower side, and the opened lower side of the second liquid discharge nozzle may be covered by a lower frame coupled to define a bottom surface of the second liquid discharge nozzle, In a state in which the lower frame is separated to open the lower side of the second liquid discharge nozzle, the tube and the second cock may be replaced.

In certain implementations, a liquid dispensing device provided at a sink comprises: an cylinder body coupled to the sink to extend vertically; a first liquid discharge nozzle coupled to an upper region of the cylinder body to extend horizontally, the first liquid discharge nozzle being configured to supply at least one of a purified liquid, a heated liquid, or a cooled liquid; and a second liquid discharge nozzle coupled to the cylinder body to extend horizontally, the second liquid discharge nozzle being positioned to be spaced downward from the first liquid discharge nozzle to supply a sterilizing liquid, wherein an extending length of the first liquid discharge nozzle is greater than an extending length of the second liquid discharge nozzle.

A width of the first liquid discharge nozzle is greater than a width of the second liquid discharge nozzle and a thickness of the first liquid discharge nozzle is greater than a thickness of the second liquid discharge nozzle.

The liquid dispenser may further comprise a user interface device configured to receive a first input related to selecting a kind of liquid to be discharged by the first liquid discharge nozzle or the second liquid discharge nozzle and to receive a second input related to a liquid discharge command, wherein the user interface device is positioned at an upper surface of the first liquid discharge nozzle, wherein the user interface device includes a liquid discharge button that is positioned above a first cock through which the at least one of the purified liquid, the heated liquid, or the cooled liquid is discharged from the first liquid discharge nozzle.

A first cock through which the at least one of the purified liquid, the heated liquid, or the cooled liquid is discharged is positioned on a lower end of one side of the first liquid discharge nozzle, and a first tube having a first side connected to the first cock and a second side passing into a hollow of the cylinder body is positioned to extend inside the first liquid discharge nozzle, and a second cock through which the sterilizing liquid is discharged is positioned on a lower end of one side of the second liquid discharge nozzle, and a second tube having a first side connected to the second cock and a second side passing into the hollow of the cylinder body is positioned to extend inside the second liquid discharge nozzle and when the first liquid discharge nozzle and the second discharge nozzle are positioned to extend parallel to each other, the first cock is positioned further from the cylinder body than the second cock, and the first cock is positioned to not vertically overlap the second liquid discharge nozzle. The first liquid discharge nozzle and the second liquid discharge nozzle are rotatably coupled to the cylinder body.

In an implementation, a liquid dispenser is provided at an outer surface of a sink and comprises: a cylinder body coupled to the sink to extend vertically; a first liquid discharge nozzle having one side rotatably coupled to an upper end of the cylinder body to extend horizontally; and a second liquid discharge nozzle having one side coupled to the cylinder body to extend horizontally, the second liquid discharge nozzle being positioned to be spaced downward from the first liquid discharge nozzle, wherein the first liquid discharge nozzle and the second liquid discharge nozzle rotate independently with respect to the cylinder body.

A first insertion extension may have a hollow shape into which the upper end of the cylinder body is accommodated is defined in a lower end of one side of the first liquid discharge nozzle, and a second insertion extension may have a hollow shape through which a portion of the cylinder body passes is defined in a lower end of one side of the second liquid discharge nozzle. a first body having a hollow shape and defining an outer appearance to cover the second insertion extension and a section of the cylinder body is positioned between the outer surface of the sink and the second liquid discharge nozzle, and a second body having a hollow shape and defining an outer appearance to cover the first insertion extension and a section of the cylinder body is positioned between the first liquid discharge nozzle and the second discharge nozzle.

At least one O-ring or square ring, which is made of an elastic material to hold a clearance may be inserted at least one of between the cylinder body and the first insertion extension or between the cylinder body and the second insertion extension. At least one O-ring or square ring, which is made of an elastic material to hold a clearance may be inserted at one of between the first insertion extension and the second body or between the second insertion extension and the first body.

A square ring insertion groove that is recessed inward is defined in an outer surface of the cylinder body in a circumferential direction, an insertion section of a square ring support is inserted into the square ring insertion groove, and the square ring insertion further includes a square ring support extending horizontally from a lower end of the insertion section to the outside, and a second square ring is seated on an upper end of the square ring support. An upper end of the second square ring may be in contact with and supported on a lower end of the second insertion extension.

In another implementation, a liquid dispenser may be provided outside of a sink and comprise: a cylinder body that has a hollow cylindrical shape with an upper end and a lower end that are open, and a rotation limit hole opened by a predetermined height that is defined along a circumference of a side surface thereof, the cylinder body being coupled to the sink to extend vertically; and a liquid discharge nozzle which has one side at which an insertion extension having a cylindrical shape and rotatably connected to the cylinder body is defined and the other side at which a cock connected to a tube extending into the hollow of the cylinder body and the rotation limit hole is positioned, the liquid discharge nozzle being provided with a stopper accommodated in the rotation limit hole at one side thereof to limit a rotation range of the liquid discharge nozzle.

At least a portion of the stopper protrudes inside of the insertion extension. The liquid discharge nozzle is a second liquid discharge nozzle, the insertion extension is a second insertion extension, the tube is a second tube, and the cock is a second cock, and wherein the liquid dispenser further comprises: a first liquid discharge nozzle having one side at which a first insertion extensions having a cylindrical shape and rotatably connected to an upper side of the cylinder body is defined and the other side at which a first cock connected to a first tube extending into the hollow of the cylinder body and an upper end of the cylinder body is positioned.

A first connection member having a ring shape is coupled to an upper end of the cylinder body, and a pair of stoppers protrude upward from respective sides of an upper end of the first connection member, and wherein at least a portion of a first stopper, of the pair of stoppers, extends to an upper side of the first connection member to limit a rotation range of the first liquid discharge nozzle while being hung on the first stopper when the first liquid discharge nozzle rotates. The first stopper extends to protrude inside of the first insertion extension.

The liquid dispenser may further comprise a second connection member which is positioned below the first connection member, at least a portion of the second connection member being inserted into and coupled to the hollow of the cylinder body and a coupling configured to connect the first connection member to the second connection member, the coupling member extending upward to partition the hollow of the cylinder body into a plurality of spaces.

In another implementation, a liquid dispenser may be provided at a sink and comprise: a cylinder body having a hollow cylindrical shape with open upper and lower ends that are opened, the cylinder body extending vertically to be coupled to the sink; a first liquid discharge nozzle having a first side coupled to an upper section of the cylinder body to extend horizontally and a second side at which a first cock connected to a first tube passing through the first liquid discharge nozzle and into a hollow section of the cylinder body is positioned, the first liquid discharge nozzle having an upper region that is opened; and a user interface device that is separably coupled to the upper region of the first liquid discharge nozzle, the user interface device covering the opened upper region of the first liquid discharge nozzle when coupled to the first liquid discharge nozzle.

The user interface device includes: a plate positioned at the uppermost side to define the top surface of the first liquid discharge nozzle; a frame positioned below the plate to provide a plurality of opening grooves and a sidewall extending downward along a circumference thereof; and a PCB positioned below the frame or positioned inside the frame. An outer circumference of the plate further protrudes outward than the sidewall of the frame.

The liquid dispenser may further comprise: a first insertion extension having a hollow shape, rotatably coupled to the cylinder body, and defined in a lower end of the first side of the first liquid discharge nozzle, and at least one connection terminal is positioned on the PCB at a position facing an interior of the first insertion extension. wherein the first liquid discharge nozzle includes at least one hook protrusion that is convexly curved upward to hold the first tube.

The first liquid discharge nozzle may include at least one hook protrusion that is convexly curved upward to hold the first tube. The first tube and the first cock may be configured to be removable from the first liquid discharge nozzle when the interface device is removed from the first liquid discharge nozzle to open the upper region of the first liquid discharge nozzle.

The liquid dispenser may further comprise: a second liquid discharge nozzle that has one side coupled to the cylinder body, that extends horizontally, and on which a second cock coupled to a second tube extending into a hollow of the cylinder body is positioned, the second liquid discharge nozzle being positioned to be spaced downward from the first liquid discharge nozzle. The second liquid discharge nozzle has an opened lower region, and the opened lower region of the second liquid discharge nozzle is covered by a lower frame to define a bottom surface of the second liquid discharge nozzle, and the second tube and the second cock are configured to be removed from the second liquid discharge nozzle when the lower frame is removed to expose the open lower region of the second liquid discharge nozzle.

In another implementation, a liquid dispenser comprises: a hollow cylindrical body extending upward from a sink; a first liquid discharge nozzle rotatably coupled to an outer circumferential surface of the cylinder body, the first liquid discharge nozzle being configured to supply a drinkable fluid that includes at least one of a purified liquid, a heated liquid, or a cooled liquid; and a second liquid discharge nozzle positioned below the first liquid discharge nozzle and rotatably coupled to the outer circumferential surface of the cylinder body, and the second liquid discharge nozzle being configured to supply a cleaning fluid that is not drinkable, wherein a rotation radius of the first liquid discharge nozzle is greater than a rotation radius of the second liquid discharge nozzle.

In another implementation, a liquid dispenser comprises: a hollow cylinder body extending linearly upward from a sink; a first outer discharge nozzle supported on an outer circumferential surface of the cylinder body to rotate; a second liquid discharge nozzle positioned below the first liquid discharge nozzle, the second liquid discharge nozzle being supported on the outer circumferential surface of the cylinder body to rotate; and a cylinder cover positioned between the first liquid discharge nozzle and the second liquid discharge nozzle, the second body being coupled to the outer circumferential surface of the cylinder body, wherein when the second liquid discharge nozzle rotates, the cylinder cover engages first liquid discharge nozzle such that the first liquid discharge nozzle is prevented from rotating.

In another implementation, a liquid dispenser comprises: a cylinder body extending upward from a sink and in which a rotation limit hole opened in a circumferential direction is defined in one side thereof; a tube accommodated in the cylinder body to extend by passing through the rotation limit hole; and a liquid discharge nozzle having a first side at which a cock connected to the tube is installed and a second side at which a stopper passing through the rotation limit hole is positioned, the liquid discharge nozzle being supported on an outer circumferential surface of the cylinder body to rotate, wherein, when the liquid discharge nozzle rotates, the stopper is hung on both ends of the rotation limit hole to limit a rotation range of the liquid discharge nozzle.

In another implementation, a liquid dispenser comprises: an cylinder body coupled to extending linearly upward from a sink; a liquid discharge nozzle coupled at a first end to an outer circumferential surface of the cylinder body and a second end where a cock is positioned; a user interface device configured to cover an opened upper region of the liquid discharge nozzle; and a tube configured to pass into the cylinder body, the tube being connected to the cock of the first liquid discharge nozzle, wherein, in when the user interface device is separated from the liquid discharge nozzle, at least one of the tube or the cock are configured to be separated from and replaced through the opened upper region of the liquid discharge nozzle.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A liquid dispenser provided at a sink and comprising:
   a cylinder body coupled to the sink;
   a first liquid discharge nozzle coupled to the cylinder body, the first liquid discharge nozzle supplying at least one of a purified liquid, a heated liquid, or a cooled liquid; and
   a second liquid discharge nozzle coupled to the cylinder body the second liquid discharge nozzle being spaced from the first liquid discharge nozzle and supplying a sterilizing liquid,
   wherein the liquid dispenser further comprises a touch screen positioned at an upper surface of the first liquid discharge nozzle, and
   wherein the touch screen controls each of a hot, purified, cold, sterilized liquid selection function, a liquid discharge command function, a cold and hot liquid temperature setting and display function, a filter replacement cycle notification function, a function of setting capacity of liquid discharged, and a function of setting a discharge time of the liquid discharged.

2. The liquid dispenser of claim 1,
   wherein the first liquid discharge nozzle and the second liquid discharge nozzle rotate independently with respect to the cylinder body.

3. The liquid dispenser according to claim 2, wherein a first insertion extension having a hollow shape into which an upper end of the cylinder body is accommodated is defined in a lower end of one side of the first liquid discharge nozzle, and
   a second insertion extension having a hollow shape through which a portion of the cylinder body passes is defined in a lower end of one side of the second liquid discharge nozzle.

4. The liquid dispenser according to claim 3, wherein a first body having a hollow shape and defining an outer appearance to cover the second insertion extension and a section of the cylinder body is positioned between an outer surface of the sink and the second liquid discharge nozzle, and
   a second body having a hollow shape and defining an outer appearance to cover the first insertion extension and a section of the cylinder body is positioned between the first liquid discharge nozzle and the second liquid discharge nozzle.

5. The liquid dispenser according to claim 4, wherein at least one O-ring or square ring, which is made of an elastic material to hold a clearance, is inserted at least one of between the cylinder body and the first insertion extension or between the cylinder body and the second insertion extension.

6. The liquid dispenser according to claim 4, wherein at least one O-ring or square ring, which is made of an elastic material to hold a clearance, is inserted at one of between the first insertion extension and the second body or between the second insertion extension and the first body.

7. The liquid dispenser according to claim 4, wherein a square ring insertion groove that is recessed inward is defined in an outer surface of the cylinder body in a circumferential direction,
an insertion section of a square ring support is inserted into the square ring insertion groove, and the square ring insertion groove further includes a square ring support extending horizontally from a lower end of the insertion section to an outside, and
a second square ring is seated on an upper end of the square ring support.

8. The liquid dispenser according to claim 7, wherein an upper end of the second square ring is in contact with and supported on a lower end of the second insertion extension.

9. The liquid dispenser of claim 1, wherein:
the cylinder body includes a hollow and a rotation limit hole opened by a predetermined height that is defined along a circumference of a side surface thereof,
the second liquid discharge nozzle has one side at which an insertion extension having a cylindrical shape and rotatably connected to the cylinder body is defined and another side at which a cock connected to a tube extending into the hollow of the cylinder body and the rotation limit hole is positioned, the second liquid discharge nozzle being provided with a second stopper accommodated in the rotation limit hole at one side thereof to limit a rotation range of the second liquid discharge nozzle.

10. The liquid dispenser according to claim 9, wherein at least a portion of the stopper protrudes inside of the insertion extension.

11. The liquid dispenser according to claim 9, wherein the insertion extension is a second insertion extension, the tube is a second tube, and the cock is a second cock, and
wherein the first liquid discharge nozzle has one side at which a first insertion extension having a cylindrical shape is defined and another side at which a first cock connected to a first tube extending into the hollow of the cylinder body and an upper end of the cylinder body is positioned.

12. The liquid dispenser according to claim 11, wherein a first connection member having a ring shape is coupled to an upper end of the cylinder body, and a pair of stoppers protrude upward from respective sides of an upper end of the first connection member, wherein the pair of stoppers include a first stopper and a third stopper, and
wherein at least a portion of the first stopper extends to an upper side of the first connection member to limit a rotation range of the first liquid discharge nozzle while being hung on the first stopper when the first liquid discharge nozzle rotates.

13. The liquid dispenser according to claim 12, wherein the first stopper extends to protrude inside of the first insertion extension.

14. The liquid dispenser according to claim 12, further comprising a second connection member which is positioned below the first connection member, at least a portion of the second connection member being inserted into and coupled to the hollow of the cylinder body.

15. The liquid dispenser according to claim 14, further comprising a coupling member configured to connect the first connection member to the second connection member, the coupling member extending upward to partition the hollow of the cylinder body into a plurality of spaces.

16. The liquid dispenser of claim 1, wherein:
the first liquid discharge nozzle has a first side coupled to an upper section of the cylinder body to extend horizontally and a second side at which a first cock connected to a first tube passing through the first liquid discharge nozzle and into a hollow section of the cylinder body is positioned, the first liquid discharge nozzle having an upper region that is opened, and
the touch screen is separably coupled to the upper region of the first liquid discharge nozzle, the touch screen covering the opened upper region of the first liquid discharge nozzle when coupled to the first liquid discharge nozzle.

17. The liquid dispenser according to claim 16, wherein the touch screen includes:
a plate positioned at an uppermost side to define a top surface of the first liquid discharge nozzle;
a frame positioned below the plate to provide a plurality of opening grooves and a sidewall extending downward along a circumference thereof; and
a printed circuit board (PCB) positioned below the frame or positioned inside the frame.

18. The liquid dispenser according to claim 17, wherein an outer circumference of the plate protrudes further outward than the sidewall of the frame.

19. The liquid dispenser according to claim 16, further comprising:
a first insertion extension having a hollow shape, rotatably coupled to the cylinder body, and defined in a lower end of the first side of the first liquid discharge nozzle, and
at least one connection terminal that is positioned on the PCB at a position facing an interior of the first insertion extension.

20. The liquid dispenser according to claim 16, wherein the first liquid discharge nozzle includes at least one hook protrusion that is convexly curved upward to hold the first tube.

21. The liquid dispenser according to claim 16, wherein the first tube and the first cock are configured to be removable from the first liquid discharge nozzle when the touch screen is removed from the first liquid discharge nozzle to open the upper region of the first liquid discharge nozzle.

22. The liquid dispenser according to claim 16, wherein a second cock coupled to a second tube extending into a hollow of the cylinder body is positioned on the second liquid discharge nozzle.

23. The liquid dispenser according to claim 22, wherein the second liquid discharge nozzle has an opened lower region, and the opened lower region of the second liquid discharge nozzle is covered by a lower frame to define a bottom surface of the second liquid discharge nozzle, and
the second tube and the second cock are configured to be removed from the second liquid discharge nozzle when the lower frame is removed to expose the open lower region of the second liquid discharge nozzle.

24. The liquid dispenser according to claim 1, wherein a first cock through which the at least one of the purified liquid, the heated liquid, or the cooled liquid is discharged is positioned on a lower end of one side of the first liquid discharge nozzle, and a first tube having a first side connected to the first cock and a second side passing into a hollow of the cylinder body is positioned to extend inside the first liquid discharge nozzle, and
a second cock through which the sterilizing liquid is discharged is positioned on a lower end of one side of the second liquid discharge nozzle, and a second tube having a first side connected to the second cock and a second side passing into the hollow of the cylinder body is positioned to extend inside the second liquid discharge nozzle.

25. The liquid dispenser according to claim 24, wherein, when the first liquid discharge nozzle and the second liquid discharge nozzle are positioned to extend parallel to each other, the first cock is positioned further from the cylinder body than the second cock, and the first cock is positioned to not vertically overlap the second liquid discharge nozzle.

26. The liquid dispenser according to claim 1, wherein a width of the first liquid discharge nozzle is greater than a width of the second liquid discharge nozzle.

27. The liquid dispenser according to claim 1, wherein a thickness of the first liquid discharge nozzle is greater than a thickness of the second liquid discharge nozzle.

28. The liquid dispenser according to claim 1, wherein the touch screen includes a liquid discharge button that is positioned above a first cock through which the at least one of the purified liquid, the heated liquid, or the cooled liquid is discharged from the first liquid discharge nozzle.

29. The liquid dispenser according to claim 1, wherein the first liquid discharge nozzle and the second liquid discharge nozzle are rotatably coupled to the cylinder body.

30. The liquid dispenser of claim 1,
wherein the sterilizing liquid is a cleaning fluid that is not drinkable, and
wherein a rotation radius of the first liquid discharge nozzle is greater than a rotation radius of the second liquid discharge nozzle.

31. The liquid dispenser of claim 1, further comprising:
a cylinder cover positioned between the first liquid discharge nozzle and the second liquid discharge nozzle, the cylinder cover being coupled to an outer circumferential surface of the cylinder body,
wherein when the second liquid discharge nozzle rotates, the cylinder cover engages the first liquid discharge nozzle such that the first liquid discharge nozzle is prevented from rotating.

32. The liquid dispenser of claim 1, wherein
a rotation limit hole opened in a circumferential direction is defined in one side of the cylinder body;
the liquid dispenser further includes a tube accommodated in the cylinder body to extend by passing through the rotation limit hole; and
the second liquid discharge nozzle has a first side at which a cock connected to the tube is installed and a second side at which a stopper passing through the rotation limit hole is positioned,
wherein, when the second liquid discharge nozzle rotates, the stopper contacts opposing ends of the rotation limit hole to limit a rotation range of the second liquid discharge nozzle.

33. The liquid dispenser of claim 1, wherein
the touch screen is configured to cover an opened upper region of the first liquid discharge nozzle; and
a tube configured to pass into the cylinder body, the tube being connected to a cock of the first liquid discharge nozzle,
wherein, when the touch screen is separated from the first liquid discharge nozzle, at least one of the tube or the cock are configured to be separated from and through the opened upper region of the first liquid discharge nozzle.

34. The liquid dispenser of claim 1, wherein:
the cylinder body extends vertically from the sink,
the first liquid discharge nozzle is coupled to an upper region of the cylinder body and extends horizontally, and
the second liquid discharge nozzle is positioned downward from the first liquid discharge nozzle.

35. The liquid dispenser of claim 1, wherein an extending length of the first liquid discharge nozzle is greater than an extending length of the second liquid discharge nozzle.

36. A liquid dispenser provided at a sink and comprising:
a cylinder body coupled to the sink;
a first liquid discharge nozzle coupled to the cylinder body, the first liquid discharge nozzle supplying at least one of a purified liquid, a heated liquid, or a cooled liquid; and
a second liquid discharge nozzle coupled to the cylinder body, the second liquid discharge nozzle being spaced from the first liquid discharge nozzle and supplying a sterilizing liquid,
wherein the liquid dispenser comprises a drain tube that does not drain to a sink drain,
wherein the liquid dispenser further comprises a user interface device which receives a first input which controls discharge through the first liquid discharge nozzle and the second liquid discharge nozzle,
wherein the user interface device is positioned at an upper surface of the first liquid discharge nozzle, and
wherein the user interface device receives a second input which controls a drain function of the drain tube.

* * * * *